(12) United States Patent
Lawrence et al.

(10) Patent No.: US 7,388,074 B2
(45) Date of Patent: Jun. 17, 2008

(54) MUTANT PLASMINOGEN ACTIVATOR-INHIBITOR TYPE 1 (PAI-1) AND USES THEREOF

(75) Inventors: Daniel A. Lawrence, Derwood, MD (US); Steingrimor P. Stefansson, Gaithersburg, MD (US)

(73) Assignee: The Regents of The University of Michigan, Ann Arbor, MI (US)

( * ) Notice: Subject to any disclaimer, the term of this patent is extended or adjusted under 35 U.S.C. 154(b) by 153 days.

(21) Appl. No.: 10/259,609

(22) Filed: Sep. 30, 2002

(65) Prior Publication Data

US 2003/0216321 A1 Nov. 20, 2003

Related U.S. Application Data

(60) Division of application No. 09/324,494, filed on Jun. 2, 1999, now Pat. No. 6,489,143, which is a continuation of application No. 08/840,204, filed on Apr. 11, 1997, now Pat. No. 6,103,498.

(60) Provisional application No. 60/015,299, filed on Apr. 12, 1996.

(51) Int. Cl.
*A61K 38/00* (2006.01)

(52) U.S. Cl. .......................... 530/350; 514/2

(58) Field of Classification Search ............... 530/350; 514/2, 12; 435/183, 218
See application file for complete search history.

(56) References Cited

OTHER PUBLICATIONS

Audenaert et al. Conversion of Plasminogen Activator Inhibitor-1 from Inhibitor to Substrate by Point Mutation in the Reactive-site Loop. (1994) J. Biol. Chem. vol. 269, No. 30, pp. 19559-19564.*
Tsiang et al., "Protein Engineering Thrombin for Optimal Specificity and Potency of Anticoagulant Activity in vivo", Biochemistry 35: 16449-16457 (1996).*
Andreasen, PA., et al, "Receptor-mediated endocytosis of plasminogen activators and activator/inhibitor complexes," *FEBS Letters* (1994) 338:239-245.
Berkenpas, MB., et al, "Molecular Evolution of Plasminogen. Activator Inhibitor-i Functional Stability", *EMBO J.* (1995) 14(13):2969-2977.
Biemond, B.J., et al, "Thrombolysis and Reocclusion in Experimental Jugular Vein and Coronary Artery Thrombosis," *Circulation* (1995) 91(4): 1175-1181.
Carrell, R.W., et al, "The Biostructural Pathology of the Serpins: Critical Function of Sheet Opening Mechanism," *Biol. Chem* Hoppel-Seyler (1996) 377:1-17.
Ehrlich. H.J., et al., "Alteration of Serpin Specificity by a Protein Cofactor," *J. Biol. Chem* (1990) 265(22): 13029-13035.
Ehrlich, H.J., et al., "Functional Interaction of Plasminogen Activator Inhibitor Type 1 (PAI-1) and Heparin," *Biochemistry* (1991) 30:1021-1028.
Erlich, H.J., et al, "Thrombin Neutralizes Plasminogen Activator Inhibitor I (PM-1) that is Complexed with Vitronectin in the Endothelial Cell Matrix," *J. Cell Biol.* (1991) 115(6):1773-1781.
Erlich, H.J., et al, "Elucidation of Structural Requirements on Plasminogen Activator Inhibitor I for BindingtoHeparin," *J. Biol. Chem.* (1992) 267(16): 11606-11611.
Keijer, J., et al., "On the Target Specificity of Plasminogen Activator Inhibitor 1: The Role of Heparin, Vitronectin, and the Reactive Site," *Blood* (1991) 78(5): 1254-1261.
Keijer, J., et al., "The Interaction of Plasminogen Activator Inhibitor I with Plasminogen Activators (Tissue-Type and urokinase-Type) and Fibrin: Localization of Interaction Sites and Physiologic Relevance," *Blood* (1991) 78(2):40 1-409.
Keijer, J., et al., "Vitronectin governs the Interaction between Plasminogen Activator Inhibitor I and Tissue-type Plasminogen Activator," *Biol. Chem.* (1991) 266(16):10700-10707.
Kost, C., et al., "Mapping of Binding Sites for Heparin, Plasminogen Activator Inhibitor-i, and Plasminogen to Vitronectin's Heparin-binding Region Reveals a Novel Vitronectin-dependent Feedback Mechanism for the Control of Plasmin Formation," *J. Biol. Chem* (1992) 267(17):12098-12105.
Lawrence, D.A. et al., "Structure-Function Studies of the Serpin Plasminogen Activator Inhibitor Type 1,"*J. Biol. Chem.* (1990) 265(33):20293-20301.
Lawrence, D.A. et al., "Engineering Plasminogen Activator Inhibitor 1 Mutants with Increased Functional Stability", *Biochemistry* (1994)33:3643-3648.

(Continued)

*Primary Examiner*—Robert Mondesi
*Assistant Examiner*—Anand Desai
(74) *Attorney, Agent, or Firm*—Marshall, Gerstein & Borun LLP

(57) ABSTRACT

Mutants of the human PAI-1 protein are described which are inhibitors of neutrophil elastase or are inhibitors of vitronectin (Vn)-dependent cell migration. These mutants preferably comprise one or two amino acid substitutions in the reactive center loop of PAI-1, particularly at positions 331 and 346 of the mature protein. These mutants are notable in being resistant to inactivation by elastase, having high affinity for Vn, or both properties. These mutant proteins as pharmaceutical compositions are used to inhibit elastase in a subject, thereby treating a number of disorders associated with elastase activity, most notatably emphysema, ARDS, inflammatory lung injury and cystic fibrosis. The mutants which interact with Vn are used to inhibit cell migration in a subject, thereby treating diseases or conditions associated with undesired cell migration and proliferation, particularly of smooth muscle cells. Such conditions include atherosclerosis, post angioplasty restenosis, fibrosis associated with chronic inflammation or chemotherapy, tumor invasion and metastasis and conditions in which angiogenesis is pathogenic. Also disclosed are peptides of such mutant proteins, mutant-specific antibodies, nucleic acid molecules, particularly DNA, encoding the mutant protein and host cells transformed by such nucleic acids.

13 Claims, 43 Drawing Sheets

OTHER PUBLICATIONS

Lawrence, D.A. et al., "Localization of Vitronectin Binding Domain in Plasminogen Activator Inhibitor-I," *Biiol. Chem.* (1994) 269(21): 15223-15228.

Lawrence, D.A. et al., "Serpin Reactive Center Loop Mobility is Required for Inhibitor Function But Not for Enzyme Recognition", *J. Biol. Chem.* (1994) 269(44):27657-27662.

Meijer, M. van, et al., "Determination of the Vitronectin Binding Site on Plasminogen Activator Inhibitor 1 (PM-I)," *Federation of European Biochemical Societies* (1994) 352:342-346.

Naski, M.C., et al., "Kinetics of Inactivation Of α-Thrombin by Plasminogen Activator Inhibitor-1," *J Biol. Chem.* (1993) 268(17): 12367-12372.

Nykjaer, A., et al., "Purified $\alpha_2$-Macroglobulin Receptor/LDL Receptor-related Protein Binds Urokinase-Plasminogen Activator Inhibitor Type-i Complex," *J Biol. Chem.* (1992) 267(21): 14543-14546.

Polliinen, J., et al., "Distinct Localizations of Urokinase-type Plasminogen Activator and its Type I Inhibitor under Cultured Human Fibroblasts and Sarcoma Cells," *J. Cell Biol.* (1987)104:1085-1096.

Preissner, K.T., et al., "Structural Requirements for the Extracellular Interaction of Plasminogen Activator Inhibitor 1 with Endothelial Cell Matrix-associated Vitronectin," *J. Biol. Chem.* (1990) 265(30);18490-18498.

Reilly, T.M., et al., "Recombinant Plasminogen Activator Inhibitor Type 1: A Review of Structural, Functional, and Biological Aspects", *Blood Coagulation and Fibrinolysis* (1994) 5:73-81.

Sherman, P.M., et al., "Saturation Mutagenesis of the Plasminogen Activator Inhibitor-1 Reactive Center," *J. Biol. Chem.*(1992) 267(11):7588-7595.

Shore, J.D., et al., "A Fluorescent Probe Study of Plasminogen Activator Inhibitor-1", *J. Biol. Chem.* (1995) 270(10):5395-5398.

Shubeita, H.E., et al., "Mutational and Immunochemical Analysis of Plasminogen Activator Inhibitor-1" *J. Biol. Chem.*, (1990) 265(30): 18379-18385.

Vanderkuur et al., "Growth Hormone-dependent Phosphorylation of Tyrosine 333 and/or 338 of the Growth Hormone Receptor," *J. Biol. Chem.* 270(37):21738-21744.

* cited by examiner

```
         GAATTCCTGCAGCTCAGCAGCCGCCGCCAGAGCAGGACGAACCGCCAATCGCAAGGCACC
    1    ---------+---------+---------+---------+---------+---------+  60
         CTTAAGGACGTCGAGTCGTCGGCGGCGGTCTCGTCCTGCTTGGCGGTTAGCGTTCCGTGG

TCTGAGAACTTCAGGATGCAGATGTCTCCAGCCCTCACCTGCCTAGTCCTGGGCCTGGCC
    61   ---------+---------+---------+---------+---------+---------+ 120
         AGACTCTTGAAGTCCTACGTCTACAGAGGTCGGGAGTGGACGGATCAGGACCCGGACCGG
aa                     M  Q  M  S  P  A  L  T  C  L  V  L  G  L  A   -
                       |Signal Peptide CTTGTCTTTGGTGAAGGGTCTGCTGTGCACCATCCCCCATCCTACGTGGCCCACCTGGCC
    121  ---------+---------+---------+---------+---------+---------+ 180
         GAACAGAAACCACTTCCCAGACGACACGTGGTAGGGGTAGGATGCACCGGGTGGACCGG
aa        L  V  F  G  E  G  S  A |V  H  H  P  P  S  Y  V  A  H  L  A  12
                                   Start Mature Protein
         TCAGACTTCGGGGTGAGGGTGTTTCAGCAGGTGGCGCAGGCCTCCAAGGACCGCAACGTG
    181  ---------+---------+---------+---------+---------+---------+ 240
         AGTCTGAAGCCCCACTCCCACAAAGTCGTCCACCGCGTCCGGAGGTTCCTGGCGTTGCAC
aa         S  D  F  G  V  R  V  F  Q  Q  V  A  Q  A  S  K  D  R  N  V  32

GTTTTCTCACCCTATGGGGTGGCCTCGGTGTTGGCCATGCTCCAGCTGACAACAGGAGGA
    241  ---------+---------+---------+---------+---------+---------+ 300
         CAAAAGAGTGGGATACCCCACCGGAGCCACAACCGGTACGAGGTCGACTGTTGTCCTCCT
aa         V  F  S  P  Y  G  V  A  S  V  L  A  M  L  Q  L  T  T  G  52

GAAACCCAGCAGCAGATTCAAGCAGCTATGGGATTCAAGATTGATGACAAGGGCATGGCC
    301  ---------+---------+---------+---------+---------+---------+ 360
         CTTTGGGTCGTCGTCTAAGTTCGTCGATACCCTAAGTTCTAACTACTGTTCCCGTACCGG
aa         E  T  Q  Q  Q  I  Q  A  A  M  G  F  K  I  D  D  K  G  M  A  72

CCCGCCCTCCGGCATCTGTACAAGGAGCTCATGGGGCCATGGAACAAGGATGAGATCAGC
    361  ---------+---------+---------+---------+---------+---------+ 420
         GGGCGGGAGGCCGTAGACATGTTCCTCGAGTACCCCGGTACCTTGTTCCTACTCTAGTCG
aa         P  A  L  R  H  L  Y  K  E  L  M  G  P  W  N  K  D  E  I  S  92

ACCACAGACGCGATCTTCGTCCAGCGGGATCTGAAGCTGGTCCAGGGCTTCATGCCCCAC
    421  ---------+---------+---------+---------+---------+---------+ 480
         TGGTGTCTGCGCTAGAAGCAGGTCGCCCTAGACTTCGACCAGGTCCCGAAGTACGGGGTG
aa         T  T  D  A  I  F  V  Q  R  D  L  K  L  V  Q  G  F  M  P  H  112
         TTCTTCAGGCTGTTCCGGAGCACGGTCAAGCAAGTGGACTTTTCAGAGGTGGAGAGAGCC
    481  ---------+---------+---------+---------+---------+---------+ 540
         AAGAAGTCCGACAAGGCCTCGTGCCAGTTCGTTCACCTGAAAAGTCTCCACCTCTCTCGG
aa         F  F  R  L  F  R  S  T  V  K  Q  V  D  F  S  E  V  E  R  A  132

AGATTCATCATCAATGACTGGGTGAAGACACACACAAAAGGTATGATCAGCAACTTGCTT
    541  ---------+---------+---------+---------+---------+---------+ 600
         TCTAAGTAGTAGTTACTGACCCACTTCTGTGTGTGTTTTCCATACTAGTCGTTGAACGAA
aa         R  F  I  I  N  D  W  V  K  T  H  T  K  G  M  I  S  N  L  L  152
```

FIG.3A

```
       GGGAAAGGAGCCGTGGACCAGCTGACACGGCTGGTGCTGGTGAATGCCCTCTACTTCAAC
   601 ---------+---------+---------+---------+---------+---------+ 660
       CCCTTTCCTCGGCACCTGGTCGACTGTGCCGACCACGACCACTTACGGGAGATGAAGTTG
aa      G  K  G  A  V  D  Q  L  T  R  L  V  L  V  N  A  L  Y  F  N  172

GGCCAGTGGAAGACTCCCTTCCCCGACTCCAGCACCCACCGCCGCCTCTTCCACAAATCA
   661 ---------+---------+---------+---------+---------+---------+ 720
       CCGGTCACCTTCTGAGGGAAGGGGCTGAGGTCGTGGGTGGCGGCGGAGAAGGTGTTTAGT
aa      G  Q  W  K  T  P  F  P  D  S  S  T  H  R  R  L  F  H  K  S  192

GACGGCAGCACTGTCTCTGTGCCCATGATGGCTCAGACCAACAAGTTCAACTATACTGAG
   721 ---------+---------+---------+---------+---------+---------+ 780
       CTGCCGTCGTGACAGAGACACGGGTACTACCGAGTCTGGTTGTTCAAGTTGATATGACTC
aa      D  G  S  T  V  S  V  P  M  M  A  Q  T  N  K  F  N  Y  T  E  212

TTCACCACGCCCGATGGCCATTACTACGACATCCTGGAACTGCCCTACCACGGGGACACC
   781 ---------+---------+---------+---------+---------+---------+ 840
       AAGTGGTGCGGGCTACCGGTAATGATGCTGTAGGACCTTGACGGGATGGTGCCCCTGTGG
aa      F  T  T  P  D  G  H  Y  Y  D  I  L  E  L  P  Y  H  G  D  T  232

CTCAGCATGTTCATTGCTGCCCCTTATGAAAAAGAGGTGCCTCTCTCTGCCCTCACCAAC
   841 ---------+---------+---------+---------+---------+---------+ 900
       GAGTCGTACAAGTAACGACGGGGAATACTTTTTCTCCACGGAGAGAGACGGGAGTGGTTG
aa      L  S  M  F  I  A  A  P  Y  E  K  E  V  P  L  S  A  L  T  N  252

ATTCTGAGTGCCCAGCTCATCAGCCACTGGAAAGGCAACATGACCAGGCTGCCCCGCCTC
   901 ---------+---------+---------+---------+---------+---------+ 960
       TAAGACTCACGGGTCGAGTAGTCGGTGACCTTTCCGTTGTACTGGTCCGACGGGGCGGAG
aa      I  L  S  A  Q  L  I  S  H  W  K  G  N  M  T  R  L  P  R  L  272

CTGGTTCTGCCCAAGTTCTCCCTGGAGACTGAAGTCGACCTCAGGAAGCCCCTAGAGAAC
   961 ---------+---------+---------+---------+---------+---------+ 1020
       GACCAAGACGGGTTCAAGAGGGACCTCTGACTTCAGCTGGAGTCCTTCGGGGATCTCTTG
aa      L  V  L  P  K  F  S  L  E  T  E  V  D  L  R  K  P  L  E  N  292

CTGGGAATGACCGACATGTTCAGACAGTTTCAGGCTGACTTCACGAGTCTTTCAGACCAA
  1021 ---------+---------+---------+---------+---------+---------+ 1080
       GACCCTTACTGGCTGTACAAGTCTGTCAAAGTCCGACTGAAGTGCTCAGAAAGTCTGGTT
aa      L  G  M  T  D  M  F  R  Q  F  Q  A  D  F  T  S  L  S  D  Q  312

GAGCCTCTCCACGTCGCGCAGGCGCTGCAGAAAGTGAAGATCGAGGTGAACGAGAGTGGC
  1081 ---------+---------+---------+---------+---------+---------+ 1140
       CTCGGAGAGGTGCAGCGCGTCCGCGACGTCTTTCACTTCTAGCTCCACTTGCTCTCACCG
aa      E  P  L  H  V  A  Q  A  L  Q  K  V  K  I  E  V  N  E  S  G  332

ACGGTGGCCTCCTCATCCACAGCTGTCATAGTCTCAGCCCGCATGGCCCCCGAGGAGATC
  1141 ---------+---------+---------+---------+---------+---------+ 1200
       TGCCACCGGAGGAGTAGGTGTCGACAGTATCAGAGTCGGGCGTACCGGGGGCTCCTCTAG
aa      T  V  A  S  S  S  T  A  V  I  V  S  A  R  M  A  P  E  E  I  352

ATCATGGACAGACCCTTCCTCTTTGTGGTCCGGCACAACCCCACAGGAACAGTCCTTTTC
  1201 ---------+---------+---------+---------+---------+---------+ 1260
       TAGTACCTGTCTGGGAAGGAGAAACACCAGGCCGTGTTGGGGTGTCCTTGTCAGGAAAAG
aa      I  M  D  R  P  F  L  F  V  V  R  H  N  P  T  G  T  V  L  F  372
```

FIG.3B

```
             ATGGGCCAAGTGATGGAACCCTGACCCTGGGGAAAGACGCCTTCATCTGGGACAAAACTG
     1261    ---------+---------+---------+---------+---------+---------+ 1320
             TACCCGGTTCACTACCTTGGGACTGGGACCCCTTTCTGCGGAAGTAGACCCTGTTTTGAC
   a  a         M   G   Q   V   M   E   P   *  379

GAGATGCATCGGGAAAGAAGAAACTCCGAAGAAAAGAATTTTAGTGTTAATGACTCTTTC
     1321    ---------+---------+---------+---------+---------+---------+ 1380
             CTCTACGTAGCCCTTTCTTCTTTGAGGCTTCTTTTCTTAAAATCACAATTACTGAGAAAG

TGAAGGAAGAGAAGACATTTGCCTTTTGTTAAAAGATGGTAAACCAGATCTGTCTCCAAG
     1381    ---------+---------+---------+---------+---------+---------+ 1440
             ACTTCCTTCTCTTCTGTAAACGGAAAACAATTTTCTACCATTTGGTCTAGACAGAGGTTC

ACCTTGGCCTCTCCTTGGAGGACCTTTAGGTCAAACTCCCTAGTCTCCACCTGAGACCCT
     1441    ---------+---------+---------+---------+---------+---------+ 1500
             TGGAACCGGAGAGGAACCTCCTGGAAATCCAGTTTGAGGGATCAGAGGTGGACTCTGGGA

GGGAGAGAAGTTTGAAGCACAACTCCCTTAAGGTCTCCAAACCAGACGGTGACGCCTGCG
     1501    ---------+---------+---------+---------+---------+---------+ 1560
             CCCTCTCTTCAAACTTCGTGTTGAGGGAATTCCAGAGGTTTGGTCTGCCACTGCGGACGC

GGACCATCTGGGGCACCTGCTTCCACCCGTCTCTCTGCCCACTCGGGTCTGCAGACCTGG
     1561    ---------+---------+---------+---------+---------+---------+ 1620
             CCTGGTAGACCCCGTGGACGAAGGTGGGCAGAGAGACGGGTGAGCCCAGACGTCTGGACC

TTCCCACTGAGGCCCTTTGCAGGATGGAACTACGGGGCTTACAGGAGCTTTTGTGTGCCT
     1621    ---------+---------+---------+---------+---------+---------+ 1680
             AAGGGTGACTCCGGGAAACGTCCTACCTTGATGCCCCGAATGTCCTCGAAAACACACGGA

GGTAGAAACTATTTCTGTTCCAGTCACATTGCCATCACTCTTGTACTGCCTGCCACCGCG
     1681    ---------+---------+---------+---------+---------+---------+ 1740
             CCATCTTTGATAAAGACAAGGTCAGTGTAACGGTAGTGAGAACATGACGGACGGTGGCGC

GAGGAGGCTGGTGACAGGCCAAAGGCCAGTGGAAGAAACACCCTTTCATCTCAGAGTCCA
     1741    ---------+---------+---------+---------+---------+---------+ 1800
             CTCCTCCGACCACTGTCCGGTTTCCGGTCACCTTCTTTGTGGGAAAGTAGAGTCTCAGGT

CTGTGGCACTGGCCACCCCTCCCCAGTACAGGGGTGCTGCAGGTGGCAGAGTGAATGTCC
     1801    ---------+---------+---------+---------+---------+---------+ 1860
             GACACCGTGACCGGTGGGGAGGGGTCATGTCCCCACGACGTCCACCGTCTCACTTACAGG

CCCATCATGTGGCCCAACTCTCCTGGCCTGGCCATCTCCCTCCCCAGAAACAGTGTGCAT
     1861    ---------+---------+---------+---------+---------+---------+ 1920
             GGGTAGTACACCGGGTTGAGAGGACCGGACCGGTAGGGGAGGGGTCTTTGTCACACGTA

GGGTTATTTTGGAGTGTAGGTGACTTGTTTACTCATTGAAGCAGATTTCTGCTTCCTTTT
     1921    ---------+---------+---------+---------+---------+---------+ 1980
             CCCAATAAAACCTCACATCCACTGAACAAATGAGTAACTTCGTCTAAAGACGAAGGAAAA

ATTTTTATAGGAATAGAGGAAGAAATGTCAGATGCGTGCCCAGCTCTTCACCCCCCAATC
     1981    ---------+---------+---------+---------+---------+---------+ 2040
             TAAAAATATCCTTATCTCCTTCTTTACAGTCTACGCACGGGTCGAGAAGTGGGGGGTTAG
```

FIG.3C

```
         TCTTGGTGGGGAGGGGTGTACCTAAATATTTATCATATCCTTGCCCTTGAGTGCTTGTTA
2041     ------------------+---------+---------+---------+---------+ 2100
         AGAACCACCCCTCCCCACATGGATTTATAAATAGTATAGGAACGGGAACTCACGAACAAT

GAGAGAAAGAGAACTACTAAGGAAAATAATATTATTTAAACTCGCTCCTAGTGTTTCTTT
2101     ---------+---------+---------+---------+---------+---------+ 2160
         CTCTCTTTCTCTTGATGATTCCTTTTATTATAATAAATTTGAGCGAGGATCACAAAGAAA

GTGGTCTGTGTCACCGTATCTCAGGAAGTCCAGCCACTTGACTGGCACACACCCCTCCGG
2161     ---------+---------+---------+---------+---------+---------+ 2220
         CACCAGACACAGTGGCATAGAGTCCTTCAGGTCGGTGAACTGACCGTGTGTGGGGAGGCC

ACATCCAGCGTGACGGAGCCCACACTGCCACCTTGTGGCCGCCTGAGACCCTCGCGCCCC
2221     ---------+---------+---------+---------+---------+---------+ 2280
         TGTAGGTCGCACTGCCTCGGGTGTGACGGTGGAACACCGGCGGACTCTGGGAGCGCGGGG

CCGCGCCCCCGCGCCCCTCTTTTCCCCTTGATGGAAATTGACCATACAATTTCATCCT
2281     ---------+---------+---------+---------+---------+---------+ 2340
         GGCGCGGGGGGCGCGGGGAGAAAAAGGGGAACTACCTTTAACTGGTATGTTAAAGTAGGA

CCTTCAGGGGATCAAAAGGACGGAGTGGGGGGACAGAGACTCAGATGAGGACAGAGTGGT
2341     ---------+---------+---------+---------+---------+---------+ 2400
         GGAAGTCCCCTAGTTTTCCTGCCTCACCCCCCTGTCTCTGAGTCTACTCCTGTCTCACCA

TTCCAATGTGTTCAATAGATTTAGGAGCAGAAATGCAAGGGGCTGCATGACCTACCAGGA
2401     ---------+---------+---------+---------+---------+---------+ 2460
         AAGGTTACACAAGTTATCTAAATCCTCGTCTTTACGTTCCCCGACGTACTGGATGGTCCT

CAGAACTTTCCCCAATTACAGGGTGACTCACAGCCGCATTGGTGACTCACTTCAATGTGT
2461     ---------+---------+---------+---------+---------+---------+ 2520
         GTCTTGAAAGGGGTTAATGTCCCACTGAGTGTCGGCGTAACCACTGAGTGAAGTTACACA

CATTTCCGGCTGCTGTGTGTGAGCAGTGGACACGTGAGGGGGGGGTGGGTGAGAGAGACA
2521     ---------+---------+---------+---------+---------+---------+ 2580
         GTAAAGGCCGACGACACACACTCGTCACCTGTGCACTCCCCCCCCACCCACTCTCTCTGT

GGCAGCTCGGATTCAACTACCTTAGATAATATTTCTGAAAACCTACCAGCCAGAGGGTAG
2581     ---------+---------+---------+---------+---------+---------+ 2640
         CCGTCGAGCCTAAGTTGATGGAATCTATTATAAAGACTTTTGGATGGTCGGTCTCCCATC

GGCACAAAGATGGATGTAATGCACTTTGGGAGGCCAAGGCGGGAGGATTGCTTGAGCCCA
2641     ---------+---------+---------+---------+---------+---------+ 2700
         CCGTGTTTCTACCTACATTACGTGAAACCCTCCGGTTCCGCCCTCCTAACGAACTCGGGT

GGAGTTCAAGACCAGCCTGGGCAACATACCAAGACCCCGTCTCTTTAAAAATATATATA
2701     ---------+---------+---------+---------+---------+---------+ 2760
         CCTCAAGTTCTGGTCGGACCCGTTGTATGGTTCTGGGGGCAGAGAAATTTTATATATAT

TTTTAAATATACTTAAATATATATTTCTAATATCTTTAAATATATATATATATTTTAAAG
2761     ---------+---------+---------+---------+---------+---------+ 2820
         AAAATTTATATGAATTTATATATAAAGATTATAGAAATTTATATATATATATAAAATTTC

ACCAATTTATGGGAGAATTGCACACAGATGTGAAATGAATGTAATCTAATAGAAGC
2821     ---------+---------+---------+---------+---------+------ 2876
         TGGTTAAATACCCTCTTAACGTGTGTCTACACTTTACTTACATTAGATTATCTTCG
```

FIG.3D

```
                                        MQMSPALTCLVLGLALVFGEGSA
                                        ─────────────────────────
                                              Signal peptide
        10        20        30        40        50        60
         |         |         |         |         |         |
    VHHPPSYVAHLASDFGVRVFQQVAQASKDRNVVFSPYGVASVLAMLQLTTGGETQQQIQA 70        80        90       100       110       120
         |         |         |         |         |         |
    AMGFKIDDKGMAPALRHLYKELMGPWNKDEISTTDAIFVQRDLKLVQGFMPHFFRLFRST 130       140       150       160       170       180
         |         |         |         |         |         |
    VKQVDFSEVERARFIINDWVKTHTKGMISNLLGKGAVDQLTRLVLVNALYFNGQWKTPFP 190       200       210       220       230       240
         |         |         |         |         |         |
    DSSTHRRLFHKSDGSTVSVPMMAQTNKFNYTEFTTPDGHYYDILELPYHGDTLSMFIAAP 250       260       270       280       290       300
         |         |         |         |         |         |
    YEKEVPLSALTNILSAQLISHWKGNMTRLPRLLVLPKFSLETEVDLRKPLENLGMTDMFR 310       320       330       340       350       360
         |         |         |         |         |         |
    QFQADFTSLSDQEPLHVAQALQKVKIEVNESGTVASSSTAVIVSARMAPEEIIMDRPFLF
                              ************|**|******
       370                               P4  P1
         |
    VVRHNPTGTVLFMGQVMEP
```

FIG.4A

```
          10        20        30        40        50        60
           |         |         |         |         |         |
VHHPPSYVAHLASDFGVRVFQQVAQASKDRNVVFSPYGVASVLAMLQLTTGGETQQQIQA 70        80        90       100       110       120
           |         |         |         |         |         |
AMGFKIDDKGMAPALRHLYKELMGPWNKDEISTTDAIFVQRDLKLVQGFMPHFFRLFRST 130       140       150       160       170       180
           |         |         |         |         |         |
VKQVDFSEVERARFIINDWVKTHTKGMISNLLGKGAVDQLTRLVLVNALYFNGQWKTPFP 190       200       210       220       230       240
           |         |         |         |         |         |
DSSTHRRLFHKSDGSTVSVPMMAQTNKFNYTEFTTPDGHYYDILELPYHGDTLSMFIAAP 250       260       270       280       290       300
           |         |         |         |         |         |
YEKEVPLSALTNILSAQLISHWKGNMTRLPRLLVLPKFSLETEVDLRKPLENLGMTDMFR 310       320       330       340       350       360
           |         |         |         |         |         |
QFQADFTSLSDQEPLHVAQALQKVKIEVNESGTVASSSTAVIVSARMAPEEIIMDRPFLF

370
           |
VVRHNPTGTVLFMGQVMEP
```

FIG.4B

MUTANT PLASMINOGEN ACTIVATOR-INHIBITOR TYPE 1 (PAI-1) AND USES THEREOF

CROSS REFERENCE TO RELATED APPLICATIONS

This application is a divisional application of U.S. Ser. No. 09/324,494, filed on Jun. 2, 1999, now U.S. Pat. No. 6,489,143 which is a continuation of U.S. Ser. No. 08/840,204, filed Apr. 11, 1997, now U.S. Pat. No. 6,103,498, which claims benefit to U.S. provisional application No. 60/015,299, filed on Apr. 12, 1996, which are incorporated in their entirety by reference.

STATEMENT AS TO THE RIGHTS TO INVENTIONS MADE UNDER FEDERALLY SPONSORED RESEARCH AND DEVELOPMENT

The present invention was made with U.S Government support under Grant No. HL 55374, awarded by the National Institutes of Health. The government has certain rights in this invention.

BACKGROUND OF THE INVENTION

1. Field of the Invention

The invention in the field of biochemistry and medicine relates to compositions comprising mutant proteins of plasminogen activator inhibitor-type 1 (PAI-1) which have the capacity to inhibit the enzyme elastase and to inhibit vitronectin (Vn)-dependent migration of cells. This invention also relates to uses of these proteins for the treatment of diseases and disorders associated with elastase activity or in which migration and migration-driven proliferation of cells have pathophysiologic consequences.

DESCRIPTION OF THE BACKGROUND ART

1. Plasmiogen Activators

Plasminogen activators (PAs) are specific serine proteinases that activate the proenzyme plasminogen, by cleavage of a single Arg-Val peptide bond, to the enzyme plasmin (Saksela O, *Biochim Biophys Acta* (1985) 823:35-65). Two plasminogen activators are found in mammals, tissue-type PA (tPA) and urokinase-type PA (uPA) (Saksela O et al, *Annu Rev Cell Biol* (1988) 4:93-126). These enzymes are thought to influence critically many biological processes, including vascular fibrinolysis (Bachmann E, *Thromb Haemost* (1987) 10:227-265), ovulation (Hsuch A J W et al, In: Haseltine F P et al, eds, *Meiotic Inhibition: Molecular Control of Meiosis* New York: Liss 1988:227-258), inflammation (Pollanen J et al., *Adv Cancer Res* (1991) 57:273-328), tumor metastasis (Dano K et al., *Adv Cancer Res* (1985) 44:139-266), angiogenesis (Moscatelli D et al., *Biochim Biophys Acta* (1988) 948:67-85), and tissue remodeling (Saksela, supra).

The regulation of PAs is a complex process controlled on many levels. The synthesis and release of PAs are governed by various hormones, growth factors, and cytokines (Saksela, supra; Dano et al., supra). Following secretion, PA activity can be regulated both positively and negatively by a number of specific protein-protein interactions. Activity can be enhanced or concentrated by interactions with fibrin (Hoylaerts M et al., *J Biol Chem* (1982) 257:2912-2919), the uPA receptor (uPAR) (Ellis V et al., *Semin Thromb Hemost* (1991) 17:194-200), the tPA receptor (tPAR) (Hajjar K A et al., *J Biol Chem* (1990) 265:2908-2916), or the plasminogen receptor (Plow E F et al., *Thromb Haemost* (1991) 66:32-36).

PA activity can be downregulated by specific PA inhibitors (PAIs) (Lawrence, D. A et al., In: *Molecular Biology of Thrombosis and Hemostasis*, Roberts, H. R. et al., (Eds.), Marcel Dekker Inc., New York, chapter 25, pp. 517-543 (1995)). In addition, PA activity is dependent on its location or microenvironment and may be different in solution (e.g., circulating blood) as compared to a solid-phase (e.g., on a cell surface or in the extracellular matrix (ECM)). The overall activity of the PA system is determined by the interactions among these various elements and the balance between the opposing activities of enzymes and inhibitors.

The PAIs have become recognized as critical regulators of the PA system. The identification of an efficient inhibitor of tPA in endothelial cells (ECs) was first reported in 1983 (Loskutoff D J et al., *Proc Natl Acad Sci USA* (1983) 80:2956-2960). Four kinetically relevant PAIs are currently recognized: PAI type 1 (PAI-1), initially described as the endothelial cell PAI; PAI type 2 (PAI-2), also referred to as placental PAI; PAI type 3 (PAI-3), also known as activated protein C (APC) inhibitor and proteinase nexin 1 (PN-1), also called glia-derived neurite-promoting factor. The present invention is directed in particular to PAI-1.

2. Other Serine Proteinases

Elastase is a serine proteinase released by activated neutrophils and macrophages and monocytes. During inflammatory responses, neutrophils are activated and release elastase leading to tissue destruction through proteolysis. In the lung, elastase degrades elastic tissues and leads to emphysema. Elastase is also a compounding factor in cystic fibrosis (CF) and in both adult and infant acute respiratory distress syndrome (ARDS). Elastase has also been implicated in TNF-mediated inflammation (Massague, J. et al., *Annu. Rev. Biochem.* 62:515-541 (1993) and HIV infection (Bristow, C. L. et al., *International Immunol* 7:239-249 (1995)).

Elastase has a broader spectrum of reactivity than plasminogen activators each of which acts preferentially on a precursor substrate to activate it.

The natural defense to elastase is a protein called α1 anti-trypsin ($\alpha_1$AT) or α1 proteinase inhibitor (($\alpha_1$PI). Patients who are deficient in $\alpha_1$AT are prone to emphysema, especially smokers. Furthermore, smoking provokes inflammation. In such α1AT deficiencies, the enzyme is present (CRM$^+$) but is functionally impaired. In addition, even in individuals with normal enzyme, smoking directly inactivates $\alpha_1$AT. Therefore, an improved inhibitor of elastase would be highly desirable for the prevention of emphysema in susceptible subjects or for reversal of the pathophysiological process leading to this an other related diseases.

3. Serpins

The major PA's belong to the serine proteinase inhibitor (serpin) gene superfamily which includes many proteinase inhibitors in blood as well as other proteins with unrelated or unknown function (Huber R et al., *Biochemistry* (1989) 28:8951-8966). The serpins share a common tertiary structure and have evolved from a common ancestor. Serpins regulate many processes including coagulation, fibrinolysis, complement activation, ovulation, angiogenesis, inflammation, neoplasia, viral pathogenesis and allergic reactivity.

Current models of serpin structure are based on x-ray crystallographic studies of one member of the family, $\alpha_1$AT (reviewed in Huber et al., supra). An interesting feature of the structure of a modified form of α1AT, cleaved in its reactive center (Loeberrmann H et al.; J Mol Biol (1984) 177:531-557), is that the two amino acid residues that normally constitute the reactive center (Met-Ser bond), are found on opposite ends of the molecule, separated by almost 70 Å. This is shown for PAI-1 in FIG. 2 and can be compared to the active structure modeled in FIG. 1. Relaxation of a strained configuration takes place upon cleavage of the reactive-center peptide bond, rather than a major rearrangement of the inhibitor structure. In this model, the reactive center is part of an exposed loop, also called the strained loop. Upon cleavage, this loop moves or "snaps back," becoming one of several central strands in a major β sheet structure. This transformation is accompanied by a large increase in thermal stability, presumably as a result of the reconstitution of the six-stranded β sheet A.

Synthetic peptides homologous to the reactive-center loops of serpins, when added in trans, incorporate into their respective molecules, presumably as a central strand of the major β sheet structure and increase the thermal stability of the molecule like that observed after cleavage at the reactive center. This structural change converts the serpin from an inhibitor to a substrate for its target proteinase (Carrell RW et al., Nature (1991) 353:576-578; Bjork I et al., *J Biol Chem* (1992) 267:1976-1982).

Serpins act as suicide inhibitors, reacting only once with their target proteinase to form a sodium dodecyl sulfate (SDS)-stable complex. These complexes can dissociate to yield free active enzyme together with a cleaved inhibitor similar to that seen in the α1AT crystal structure (Carrell R W et al., In: Barrett A J, et al. eds., *Proteinase Inhibitors*. Amsterdarn: Elsevier Science Publishers 1986:403-420) and modeled in FIGS. 1 and 2 for PAI-1.

Serpins interact with their target proteinase by providing a "bait" amino acid residue in the reactive center which is thought to mimic the normal substrate of the enzyme and to associate via its side-chain atoms with the specificity crevice, or Si site, of the enzyme (Huber et al, supra.; Carrell et al., supra; Shubeita H E et at., *J Biol Chem* (1990) 265: 18379-18385; York J D et al., *J. Biol Chem* (1991) 266: 8495-8500; Sherman P M et al., *J Biol Chem* (1992) 267:7588-7595). The bait amino acid is designated the P1 residue. The amino acids toward the N-terminal side of the scissile reactive-center bond are labeled in order P1, P2, P3, etc., and the amino acids on the carboxyl side are labeled P1', P2', etc. (Carrell et al., 1986, supra). The amino acid residues in the reactive center ioop of PAI-1 (residues 332-351) are shown below labeled according to the foregoing naming convention. Also noted are the numerical positions in the full sequence of mature PAI-1 (SEQ ID NO:11):

The complex between serpins and their target proteinases is thought to be covalently linked via an ester bond between the active-site serine residue of the proteinase and the new C-terminal end of the P1 residue, forming an acyl-enzyme complex (Lawrence D A et al., *J Biol Chem* (1995)279: 25309-25312). The association between inhibitor and proteinase also involves regions other than the P1 residue of the serpin and other than the catalytic site of the proteinase, based on the characterization of two recombinant PA mutants in which six or seven amino acids were deleted from the catalytic domains. These mutant PAs were almost completely refractory to inhibition by PAI-1, suggesting that the residues distant from the active site are nevertheless critical for the interaction with PAI-1 (Madison E L et al., *Nature* (1989) 339:721-724; Adams D S et al., *J Biol Chem* (1991) 266:8476-8482).

4. Plasminogen Activator Inhibitor Type 1 (PAI-1)

PAI-1 (see Table 1) is considered one of the principal regulators of the PA system. It is a single chain glycoprotein with a molecular weight of 50 kDa (Van Mourik J A et al., *J Biol Chem* (1984) 259: 14914-14921) and is the most efficient inhibitor known of the single- and two-chain forms of tPA and of uPA (Table 1) (Lawrence D et al., Eur J Biochem (1989) 186:523-533). PAI-1 also inhibits plasmin and trypsin (Hekman C M et al., Biochemistry (1988) 27:2911-2918) and also inhibits thrombin and activated protein C, though with much lower efficiency.

TABLE 1

SUMMARY OF CHARACTERISTICS OF PAI-1

| Other Names | Sources | 2nd Order Rate Constants ($M^{-1}$ $s^{-1}$) | Other ligands |
| --- | --- | --- | --- |
| Endothelial PAI | In vivo | uPA $9.0 \times 10^6$ | Vitronectin |
| Platelet PAI | platelets | tctPA $2.7 \times 10^7$ | Heparin |
| Fast-acting PAI | smooth muscle | sctPA $4.5 \times 10^6$ | Fibrin |
| β-Migrating PAI | LPS-activated endothelium In vitro: many cells types | APC $1.1 \times 10^4$ Plasmin $6.6 \times 10^5$ Trypsin $7.0 \times 10^5$ Thrombin $10^3 - 2 \times 10^5$ | |

Abbreviations: LPS, lipopolysaccharide: sctPA. single-chain tPA: tctPA. two-chain tPA: APC. activated protein C PAI-1 is present in plasma at very low concentrations, ranging from 0 to 60 ng/ml (average of about 20 ng/ml or 0.5 nM) (Declerck P J et al., *Blood* (1988) 71:220-225) and a reported half-life of about 6-7 minutes (Vaughan D E et al., *Circ Res* (1990) 67:1281-1286). In a study comparing the clearance of two distinct forms of PAI-1 (active and latent; see below), the active form was cleared biphasically (half-lives of 6 and 25 minutes), whereas latent PAI-1 was cleared with a half-life of only 1.7 minutes (Mayer E J et al., Blood (1990) 76: 1514-1520).

PAI-1 is present in platelets and other tissues and is produced by many cell types in culture (Erickson L A et al., *J Clin Invest* (1984) 74:1465-1472; Sawdey M S et al., *J Clin Invest* (1991) 88:1346-1353, Krishnamurti C et al., *Semin Thromb Hemost* (1992) 18:67-80). In vivo, the primary extravascular source of PAI-1 appears to be vascular

```
332 333 334 335 336 337 338 339 340 341 342 343 344 345 346 347 348 349 350 351

P15 P14 P13 P12 P11 P10 P9  P8  P7  P6  P5  P4  P3  P2  P1  P1' P2' P3' P4' P5'

Gly Thr Val Ala Ser Ser Ser Thr Ala Val Ile Val Ser Ala Arg Met Ala Pro Glu Glu
``` smooth muscle cells (SMCs) (Loskutoff D J, *Fibrinolysis* (1991) 5:197-206). During endotoxemia or other pathological conditions, ECs become a major site of PAI-1 synthesis (Pyke C et al., *Cancer Res* (1991) 51:4067-4071; Schneiderman J et al., *Proc Natl Acad Sci USA* (1992) 89:6998-7002; Keeton M et al., *Am J Pathol* (1993) 142:59-70).

Plasma PAI-1 is present as a complex with vitronectin (Vn) or S protein (Declerck P J et al., *J Biol Chem* (1988) 263: 15454-15461). PAI-1 is also associated with Vn in the ECM in culture and may be involved in maintaining the integrity of the cell substratum in vivo (Mimuro J et al., *Blood* (1987) 70:721-728; Mimuro J et al., *J Biol Chem* (1989) 264:5058-5063).

The major source of plasma PAI-1 is not known but is likely to be vascular SMCs, though a contribution from the platelet pool cannot be excluded. PAI-1 functions efficiently in solution and when bound to surfaces ("solid phase"), and it is likely that PAI-1 regulates fibrinolysis in both environments.

(a) PAI-1 Protein Structure and Function (See FIGS. 1-4)

PAI-1 cDNA encodes a protein of 402 amino acids that includes a typical secretion signal sequence (Ny et al., supra; Ginsburg et al., 1986, supra). Mature human PAI-1 isolated from cell culture is composed of two variants of 381 and 379 amino acids in approximately equal proportions. These two forms, likely arising from alternative cleavage of the secretion signal sequence, provide proteins with overlapping amino-terminal sequences of (SEQ ID NO:12) Ser-Ala-Val-His-His and (SEQ ID NO:13) Val-His-His-Pro-Pro (portion of SEQ ID NO:2 and 3) (Lawrence et al., 1989, supra). This latter sequence is generally referred to as mature PAI-1.

PAI-1 is a glycoprotein with three potential N-linked glycosylation sites containing between 15 and 20% carbohydrate (Van Mourik J A et al., supra). Mature PAI-1 contains no cysteine residues, facilitating efficient expression and isolation of recombinant PAI-1 from *E. coli*. PAI-1 produced in *E. coli*, although nonglycosylated, is functionally very similar to native PAI-1. Recombinant PAI-1 can be isolated from *E. coli* in an inherently active form (see below), which contrasts with PAI-1 purified from mammalian cell culture (Lawrence et al., 1989, supra; Hekman et al., 1988, supra).

(b) Active and Latent Conformation

PAI-1 exists in an active form as it is produced by cells and secreted into the culture medium and an inactive or latent form that accumulates in the culture medium over time (Hekman C M et al., *J Biol Chem* (1985) 260:11581-11587; Levin E G et al, *Blood* (1987) 70:1090-1098). The active form spontaneously converts to the latent form with a half-life of about 1 h at 37° C. (Lawrence et al., supra; Hekman et al., supra; Levin E G et al, 1987, supra).

The latent form can be converted into the active form by treatment with denaturants, negatively charged phospholipids or Vn (Lambers et al, supra, Hekman et al, supra; Wun T-C et al, *J Biol Chem* (1989) 264:7862-7868). Latent PAI-1 infused into rabbits became reactivated in vivo by an unknown mechanism. The reversible interconversion between the active and latent structures, presumably due to a conformational change, is a unique feature of PAI-1 as compared to other serpins. The latent form appears to be more energetically favored.

The three-dimensional structure of the latent form of PAI-1 has been solved. In this structure the entire N-terminal side of the reactive center loop is inserted as the central strand into β sheet A (FIG. 2) (Mottonen et al., supra) which explains the increased stability (Lawrence, D. A. et al., *Biochemistry* 33:3643-3648 (1994)) as well as the lack of inhibitory activity. The structure of active PAI-1 is still unknown. It has been proposed that the reactive center in active PAI-1 is exposed as a surface loop, in contrast to its position in the latent structure (FIG. 1).

(c) The Reactive-Center Loop (RCL)

The RCL region of PAI-1 has been the subject of extensive mutational analysis which demonstrated the importance of the P1 bait residue in inhibitor function, whereas the surrounding amino acids play a less critical role. Random mutagenesis of the P3, P2, and P1 residues and the P1 and P1' residues, respectively, clearly demonstrated that either arginine or lysine at P1 is essential for PAI-1 to function as an effective inhibitor of uPA (York et al., 1991, supra; Sherman et al., 1992, supra). Residues surrounding P1 can modulate PAI-1 inhibitor activity by up to two orders of magnitude and can alter target proteinase specificity. The P1' site is surprisingly tolerant of amino acid substitutions with the exception of proline which caused almost total loss of function. When an 18 amino acid segment of PAI1 encompassing most of the RCL was replaced with the same region from PAI-2, antithrombin III, or a serpin consensus sequence, most of the requirements for PAI-1 specificity (apart from the P1 residue), were found to lie outside the RCL sequence. All three chimeras remained efficient inhibitors of tPA and uPA, and the antithrombin III chimera was not a significantly improved inhibitor of thrombin. Furthermore, the specific sequence of the RCL, the region inserted into β sheet A in the latent PAI-1 structure (FIG. 1, see above), was not critical for the conversion between the active and latent conformations of PAI-1. Hence, loop insertion depends more on the flexibility of β sheet A than on the specific amino acid residues in the loop. Finally, binding to Vn was not affected by these substitutions in the RCL. The P4' and P5' residues on the C-terminal side of the reactive-center bond have also been replaced pith only a small effect on PAI-1 activity.

(d) Interactions with Vitronectin (Vn)

The adhesive glycoprotein Vn is a 72 kDa glycoprotein present in plasma at micromolar concentrations and associated with many tissues. Like PAI-1, Vn can exist in multiple conformational states. Vn is involved in a wide variety of physiological responses, including cell adhesion, complement activation, thrombosis, and plasma clearance of proteinase-inhibitor complexes (Tomasini, B. R. et al. (1991) *Prog. Hemost. Thromb.* 10, 269-305).

PAI-1 in plasma or in the subcellular matrix is stabilized by Vn. Vn-bound PAI-1 in solution is approximately twice as stable as unbound PAI-1. On ECM the half-life of PAI-1 can be >24 h (Mimuro et al., supra). Most of the PAI-1 found in platelets appears to be latent, although this point is controversial (Lang I M et al., *Blood* (1992) 80:2269-2274). Platelets contain Vn (Preissner K T et al., *Blood* (1989) 74: 1989-1996), which could act to reactivate latent platelet PAI-1 (Wun et al., supra). Platelet PAI-1 may be a major factor in the resistance of platelet-rich thrombi to thrombolysis (Fay WP et al., *Blood* (1994) 84:351-356). Consistent with this, anti-PAI-1 antibodies enhance clot lysis when contacted with platelet-rich thrombi in vitro (Levi M et al., *Circulation* (1992) 85:305-312; Braaten J V et al., *Blood* (1993) 81:12901299).

Vn is thought to localize PAI-1 to the ECM where it regulates local proteolytic activity (Mimuro et al, 1987, supra). Views concerning the interaction of PAI-1 with Vn are controversial probably due to the conformational variability of both proteins. The controversy is directed to both the nature and affinity of binding of these two molecules (Sigurdardottir O et al., *Biochim Biophys Acta* (1990) 1035:

56-61; Kost C et al., *J Biol Chem* (1992) 267:12098-12105; Seiffert D et al., *Biochim Biophys Acta* (1991) 1078:23-30; Salonen E -M et al., *J Biol Chem* (1989) 264:6339-6343). Controversy also surrounds the Vn binding site for PAI-1, which has been localized to the somatomedin B domain at the N-terminus (Seiffert D et al., *J Biol Chem* (1991) 266:2824-2830) and to the C terminus of Vn between residues 348 and 370 (Kost et al, supra). Some of these conflicts may be explained by differences in affinity of binding of the active vs. latent form of PAI-1 with Vn and/or by differences in the relative abundance of PAI-1 conformers in various PAI-1 preparations.

Recent studies of the serpin mechanism of inhibition indicate that it follows a multi-step process that requires an exposed RCL (Shore, J. D. et al, (1994) *J. Biol. Chem.* 270, 5395-5398; Lawrence, D. A. et al., (1995) *J Biol. Chem.* 270, 25309-25312; Fa, M. et al., (1995) *Biochem.* 34:13833-13840; Wilczynska, M. et al., (1995) *J. Biol. Chem.* 270: 29652-29655). Upon association with a target proteinase the serpin RCL is cleaved at its $P_1$-$P_1$, bond and this is followed by a rapid insertion of the RCL into β-sheet A yielding the stable serpin-proteinase complex. As shown by the present inventors (see Examples) a PAI-1 Vn binding epitope on the edge of β-sheet A is sensitive to this conformational change in β-sheet A, as well as to similar changes associated with conversion of PAI-1 to the latent form or cleavage in the RCL by a non-target proteinase. This sensitivity may provide a way to ensure the expression of PAI-1 activity at specific sites of action. For example, Vn is thought to localize PAI-1 to the ECM where it regulates local proteolytic activity (Mimuro et al, supra). In this situation it may be beneficial to permit only functionally active PAI-1 to bind to Vn. On a cell surface an inactive ligand it can be internalized and degrades. However, this type of regulation may not be as efficient on the less dynamic ECM. Therefore, to prevent Vn from becoming saturated with inactive forms of inhibitor, a system may have evolved that is sensitive to the conformational state of PAI-1, which is closely linked to its activity state.

In addition to stabilizing active PAI-1, Vn alters PAI-1 specificity, converting it to an efficient inhibitor of thrombin (Ehrlich et al, supra; Keijer, J. et al., *Blood* (1991) 78:1254-1261). Vn-bound PAI-1 has a 270-fold greater rate constant toward thrombin than does free PAI-1, dependent upon the source of the Vn. Although all forms of Vn can bind PAI-1, only Vn isolated under physiological conditions is able to stimulate PAI-1 to inhibit thrombin (Naski, M. C. et al., *J Biol Chem* (1993) 268:12367-12372): Vn also enhances the clearance of PAI-1-thrombin complexes by the low density lipoprotein receptor-related protein (LRP) (Stefansson, S. et al., (1996) *J Biol. Chem.* 271:8215). PAI-1 does not appear to contribute significantly to thrombin inhibition in plasma in vivo, although local concentrations of PAI-1 may have significant effects. Vn also stimulates the inhibition of tPA by PAI-1, but to a much less dramatic extent (Keijer et al, supra; Edelberg J M et al., *J Biol. Chem* (1991) 266:7488-7493). Vn can partially restore the reduced inhibitory activity of PAI-1 RCL mutants toward tPA.

(e) Interactions with Thrombin

Given that PAI-1 is expressed at sites of inflammation and released from platelet granules upon activation, it may under these conditions be a relevant inhibitor of thrombin. While PAI-1 alone is a rather poor inhibitor of thrombin, PAI-1-Vn complexes have greatly augmented ability to inhibit thrombin (Naski. et al., supra). Vn is present in connective tissue extracellular matrices and released from platelets upon their activation. Thrombin-PAI-1 complexes form on endothelial cell ECM, which can be inhibited with antibodies to Vn (Ehrlich, H. J. et al., (1991) *J. Cell Biol.* 115, 1773-1781). While these authors speculated that the thrombin:PAI-1 interaction might promote PA activity by neutralizing PAI-1, this interaction may also mediate cellular clearance of thrombin. Such clearance would resemble that of tPA and uPA whose endocytosis and degradation via several members of the LDL receptor family are promoted after complex formation with PAI-1 (Nykjaer, A. et al., (1992) *J. Biol. Chem.* 267, 14543-14546 (Orth, K. et al., (1992) *Proc. Natl. Acad Sci. USA* 89, 7422-7426; Stefansson, S. et al., (1995) *J. Cell Sci.* 108: 2361-2369).

(f) Clinical Significance of PAI-1 and its Interactions

Increased levels of circulating PAI-1 are associated with thrombotic disease, including myocardial infarction and deep vein thrombosis (Juhan-Vague I et al., *Thromb Res* (1984) 33:523-530; Hamsten A et al., Engl J Med (1985) 313:1557-1563; Wiman B et al., J Lab Clin Med (1985) 105:265-270; Paramo J A et al., BMJ (1985) 291:573-574; Nilsson I M et al, BMJ (1985) 290:1453-1456; Aznar J et al., Br Heart J (1988) 59:535-541; Angles-Cano E et al., J Lab Clin Med (1993) 121:646-653). Reduced postoperative fibrinolytic activity has been correlated with increased PAI-1 activity immediately following surgery (Kluft C et al., Scand J Clin Lab Invest (1985) 45:605-610), apparently mediated by a plasma factor that stimulates PAI-1 production and secretion from vascular ECs (Kassis J et al., Blood (1992) 80:1758-1764). Consistent with these observations, the overproduction of PAI-1 in transgenic mice results in venous thrombosis primarily in the extremities (Erickson L A et al., Nature (1990) 346:74-76). In contrast, a prospective study found no correlation between PAI-1 levels and vascular disease (Ridker P M et al., Circulation (1992) 85:1822-1827).

Three cases of partial or complete PAI-1 deficiency have been reported in humans and were associated with abnormal bleeding. In one case, normal PAI-1 antigen was detected, but PAI-1 activity was significantly reduced (Schleef R R et al., *J Clin Invest* (1989) 83:1747-1752), whereas in another, both PAI-1 antigen and activity levels in plasma were markedly reduced with normal levels in platelets (Dieval J et al., Blood (1991) 77:528-532). A complete deficiency of platelet and plasma PAI-1 in a 9-year-old Amish girl was associated with a moderate bleeding disorder. The patient was homozygous for a 2 base pair insertion at the end of exon 4 of the PAI-1 gene (Fay W P et al., N Engl J Med (1992) 327:1729-1733) which results in a frameshift leading to a truncated PAI-1 protein and an unstable mRNA. The deficiency is inherited as an autosomal recessive disorder. Although heterozygous parents and siblings all had plasma PAI-1 activity and antigen in the normal range, they were consistently lower than homozygous normal family members. The lack of developmental and other abnormalities in this patient was considered surprising. The correlation of complete PAI-1 deficiency with abnormal bleeding clearly demonstrates that importance of PAI-1 in the regulation of hemostasis. Given the young age of the above patient, however, an additional important in vivo role of PAI-1 in the control of ovulation or tumor metastasis cannot yet be excluded (Pollanen et al., supra; Liu Y-X et al., Eur J Biochem (1991) 195:549-555).

(g) Clearance Receptors

The LDL receptor-related protein (LRP) is a cell surface receptor (family with four members) which acts as a general clearance receptor for a diverse set of ligands, including proteinase inhibitor complexes. For review, see Strickland, D. K. et al., *FASEB J* 9:890-898 (1995)) Binding to LRP results in the uptake of PAI-1-proteinase complexes into cells and destruction in the lysosomal compartment. While LRP is found on all cells, these receptors are present at higher levels in liver and on the epithelial lining of the lungs.

(h) Cell Migration

Cell migration is a tightly controlled process which depends on the coordination of many factors. Migrating cells and cells with invasive phenotypes express high levels of uPA. Processes such as angiogenesis and metastasis can be blocked by proteinase inhibitors. Inactivation of the gene for uPA in mice prevents arterial stenosis due to neointima formation following vascular trauma (Carmeliet, P. et al., *Circulation* 90:1-144 (1994)). During wound healing vascular cells exhibit an increase in the expression of the Vn receptor (VnR) integrin $\alpha_v\beta_3$ (Liaw L et al., *Circ Res* 77:665-72 (1995)). VnR permits cell motility on matrix proteins deposited at the wound. Specifically, migration into the wound area is facilitated by Vn which is deposited at the site by activated platelets or derived from plasma. Migrating vascular cells also show elevated expression of uPA and its receptor UPAR which co-localize with the VnR at focal contacts. As previously understood in the art, the PAs were thought to activate a generalized proteolytic cascade resulting in matrix destruction necessary for cellular migration and invasion. However, results obtained by the present inventors and presented herein suggest a more subtle role for PAs in regulating the expression of cryptic cell attachment sites.

SUMMARY OF THE INVENTION

The present invention provides mutants and variants of wild-type human PAI-1 (wtPAI-1) that have improved properties in the inhibition of serine proteinases, in particular elastase. These mutant PAI-1 molecules are more resistant to destruction by the proteinases to which they bind and therefore have improved therapeutic properties.

The nucleotide sequence (SEQ ID NO: 1; the complementary strand is SEQ ID NO: 10) and amino acid sequence (including the signal sequence) (SEQ ID NO: 2) of human PAI-1 is shown in FIGS. 3A-3D and 4A. The full mature protein sequence (SEQ ID NO: 3) is shown in FIG. 4B.

The present invention is further directed to the use of PAI-1 and mutants and variants thereof for the inhibition of elastase activity. PAI-1 and its mutants are used to treat any of a number of diseases associated with elastase activity, including emphysema, CF and ARDS. Mutants of this invention are also used to inhibit Vn-dependent cell attachment, migration and subsequent proliferation, which processes are associated with diseases ranging from atherosclerosis and restenosis to tumor growth and metastasis and neovascularization.

Thus, the present invention is directed to a mutant protein of PAI-1 protein, which wild-type sequence of which is SEQ ID NO:3, which mutant inhibits neutrophil elastase or other elastase-like proteinases. Preferably the inhibition is such that no more than about one mole of the mutant protein are required to inhibit 1 mole of the elastase. More preferably no more than about two moles, four moles, ten moles, or most preferably 100 moles, of the mutant protein are required to inhibit 1 mole of the elastase.

Also provided is the above mutant protein having at least one amino acid substitution in the sequence from amino acid position 343 to 350 of SEQ ID NO:3, more preferably in positions 331-350. Preferred substitutions are at position 343, position 346 or both. A preferred substitutions at position 346 is Ala, Val, Asp, Phe or Gly. A preferred substitution at position 343 is Ala, Asp, Gly, Leu or Ile. In a preferred embodiment the mutant protein has both a substitution position 343 and 343 as above. Another preferred mutant protein differs from SEQ ID NO:3 by a single substitution of Val at position 346, a single substitution of Ala at position 343, or both. Also provided is a mutant protein having a substitution at 343, 346 or both, wherein the amino acid substituting at position 343: (a) renders the mutant protein resistant to cleavage by elastase after position 343, and (b) has side chains which do not interfere with the binding of the mutant protein to the elastase to form a mutant PAI-1: elastase complex.

A mutant protein as above may further include between one and four of the following additional amino acid substitutions in SEQ ID NO:3 which stabilize the protein: (a) His at position 150; (b) Thr at position 154; (c) Leu at position 319; and (d) Ile at position 354. A preferred mutant includes all four of the above additional substitutions. Additional stabilizing substitutions include Leu at position 91 and Ile at position 372. Also preferred are mutants having additionally Arg at position 333 and/or 335 or at both 333 and 335. An additional substitution in this region is Gly at 331. PAI-1 mutants including any combination of the foregoing substitutions may be used as a stabilized form of the protein, in particular for use in vivo In another embodiment, the present invention is directed to a mutant protein of PAI-1 protein (SEQ ID NO:3) which is particularly useful for inhibiting the binding of PAI-1 to Vn. Such as mutant is characterized as being resistant to inactivation by the following proteinases: elastase, a plasminogen activator, plasmin, thrombin, cathepsin G. chymase, gelastinase A and B, stromelysin and a collagenase. Such an inhibitory PAI-1 mutant protein preferably has high affinity for Vn such that the binding of the mutant protein to a proteinase does not decrease the affinity of binding of the mutant protein to Vn more than about 100-fold relative to the affinity of wtPAI-1 to Vn.

The above mutant protein preferably has at least one amino acid substitution in the fragment from amino acid position 343 to position 350 of SEQ ID NO:3, more preferably from 331 to 350. One or more of the abovementioned substitutions at positions 343 and 346 (as well as at 331, 333 and 335) are preferably included in this embodiment. The mutant protein may have between one and four, preferably all four, of the following additional amino acid substitutions in SEQ ID NO:3 :(i) His at position 150; (ii) Thr at position 154, (iii) Leu at position 319; and (iv) Ile at position 354.

In another embodiment is provided any mutant protein of PAI-1 protein (SEQ ID NO:3) which has a higher affinity for Vn than does wtPAI-1.

Shorter peptides which include at least the PAI-1 reactive center loop with the amino acid substitutions described above are also intended to be within the scope of this invention. Such peptides may be used a elastase inhibitors or cell migration inhibitors in vitro or in vivo. As elastase inhibitors, such peptides (or full length mutant proteins) are useful in methods of measuring or titrating elastase activity.

The present invention is also directed to a pharmaceutical composition useful for inhibiting elastase activity in a subject, comprising (a) a mutant protein (or peptide) as described above, and (b) a pharmaceutically acceptable carrier or excipient:

Also provided is a pharmaceutical composition useful for inhibiting Vn-dependent cell attachment, migration and/or migration-induced cell proliferation in a subject, comprising (a) a mutant PAI-1 protein as described above and (b) a pharmaceutically acceptable carrier or excipient.

This invention is further directed to a method for inhibiting elastase in a subject having a disease or condition associated with pathogenic elastase activity, comprising administering to the subject an effective amount of a pharmaceutical composition as above. The disease or condition is preferably one selected from the group consisting of emphysema, acute respiratory distress syndrome, acute inflammatory lung injury, congenital alpha-1-antitrypsin deficiency, cystic fibrosis, atopic dermatitis, pancreatitis, periodontal disease, arthritis and HIV infection.

Also provided is a method for inhibiting cell attachment, migration and/or migration-induced cell proliferation in a subject having a disease or condition associated with undesired Vn-dependent cell attachment, migration and/or migration-induced proliferation, comprising administering to the subject an effective amount of (a) a pharmaceutical composition comprising wtPAI-1 protein and a pharmaceutically acceptable carrier or excipient; or (b) a pharmaceutical composition comprising a mutant PAI-1 protein as described above.

In the foregoing method, the inhibition is preferably directed to smooth muscle cells. In the foregoing method, the disease or condition is preferably atherosclerosis, post-balloon angioplasty vascular restenosis, neointima formation following vascular trauma, vascular graft restenosis, fibrosis associated with a chronic inflammatory condition, lung fibrosis, chemotherapy-induced fibrosis, wound healing with scarring and fibrosis, primary tumor growth, invasion or growth of a tumor metastasis, psoriasis, deep venous thrombosis, or a disease or condition in which angiogenesis is pathogenic.

This invention is further directed to a nucleic acid molecule, preferably, DNA encoding a mutant PAI-1 protein or peptide as described above. The nucleic acid molecule is preferably a variant of SEQ ID NO:1 or of a coding portion thereof. Also provided is a host cell transformed or transfected with a DNA molecule as above which encodes a mutant PAI-1 protein or peptide. The invention includes methods for producing the mutant PAI-1 protein comprising culturing the transformed or transfected host cells under conditions wherein the mutant PAI-1 protein or peptide is expressed.

Also provided is an antibody, polyclonal or monoclonal, specific for an epitope of a mutant PAI-1 protein as described above, which epitope is not present on wtPAI-1 protein.

BRIEF DESCRIPTION OF THE DRAWINGS

FIGS. 3A-3D show the nucleotide sequence (SEQ ID NO: 1) encoding the human PAI-1 plus 5' and 3' untranslated regions from a particular clone. Also shown is the amino acid sequence of full length human PAI-1 including signal peptide.

FIGS. 4A-4B show the amino acid sequence of the PAI-1 protein. SEQ ID NO:2 (FIG. 4A) includes the signal peptide whereas SEQ ID NO:3 (FIG. 4B) is the mature protein. Preferred residues for substitution to generate mutants are indicated in FIG. 4A as is the reactive center loop (RCL) region.

FIGS. 16 and 17 show endocytosis while FIGS. 18 and 19 show degradation. The results represent 4 experiments each performed in duplicate. Each plotted value represents the average of duplicate determinations with the range indicated by bars.

FIGS. 22 and 23 show endocytosis while FIGS. 24 and 25 show degradation. The results represent 3 experiments. Each plotted value represents the average of duplicate determinations with the range indicated by bars.

FIG. 42A shows the amount of cell attachment to Vn coated plates in the presence of each competitor. FIG. 42B shows the extent of cell migration through Vn coated Transwells in the presence of each competitor. The data represent the average of 5 experiments (FIG. 42A) or 3 experiments (FIG. 42B) all performed in duplicate.

FIG. 50A is a quantitative representation of angiogenesis in response to 2 µM active PAI-1 (the stabilized 14-1B mutant) and 2 µM latent PAI-1 (the wild type sequence). FIG. 50B shows dose dependent inhibition of angiogenesis by active PAI-1 (the 14-1B mutant) at 1, 0.1 and 0.01 µM. FIG. 50C compares the angiogenesis inhibiting activity 2 µM "wt" PAI-1 (the 14-1B 1 mutant, wherein "wild-type" refers to its activity, not its sequence) with two PAI-1 mutants each having one additional amino acid substitution: R346A which binds Vn but is unable to inhibit uPA and Q123K which inhibits uPA but does not bind Vn.

DESCRIPTION OF THE PREFERRED EMBODIMENTS

Figure 1:
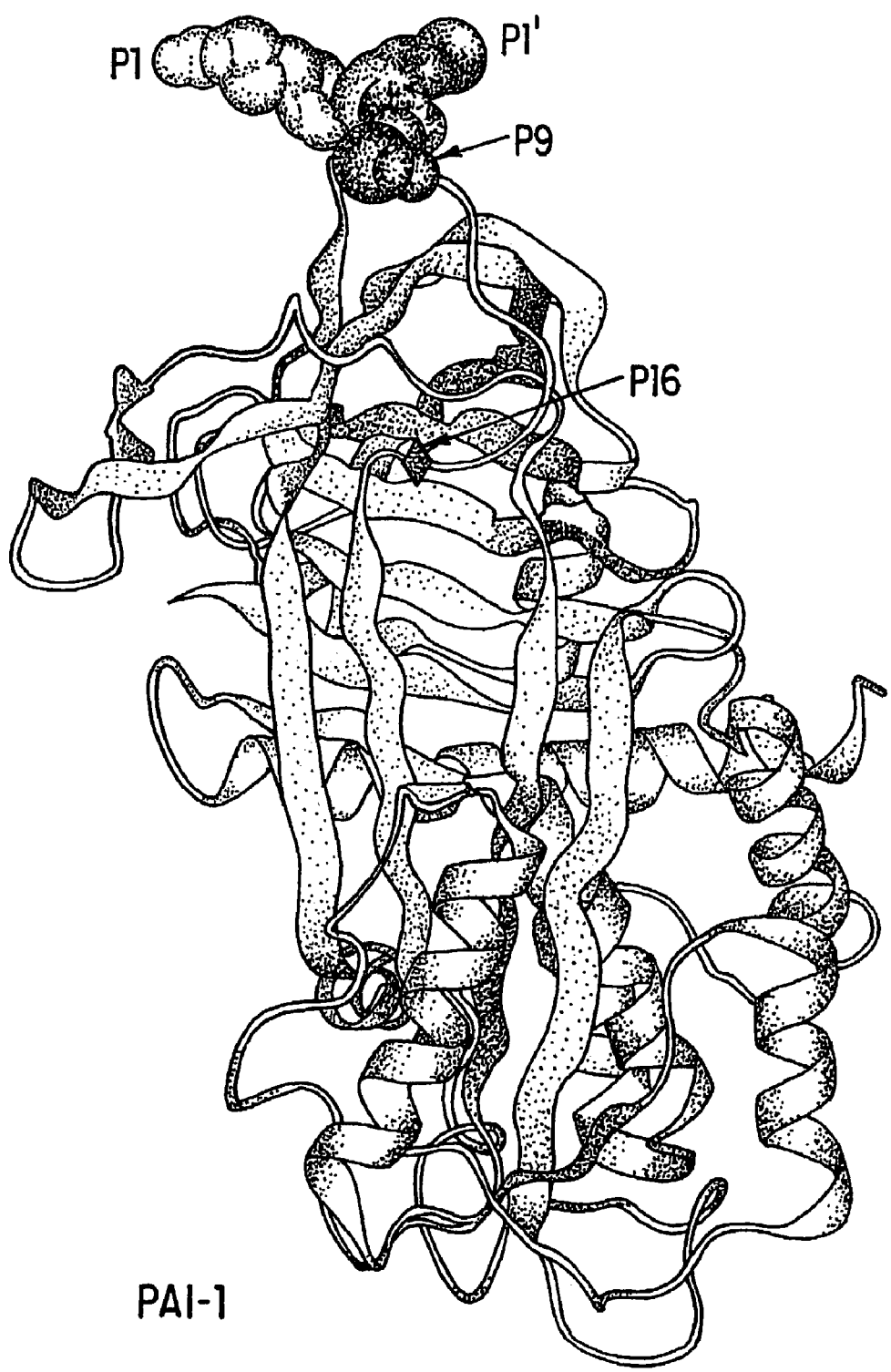
FIGS. 1-2 are models (ribbon diagrams) of active PAI-1 (FIG. 1) and RCL-cleaved (inactive) PAI-1 (FIG. 2). The PAI-1 main chain is shown in gray. Certain of the amino acid residues of the RCL are highlighted. Space filling models of the amino acid side chains of P1 (Arg 346), P1' (Met 347) and P9 (Ser 338) are shown in darker shades of gray. The approximate position of P16 (Ser 331) is indicated by a small black diamond.
Figure 2:
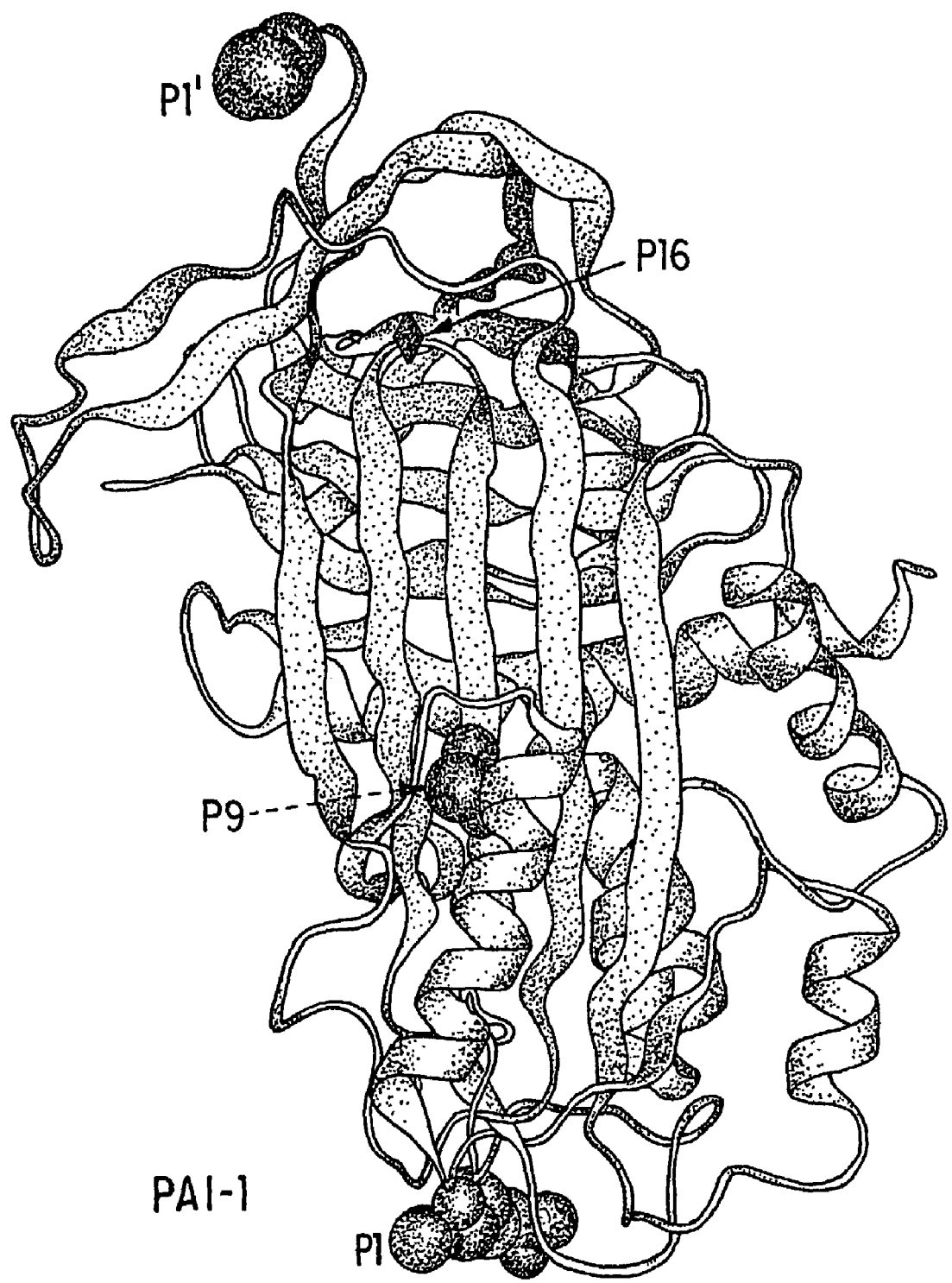

One of the present inventors and colleagues previously used site directed mutagenesis and other methods to produce and characterize a large number of mutations in the PAI-1 reactive center loop (RCL) (Sherman et al., 1992, supra; Sherman et al., 1995, supra). The present inventors have now made or identified new mutants in the RCL of PAI-1 which confer on PAI-1 new and useful properties, in particular (a) the ability to interact with and inhibit elastase, an activity which is lacking in native PAI-1 and (b) the ability to inhibit Vn-associated cell migration. These properties are the basis for the new uses for these mutants described below, for which purposes wild type PAI-1 ("wtPAI-1") or other proteinase inhibitors are less well suited or not useful at all.

The present invention therefore provides novel compositions in the form of mutants of PAI-1 with increased stability as proteinase inhibitors, in particular, as inhibitors of elastase. Secondary to their inhibition of elastase, these mutants promote the uptake and clearance of elastase (or the elastase-PAI-1 complexes) by LDL-related protein clearance receptors. Hence, use of these compositions enhances the removal of elastase from sites of potential or actual injury. The disclosed mutants effectively neutralize elastase at sites of inflammation or injury.

Because of the role of elastase in emphysema, cystic fibrosis (CF) and in acute respiratory distress syndrome (ARDS) in both adult and infant as well as in other conditions discussed below, the present invention provides methods for treating these or any other diseases associated with pathogenic activation of elastase which method comprises administering either PAI-1 or the PAI-1 mutants described herein.

Two functional classes of mutant PAI-1 molecules are contemplated within the scope of the present invention: mutants which inhibit neutrophil elastase (or other elastases)

and mutants which inhibit Vn-dependent cell migration. Preferred mutants possess both these characteristics.

Mutants which Inhibit Elastase

A preferred elastase-inhibiting PAI-1 mutant has the following characteristics:

(1) PAI-1 molecule of fill length or having between 1 and 14 or its N-terminal amino acid truncated;

(2) has an amino acid substitution at the P1 site, the P4 site or both, as further delineated below;

(3) inhibits neutrophil elastase with a second order rate constant of at least $10^5$ $M^{-1}$ $sec^{-1}$ with a stoichiometry of at least 2:1 at physiological salt concentrations and pH in the calorimetric assay described below.

Elastase inhibitory activity is defined as follows: no more than about 100 moles of the inhibitor are required to inhibit 1 mole of the elastase. Preferably no more than about 4 moles, more preferably, no more than about 2 moles and most preferably about 1 mole of the mutant protein is/are required to inhibit 1 mole of elastase.

A preferred substitution at P1 is Ala (R346A) or Val (R346V), although another substitutions, e.g., Met ($\alpha_1$AT has Met al this position) or Asp, is acceptable. The amino acid substitutions described herein are designated interchangeably as, for example, "P1 Ala", which indicates the position in the PAI-1 reactive center as being the P1 site, or R346A which indicates Arg is replaced by Ala at position 346 of PAI-1, SEQ ID NO:3, using the single letter amino acid code.

As shown in the Examples, below, pancreatic elastase is not inhibited by wtPAI-1, pancreatic elastase but is inhibited by the P1 Ala PAI-1 mutant. According to the results shown in FIG. 6, a complex is formed between P1 Ala PAI-1 and elastase but not between wtPAI-1 and elastase. All of the wtPAI-1 is cleaved and thus inactivated by interacting with elastase, which explains its lack of inhibitory action.

Such inactivation of PAI-1 by elastase was also shown by Lawrence, D. A. et al., *J. Biol. Chem.* 269:27657-27662. (1994). In fact, others have published that PAI-1 is not an inhibitor of elastase (Levin E G et al., *J Cell Biol (*1987) 105:2543-2549). Shubeita et al. (supra) actually tried to modify PAI-1 to become an inhibitor of elastase and failed.

A mutant which included a replacement of P1 Arg by Ala, in combination with the wild type Met al P1' was described earlier by the present inventors and their colleagues (Sherman et al., 1992, supra). In FIG. 4 of that reference, it was shown that such a mutant lost the ability to inhibit uPA. This same mutant was later found to lack inhibitory activity toward tPA and thrombin (Sherman et al., 1995, supra, at FIGS. 1 and 2). It is important to note that these described mutants were different from the mutants of the present invention in that the PAI-1 protein contained seven additional amino acids added to its N-terminus Met-Thr-Met-Ile-Thr-Asn-Ser (SEQ ID NO:4) (Sherman et al, 1992, supra, at page 7590, column 2, last paragraph). Furthermore, Shubeita H. E. et al. *J. Biol. Chem.* 1990, 265:18379-85, tried to change the P1 site in PAI-1 to inhibit elastase by using the $\alpha_1$AT amino acid sequence into PAI-1 but found no inhibition.

The reason that the P1 Ala mutant inhibits elastase but not tPA or uPA is thought to be a function of the interaction with the specificity site (S1) of the proteinase (though the inventors do not wish to be bound by any particular mechanistic interpretation). This S1 site of the proteinase is the primary determinant of substrate specificity. Depending on the size and hydrophobicity of the S1 site, it prefers to accommodate one type of amino acid or another. tPA and other PAs prefer basic residues at P1 (Arg or Lys). Elastase prefers small hydrophobic resides like Ala and Val. Hence, by a judicious choice of amino acids in the reactive center of the PAI-1 mutant, it is possible to select a substitution or combination of substitutions that optimize interaction with the elastase S1 site while preventing inactivation of the inhibitor and thereby maximizing it inhibitory capacity and ability to promote clearance of the elastase.

The substitution at the P4 site must be one which results in a protein which is not cleaved after the P4 residue by elastase. For this, it is useful to substitute for the Val at this position in the wtPAI-1. This resistance to inactivation permits the mutant to successfully inhibit elastase. Thus, a preferred amino acid substituent (a) is resistant to cleavage by elastase at this site, i.e., does not act as a substrate site for elastase and (b) at the same time does not present side chains which interfere with the interaction and binding of PAI-1 to elastase to form a complex such that elastase activity is inhibited and the complex is efficiently cleared. Stated otherwise, the substituting amino acid at P4 should present a poor fit as a primary (substrate) site for elastase without distorting other subsite contacts which are needed for interaction and successful inhibition.

Preferred amino acids at P4 are small, such as Ala and Gly, though somewhat larger residues such as Leu and Ile are also contemplated. The amino acid may be charged, such as Asp which should make that site less amenable to cleavage by elastase.

If the P4 site is substituted, for example, with Ala, a larger number of possible substitutions at P1 are expected to result in a molecule with the desired inhibitory properties. The efficiency or rate of inhibition (second order rate constant) is expected to will be highest with Val at P1.

Mutations which Inhibit Cell Migration

A preferred PAI-1 mutant for inhibition of cell migration is any one which has high affinity for Vn and thereby allows the blockade of integrin (Vn receptor) attachment to Vn. wtPAI-1 has this property. A second characteristic of such a mutant is that it is resistant to inactivation by a proteinase, most preferably, elastase, plasminogen activators, plasmin, thrombin, cathepsin G, chymase, gelatinase A and B, stromelysin and collagenase Any mutants which fulfill these criteria are intended.

A mutant protein or peptide with "high affinity" for Vn is defined as one in which binding to the proteinase target does not cause a significant loss of affinity for Vn (due to conformation change of the PAI-1 protein or peptide). Loss of affinity for Vn is defined as an increase in Kd of more than about 100 times the Kd of the wtPAI-1. For example, where the Kd of wtPAI-1 for Vn is about 10 nM in a conventional assay, a preferred mutant will have Kd for Vn of about 100 nM or lower after binding the protease, more preferably a Kd of 10 nM or lower.

The property of resistance to inactivation cleavage by a proteinase upon binding to and inhibiting the proteinase is best achieved by a PAI-1 mutation in the RCL, preferably at the P1 site. A preferred mutant is P1 Ala. Alternatively, or additionally, a substitution at P4 which inhibits proteinase cleavage after the P4 site is also preferred, for example P4 Ala.

As stated above, a fragment of PAI-1 which has the requisite elastase-inhibiting or migration-inhibiting activity is within the scope of this invention. Such a fragment generally has most of the amino acids of full length PAI-1, and preferably does not have more than the 14 N-terminal amino acids cleaved. However, if it is later discovered that other fragments of PAI-1 maintain the requisite biochemical functions, then mutants of those fragments in accordance with the description above are within the scope of this invention.

Also included is a mutant of a longer polypeptide which has the delineated properties of PAI-1 along with the particular characteristics of the mutants described herein. Thus, for example, the N-terminal 30 amino acids of PAI-1 have been replaced with the N-terminal 50 amino acids of α1AT, resulting in a polypeptide that is longer by 20 amino acids than PAI-1 but retains biochemical properties of PAI-1. Substitution mutants of such a longer molecule of the type described above are also intended, provided that such mutants inhibit elastase or inhibit cell migration.

In addition to the aforementioned amino acid substitutions which bestow on PAI-1 the desirable characteristics for utility in accordance with the present invention, additional amino acid substitutions are known which stabilize PAI-1 (Berkenpas, M. et al., *EMBO J.* 14:2969-2977, 1995)). Preferred compositions will optionally include, in addition to substitutions at P1 and P4 sites, four additional substitutions at positions 150, 154, 319 and 354 of SEQ ID NO3 as in the mutant designated 14-1B-by Berkenpas et al., supra. These substitutions are N150H, K154T, Q319L, M354I.

The list below summarizes (non-exclusively) preferred PAI-1 mutants. The amino acid residues shown are at positions P4-P4' in the RCL (corresponding to residues 343 to 350 of SEQ ID NO:3).

Also intended are mutants such as these listed below additionally having one or more of the following two substitutions: T333R (Arg at residue 333 in place of Thr), and A335R (Arg at 335 in place of Ala) and, optionally, S331G (Gly at residue 331 in place of Ser). The importance of these positions, in particular the 333 position, is described in Lawrence, D. A. et al., *J. Biol. Chem.* 269:27657-27662 (1994), which is incorporated by reference in its entirety.

While the present disclosure is directed primarily to human PAI-1, it is to be understood that homologues of PAI-1 from other species, and mutants thereof, that possess the characteristics disclosed above are intended within the scope of this invention. In particular, the PAI-1 protein (or DNA) from other mammalian species may be used for the same purposes as human PAI-1 in the treatment of diseases or conditions in humans or in other mammalian species.

As noted above, the present invention also includes peptides which include at least that portion of the sequence which contains the substitution or substitutions, and which possess the requisite biochemical and biological activity such as elastase inhibition. Such peptides may be produced using well-known synthetic methods for the synthesis of polypeptides of desired sequence on solid phase supports and their subsequent separation from the support. Methods for solid phase peptide synthesis are well-described in the following references, hereby incorporated by reference: Merrifield, B., *J. Amer. Chem. Soc.* 85:2149-2154 (1963);

|  |  | 343 344 345 346 347 348 349 350 |
|---|---|---|
|  | wtPAI-1 (SEQ ID NO:16) | Val-Ser-Ala-Arg-Met-Ala-Pro-Glu |
| | Mutants | |
| 1. | P1Ala (R346A) (SEQ ID NO:17) | Val-Ser-Ala-<u>Ala</u>-Met-Ala-Pro-Glu |
| 2. | P1Val (R346V) (SEQ ID NO:18) | Val-Ser-Ala-<u>Val</u>-Met-Ala-Pro-Glu |
| 3. | P1Gly (R346G) (SEQ ID NO:19) | Val-Ser-Ala-<u>Gly</u>-Met-Ala-Pro-Glu |
| 4. | P1Asp (R346D) (SEQ ID NO:20) | Val-Ser-Ala-<u>Asp</u>-Met-Ala-Pro-Glu |
| 5. | P4Ala(V343A) (SEQ ID NO:21) | <u>Ala</u>-Ser-Ala-Arg-Met-Ala-Pro-Glu |
| 6. | P4Asp (V343D) (SEQ ID NO:22) | <u>Asp</u>-Ser-Ala-Arg-Met-Ala-Pro-Glu |
| 7. | P4Gly (V343G) (SEQ ID NO:23) | <u>Gly</u>-Ser-Ala-Arg-Met-Ala-Pro-Glu |
| 8. | P4Leu (V343L) (SEQ ID NO:24) | <u>Leu</u>-Ser-Ala-Arg-Met-Ala-Pro-Glu |
| 9. | P4Ile (V343I) (SEQ ID NO:25) | <u>Ile</u>-Ser-Ala-Arg-Met-Ala-Pro-Glu |
| 10. | P4AlaP1Val (V343A, R346V) (SEQ ID NO:26) | <u>Ala</u>-Ser-Ala-<u>Val</u>-Met-Ala-Pro-Glu |
| 11. | P4AlaP1Ala (V343A, R346A) (SEQ ID NO:27) | <u>Ala</u>-Ser-Ala-<u>Ala</u>-Met-Ala-Pro-Glu |
| 12. | P4AlaP1Asp (V343A, R346D) (SEQ ID NO:28) | <u>Ala</u>-Ser-Ala-<u>Asp</u>-Met-Ala-Pro-Glu |
| 13. | R346A plus N150H,K154T,Q319L,M354I | |
| 14. | R346V plus N150H,K154T,Q319L,M354I | |
| 15. | V343A,R346V plus N150H, K154T, Q319L, M354I | |
| 16. | V343A,R346D plus N150H, K154T, Q319L, M354I | |

Merrifield, B., *Science* 232:341-347 (1986); Wade, J. D. et al., *Biopolymers* 25:S21-S37 (1986); Fields, G. B., *Int. J. Peptide Prot. Res.* 35:161 (1990); MilliGen Report Nos. 2 and 2a, Millipore Corporation, Bedford, Mass., 1987). For example, the more classical method, "tBoc method," or the more recent improved. "F-moc" technique may be used (Atherton, E. et al., *J. Chem. Soc. Perkin Trans.* 1:538-546 (1981)).

In addition to their uses as inhibitory agents, as disclosed for the protein mutants, these peptides are also used in laboratory tests such as novel elastase titration assays. The peptides are also used to immunize animals to make mutant-specific antibodies, as antigens in immunoassays to screen hybridoma supernatants, or as solid phase immunoadsorbents to purify mutant-specific antibodies.

Production of PAI-1 Mutants by Expression and Purification of Recombinant PAI-1 in *E. coli*

The following methods are preferred and do not represent the exclusive means for carrying out this invention. Techniques for synthesizing oligonucleotides probes are well known in the art and disclosed by, for example, Wu, R., et al, *Prog. Nucl. Acid Res. Molec. Biol.* 21 101-141 (1978) or Gait, ed., *Oligonucleotide Synthesis* (Current Edition)). Procedures for constructing and expressing recombinant molecules in accordance with this invention, including appropriate promoters and other control elements, selection markers, etc., are disclosed by Sambrook, J. et al., In: *Molecular Cloning: A Laboratory Manual*, Second Edition, Cold Spring Harbor Press, Cold Spring Harbor, N.Y. (1989); Ausubel, F. M. et al. *Current Protocols in Molecular Biology*, Vol. 2, Wiley-Interscience, New York, 1987; *DNA Cloning: A Practical Approach*, vol. I & II (D. Glover, ed.), which references are herein incorporated by reference.

Included in this invention is the DNA encoding the PAI-1 mutant, which is preferably a cDNA having the appropriate nucleotide sequence substitutions to encode the mutant proteins as disclosed herein. Such molecules are prepared using conventional methods. Also included herein are prokaryotic or eukaryotic host cells transformed or transfected with a vector comprising the above DNA molecule. Again, the method used for transferring the DNA, expressing the DNA and growing the host cells are well-known in the art and described in the references cited above. Eukaryotic host cells are preferably mammalian cells of an established cell line, although insect cells or plant cells are also contemplated. Appropriate vectors such as viruses, vector sequences, control sequences, such as promoters appropriate for the species of host cells, are conventional and well-known to those skilled in the art and are therefore not described in particular detail herein. In addition to sense DNA, antisense DNA and antisense RNA molecules to the mutant PAI-1 coding sequence are provided herein. Also included is an RNA molecule encoding the PAI-1 mutant.

Site directed Mutagenesis of PAI-1

A preferred method for producing PAI-1 mutants utilizes a commercially available kit and was described by one of the present inventors and his colleagues in a reference which is hereby incorporated by reference in its entirety (Lawrence, D. A. et al., *Biochemistry* 33 3643-3648, 1994).

Site-specific or site-directed mutagenesis allows the production of peptide variants through the use of specific oligonucleotide sequences that encode the DNA sequence of the desired mutation plus a sufficient number of adjacent nucleotides, to provide a primer sequence of sufficient size and sequence complexity to form a stable duplex on both sides of the deletion junction being traversed. Typically, a primer of about 20 to 30 nucleotides in length is preferred, with about 5 to 10 residues on both sides of the junction of the sequence being altered. The technique of site-directed mutagenesis is well known in the art, as exemplified by publications such as Adelman et al., *DNA* 2:183 (1983), which is incorporated herein by reference. As will be appreciated, the mutagenesis technique typically employs a phage vector that exists in both a single-stranded and double-stranded form. Typical vectors useful in site-directed mutagenesis the M13 phage (Messing et al., *Third Cleveland Symposium on Macromolecules and Recombinant DNA*, Editor A. Walton, Elsevier, Amsterdam (1981)). These phage are commercially available and their use is well known to those skilled in the art. Alternatively, plasmid vectors that contain a single-stranded phage origin of replication (e.g., Veira et al., *Meth. Enzymol.* 153:3 (1987)) may be employed to obtain single-stranded DNA.

In general, site-directed mutagenesis in accordance herewith is performed by first obtaining a single-stranded vector that includes within its sequence a DNA sequence that encodes the PAI-1 protein (or peptide). An oligonucleotide primer bearing the desired mutated sequence is prepared, generally synthetically (e.g., Crea et al., *Proc. Natl. Acad Sci.* (*USA*) 75:5765 (1978). This primer is annealed with the vector comprising the single-stranded protein-coding sequence and is subjected to DNA-polymerizing enzymes such as *E. coli* polymerase I Klenow fragment to complete the synthesis of the mutation-bearing strand. Thus, a mutated sequence and the second strand bears the desired mutation. This heteroduplex vector is then used to transform appropriate cells (such as JM101 cells) and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

For producing PAI-1 mutants, the mutagenesis is most preferably performed using the Altered Sites® mutagenesis kit (now designated "Altered Sites II®") following the manufacturers instructions (Promega). Briefly, PAI-1 cDNA, along with T7 promoter and terminator regulatory sequences, is isolated as an XbaI-EcoRV fragment from the PAI-1 expression plasmid pET3 aPAI-1 (Sherman et al. 1992, supra). This fragment is ligated to PstI/XbaI cut pSELECT-1® (Promega) (now designated "pALTER®"), that had been blunt-ended at the PstI site, creating phagamid pSELPAI-1. This construct is then transformed into *E. coli* strain JM109, and single-stranded DNA is produced by infection with the helper phage R408 (Promega).

The following is a list of oligonucleotides used to generate the preferred mutants at the P1 and P4 sites of PAI-1.

```
P1 Ala
5'-GTCTCAGCCGCCATGGCCCCC          (SEQ ID NO:5)

P1 Val
5'-GTCTCAGCCGTCATGGCCCCC          (SEQ ID NO:6)

P4 Ala
5'-GCTGTCATAGCCTCAGCCCGC          (SEQ ID NO:7)

P4 Ala, P1 Val
5'-GCTGTCATAGCCTCAGCCGTCATGGCCCC  (SEQ ID NO:8)

P4 Ala, P1 Ala
5'-GCTGTCATAGCCTCAGCCGCCATGGCCCC  (SEQ ID NO:9)
```

A newer method is available for enhanced site-elimination mutagenesis which can be applied in the preparation of the mutant PAI-1 proteins. The new Chameleon™ mutagenesis kit (Stratagene) may be used to produce one or more site-specific mutation in virtually any double-stranded plasmid (containing a unique nonessential restriction site), thus eliminating the need for subcloning into M13-based vectors and single-strand DNA rescue (Papworth et al., *Strategies* 7:38-40(1994)). The Chameleon™ kit applies a modification of the unique site-elimination mutagenesis procedure of Deng and Nickoloff (*Anal. Biochem.* 200:81 (1992)). The improved protocol includes the use of: (1) more target DNA and a new primer:template ratio; (2) native T7 DNA polymerase instead of T4 DNA polymerase; (3) a new mutS cell line that does not produce endonuclease A; and (4) highly competent XLmutS and XL1-Blue® cells for transformation of mutated plasmid DNA. These modifications increase the yield and quality of mutated plasmid DNA, resulting in consistently higher colony numbers and mutagenesis efficiencies. The Chameleon™ mutagenesis kit has been used to introduce insertions, point mutations and deletions as large as 48 bp (Papworth et al., *Strategies* 7:78-79 (1994)) and has also been used with three mutagenic oligonucleotides to simultaneously generate triple mutations. The kit includes competent cells of the XLmutS host strain bearing the endA mutation which removes an endonuclease that degrades miniprep DNA, improving the yield and quality of the mutated plasmid DNA and the reproducibility of the mutagenesis procedure.

The mutagenesis procedure involves simultaneously annealing two oligonucleotide primers to the same strand of denatured double-stranded plasmid DNA. One primer (the mutagenic primer) introduces a chosen mutation, and the second primer (the selection primer) alters the sequence of a unique restriction site in the plasmid in order to create a new restriction site. Extension of these primers with T7 polymerase and ligation of the resulting molecules with T4 ligase are followed by restriction enzyme digestion. Any plasmid molecules that renature without inclusion of the selection primer will be linearized, while those that form with the selection primer will not. The resulting mixture is transformed into the highly competent XLmutS *E. coli* strain, which is unable to perform mismatch repair. The transformed bacteria are grown overnight in liquid culture, and the plasmid DNA is recovered and treated again with the restriction enzyme that digests plasmids containing the original restriction site. Plasmids containing the new restriction site and the chosen mutation will resist digestion. Transformation of this DNA into highly competent *E. coli* such as XLI-Blue results in 70-91% of the colonies containing mutated plasmids. If a second round of mutagenesis is desired, a switch primer can be used to "switch" from the new unique restriction site back to the original or another restriction site, at the same time incorporating another mutation. This process makes it possible to perform several rounds of mutation.

Selection primers made by Stratagene select against restriction enzyme sites in the antibiotic-resistance genes for ampicillin, chloramphenicol and neomycin/ kanamycin. (There are also primers available for the ColE1 origin of replication and the polylinker of both SK and KS versions of the pBluescript® II phagemid.) The switch primers allow a second round of mutagenesis to recreate the original unique restriction site.

Expression, Purification and Characterization of PAI-1 Mutants

A novel phagemid vector for efficient mutagenesis and protein expression has been designed by one of the present inventors and his colleagues. This construct, pSELPAI-1, eliminates the need to isolate and subclone each new mutant into an expression plasmid. The inclusion of T7 promoter and terminator sequences in the PSELPAI-1 constructs permits efficient PAI-1 expression directly from this vector using an *E. coli* strain producing T7 polymerase (Studier et al., 1990, *Meth. Enzymol.* 185:60-89). Using this system, site-directed mutagenesis is generally achieved with greater than 50% efficiency. In addition, sequence analysis of greater than 10 kb, from 8 independent clones, has identified no other mutations, indicating a very low rate of secondary mutations (<0.01%).

Briefly cells of the *E. coli* strain BL21 (DE3) transformed with the pSELPAI-1 mutants are grown to an $OD_{650}$ of 0.5, PAI-1 production is induced by the addition of 1M isopropylthio-β-D-galactoside, and growth is continued at 37° C. for 2 h. Cells are harvested and PAI-1 is purified as described Lawrence et al., 1989, supra; Sherman et al., 1992, supra). Protein yields are approximately 1-5 mg/L of cell culture. Purity is assessed by SDS-PAGE and staining by Coomassie blue. Inhibitory activity against both uPA (American Diagnostica) and tPA (Activase, Genentech) is measured in a single step chromogenic assay as described (Lawrence et al., 1989, supra) and compared to wtPAI-1 purified from *E. coli* carrying the expression plasmid pET3aPAI-1 (Sherman et al., 1992, supra). Inhibitory activity against elastase is tested as described in Example I, below Other activities, enhancement of clearance or inhibition of cell migration are tested using methods described in more detail in the Examples.

All the mutant proteins have specific activities similar to wild type PAI-1, demonstrating approximately 50% of the calculated maximum theoretical specific activity (Lawrence et al., 1989, supra). The chromatographic profiles of each mutant, from every step of the purification, are similar to those of wtPAI-1. None of the mutations significantly affect heparin binding. Each mutant binds Vn with approximately the same affinity as does wtPAI-1.

Chemical Modification of the Protein

A "chemical derivative" of PAI-1 contains additional chemical moieties not normally a part of the protein. Covalent modifications of the PAI-1 mutant proteins are included within the scope of this invention. Such modifications may be introduced into the molecule by reacting targeted amino acid residues with an organic derivatizing agent that is capable of reacting with selected side chains or terminal residues. Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences*, 16th ed., Mack Publishing Co., Easton, Pa. (1980). Clearly, any chemical modifications included herein will not substantially alter the advantageous properties of the PAI-1 mutants as described above.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal;

chloroborohydride, trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'-N-C-N-R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues may be deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecule Properties*, W H. Freeman & Co., San Francisco, pp. 79-86 (1983)), acetylation of the N-terminal amine, and, in some instances, amidation of the C-terminal carboxyl groups. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatible intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Among the desired chemical modifications is the labeling of the mutant protein or peptide with a detectable label that permits its use in in vivo diagnostic methods or in vitro detection methods. A "diagnostically effective" amount of the protein is an amount of detectably labeled protein or peptide which, when administered, is sufficient to enable detection of a site protein binding or deposition or clearance. Use of the protein to detect, for example, thrombosis, fibrin deposition, atherosclerotic plaque or cancer is intended. Generally, the dosage of detectably labeled mutant PAI-1 for diagnosis will vary depending on considerations such as age, condition, sex, and extent of disease in the patient, contraindications, if any, and other variables, to be adjusted by the diagnostician. Dosage can vary from 0.01 µg/kg to 2 mg/kg, preferably 0.1 µg/kg to 1 mg/kg. The term "diagnostically labeled" means that the protein or peptide has attached to it a diagnostically detectable label. There are many different labels and methods of labeling known in the art. Examples of the types of labels which can be used in the present invention include radioactive isotopes, paramagnetic isotopes, and compounds which can be imaged by positron emission tomography (PET). Those of ordinary skill in the art will know of other suitable labels for binding to the proteins or peptides used in the invention, or will be able to ascertain such, using routine experiments. Furthermore, the binding of these labels to the protein is done using standard techniques such as cross-linking, covalent attachment, non-covalent attachment, or complexing.

Antibodies Specific for Epitopes of the Mutant Protein

The present invention is also directed to an antibody specific for the mutant PAI-1 protein. The antibody is one which recognizes an epitope of the mutant protein not present in the wtPAI-1 protein. Such antibodies are produced by convention means such as immunization of an animal with a mutant protein or a peptide thereof which contains one or more amino acid substitution. Such peptides may be chemically synthesized using conventional methods. Methods of immunization, adjuvants, schedules, etc., are all known in the art. An antiserum produced in this way is tested by any immunochemical or serological assay for binding to the mutant protein as well as to the wt protein. Reactivity for the wt protein can be removed by immunoadsorption of the serum to immobilized wt protein until only reactivity to mutant epitopes remain.

Alternatively, a monoclonal antibody (mAb) is produced specific for epitopes of the mutant PAI-1 by appropriate immunization, cell fusion, growth of hybridoma cells and testing and selection of the supernatant for the desired specificity. Those hybridoma cell lines producing the desired mAb are selected and grown in large quantities. Selection is accomplished by standard immunoassay, such as an enzyme immunoassay (EIA or ELISA) of the culture fluids with the wt protein and the mutant protein. Alternatively, peptides of the mutant protein including the amino acid substitution or substitutions may be used in the screening assay. A mAb of the invention is one which reacts strongly with a mutant protein or peptide and has little or not detectable reactivity with the wtPAI-1.

The antibody of the invention may be used to detect and quantitate the presence of the PAI-1 mutant protein in a biological sample, such as a body fluid or tissue extract of a subject being treated with the protein. In this way, the treatment protocol can be monitored and levels of the mutant evaluated. Furthermore, the antibody can be used to isolate or purify the mutant protein from a mixture containing the wt protein.

Several standard reference works setting forth methods for making, testing and using the antibodies described above include: Hartlow, E. et al., *Antibodies: A Laboratory Manual*, Cold Spring, Harbor Laboratory Press, Cold Spring Harbor, N.Y., 1988); Maggio, E. (ed.), *Enzyme Immunoassay*, CRC Press, Boca Raton, Fla., 1980; Bizollon, Ch (ed.), *Monoclonal Antibodies and New Trends in Immunoassays*, Elsevier, N.Y., 1984.). These references are incorporated by reference in their entirety

Therapeutic Compositions and Methods

The preferred animal subject of the present invention is a mammal. The invention is particularly useful in the treatment of human subjects. By the term "treating" is intended the administering to subjects of a pharmaceutical composition comprising a PAI-1 mutant protein of this invention for inhibiting elastase or inhibiting Vn-dependent cell migration and subsequent proliferation, which inhibition may prevent, ameliorate or cure any of a number of diseases described herein.

The pharmaceutical compositions of the present invention wherein a PAI-1 mutant protein is combined with pharmaceutically acceptable excipient or carrier, may be administered by any means that achieve their intended purpose. Amounts and regimens for the administration of can be determined readily by those with ordinary skill in the clinical art of treating any of the particular diseases. Preferred amounts are described below.

Administration may be by parenteral, subcutaneous (sc), intravenous (iv), intramuscular, intraperitoneal, transdermal, topical or inhalation routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the mutant PAI-1 protein or peptide is contained in an amount effective to achieve its intended purpose. While individual needs vary, determination of optimal ranges of effective amounts of each component is within the skill of the art. Typical dosages comprise 0.1 to 100 mg/kg/body weight, though more preferred dosages are described for certain particular uses, below As stated above, in addition to the pharmacologically active protein, the new pharmaceutical preparations may contain suitable pharmaceutically acceptable carriers comprising excipients and auxiliaries which facilitate processing of the active compounds into preparations which can be used pharmaceutically as is well known in the art. Suitable solutions for administration by injection or orally, may contain from about 0.01 to 99 percent, active compound(s) together with the excipient.

Included in the scope of this invention are salts of the PAI-1 protein or peptide. The term "salts" refers to both salts of carboxyl groups and to acid addition salts of amino groups of the protein or peptide. Salts of a carboxyl group include inorganic salts, for example, sodium, calcium, ammonium, ferric or zinc salts, and the like, and salts with organic bases such as those formed with amines, such as triethanolamine, arginine, or lysine, piperidine, procaine, and the like. Acid addition salts include salts with mineral acids such as hydrochloric or sulfuric acid, and salts with organic acids such as acetic or oxalic acid.

The pharmaceutical preparations of the present invention are manufactured in a manner which is itself known, for example, by means of conventional mixing, granulating, dissolving, or lyophilizing processes. Suitable excipients may include fillers binders, disintegrating agents, auxiliaries and stabilizers, all of which are known in the art. Suitable formulations for parenteral administration include aqueous solutions of the proteins in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions that may contain substances which increase the viscosity of the suspension.

The pharmaceutical formulation for systemic administration according to the invention may be formulated for enteral, parenteral or topical administration, and all three types of formulation may be used simultaneously to achieve systemic administration of the active ingredient.

As described for lung instillation, aerosolized solutions are used. In a sprayable aerosol preparations, the active protein may be in combination with a solid or liquid inert carrier material. This may also be packaged in a squeeze bottle or in admixture with a pressurized volatile, normally gaseous propellant. The aerosol preparations can contain solvents, buffers, surfactants, and antioxidants in addition to the protein of the invention.

For topical application, the proteins of the present invention may be incorporated into topically applied vehicles such as salves or ointments, which have both a soothing effect on the skin as well as a means for administering the active ingredient directly to the affected area.

The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Examples of preferred vehicles for non-sprayable topical preparations include ointment bases, e.g., polyethylene glycol-1000 (PEG-1000); conventional creams such as HEB cream; gels; as well as petroleum jelly and the like. One particularly preferred cream is described below.

Other pharmaceutically acceptable carriers for the PAI-1 protein according to the present invention are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

The PAI-1 mutant proteins described herein have been designed specifically to inhibit elastase and to inhibit cell migration in particular migration of smooth muscle cells (SMCs). Therefore, pharmaceutical compositions comprising such a protein are useful for inhibiting elastase and/or inhibiting cell migration, in the treatment of various diseases and conditions which are associated with elastase activity or undesired cell migration and proliferation.

Lung Diseases Associated with Elastase

Elastase is known to play a significant role in a number of inflammatory conditions and other forms of lung injury, and which result in acute respiratory distress syndrome (ARDS) both of the adult variety and the neonatal form (Koleff, M. H. et al., *New Eng. J. Med.* 332:27-37 (1995); Speer, C. P. et al. *Pediatrics* 91:794-799 (1993)). There are currently no useful pharmacotherapeutic approaches to ARDS, particularly early in the disease process. It is believed that a protease-inhibitor imbalance may contribute essentially to acute lung damage in early stages of ARDS. The mutant PAI-1 proteins are useful in restoring this imbalance and tipping it in favor of proteinase (particularly elastase) inhibition.

Furthermore the importance in lung injury of the extravasation of neutrophils from the pulmonary microvascular compartment into interstitium and alveolar space is recognized (Strieter, R. M. et al., *J. Invest. Med.* 42:640-(1994)). These processes involve β2 integrins and selectins, such neutrophil L-selectin interacting with activated endothelium E- and P-selectins and neutrophil β2 integrin interacting with EC ICAM-1 in neutrophil-EC adhesion, margination or rolling. Expression of these cell surface molecules and the activity of the cells are influenced by the cytokines TNF and IL1. These two cytokines are initiators and promoters, setting into motion cascade of events leading to microvascular inflammation. The mutant PAI-1 proteins are useful in modulating such neutrophil migratory activity and ultimately, in inhibiting the action of their secreted product, elastase which is responsible for much of the tissue injury.

Emphysema is known to be in large part a result of elastase-mediated tissue injury. Augmentation of lung antiprotease levels would be an important therapeutic intervention in prevention or retardation of developitnet of emphysema (Smith, R. M. et al., *J. Clin. Invest.* 84: 1145-1154 (1989)). In the foregoing study, aerosols of α1AT were administered to lungs of dogs and sheep. α1AT was found on the surface of alveoli and distal bronchioles 2 hrs after administration and was present in lavage fluid; antielastase activity was proportional to the concentration of human α1AT given.

Emphysema secondary to congenital α1AT deficiency also results from insufficient amounts of a α1 AT to protect lower respiratory tract from neutrophil elastase (Hubbard, R. C. et al., *J. Clin. Invest.* 84:1349-1354 (1989).

Emphysema, including that due to α1AT deficiency can benefit from treatment with the elastase-inhibiting PAI-1 mutants of the present invention.

In cystic fibrosis, CF, neutrophil-dorninated inflammation on respiratory epithelial surface results in chronic epithelial burden of neutrophil elastase (McElvaney, N. G. et al., *Lancet* 337:392-394 (1991)). α1AT given in aerosol form to CF patients suppressed neutrophil elastase in the respiratory epithelial lining fluid (ELF) and restored ELF anti-elastase capacity. This treatment also reversed inhibitory effect of CF ELF on Pseudomonas killing by neutrophils suggesting augmentation of host defenses. Airway inflammation in CF was diminished and IL-8 levels on the respiratory epithelial surface were suppressed by aerosolization of recombinant secretory leukoprotease inhibitor (rSLPI) (McElvaney, N. G. et al., *J. Clin. Invest.* 90:1296-1301 (1992)). This treatment elastase detectable in ELF and appeared to breaks the cycle of inflammation on CF epithelial surface. rSLPI is a 12 kDa single chain nonglycosylated protein made in *E. coli* with identical structure and function to normal human SLPI (Thompson, R C et al., *Proc. Aati. Acad. Sci. USA* 83:6692-6696 (1986)).

Based on the foregoing, the PAI-1 mutant compositions are used to inhibit elastase in patients with CF, thereby treating various symptoms of the disease.

For treating the above forms of lung disease, use of aerosols is preferred to maintain protective alveolar levels. Those of skill in the art will know how to determine the efficiency of for deliverv into alveolus. If efficiency is expected to be in the range of 10-20%, 10-200 mg of active PAI-1 mutant protein will be needed to be aerosolized per day or 70-1400 mg/week to maintain desired levels in alveolar fluid. improved aerosol delivery methods would reduce amount required. Aerosolized PAI-1 mutant proteins retain their antielastase activity and can penetrate into and deposit on the surface of distal airspaces in lung. Aerosolized PAI-1 mutant proteins in avoids problems with high renal clearance associated with intravenous (iv) administration of some agents.

Aerosol is generated by convention means, for example with compressed air-driven nebulizer. The aerosol preferably has mass median diameter of 1-4 µM. Escalating dosing may be used and the amounts of PAI-1 proteins can be evaluated by lavage and the dosing adjusted accordingly.

Alternatively, the proteins can be administered parenterally at a dose range of about 10-200 mg/kg/wk.

Other Elastase-Related Diseases

According to Travis, J. et al., *J Respir. Crit. Care Med*, 150:S143-146 (1994), periodontal disease shares certain pathophysiologic features with emphysema such as accumulation and degranulation of neutrophils at inflammatory sites as result of frustrated phagocytosis and specific activation of these phagocytic cells. In periodontitis, the process begins with accumulation of plaque at base of teeth followed by growth of opportunistic anaerobic bacterial below the gum line. These organisms resist killing by both monocytes and neutrophils, secrete proteinases that activate kallikrein-kinin pathway, degrade clotting factors and release chemotactic factor C5a from complement. Neutrophils are recruited to infected sites, attempt to phagocytose bacteria, followed by inactivation of proteinase inhibitors and degradation of connective tissue proteins, yielding destruction of gingiva. The present compositions are useful in treating periodontal disease, topically or systemically, through inhibition of elastase and other mechanisms discussed above.

Atopic dermatitis (AD), which affects both children and adults, has no established etiology thouigh it has been suggested that during inflammation, an excess of serine proteinases accumulates at the local site of injury together with a deficiency of their natural inhibitors (Wachter, A. M. et al., *Ann. Allergy*, 69:407-414 (1992)). α1AT was tested for treatment of recalcitrant AD. Patients showed significant clinical improvement within 6 to 21 days of initiation of alternate day therapy. α1AT stopped pain, pruritus and promoted tissue healing without scarring.

Periodontal disease is treated preferably by topical application of the mutant PAI-1 protein, or alternatively, by systemic therapy. AD is treated by topical administration of a PAI-1 mutant protein. Effective doses for both diseases range from about 1 to about 100 mg/ml, preferably about 20-50 mg/ml of mutant PAI-1 protein in aqueous solution given on an alternate days schedule. For treating hands, about 5-10 ml the protein in solution is introduced into an occlusive glove which is placed on the subject. Other known occlusive dressings may be used at other sites. In conjunction with the aqueous solution, a cream of PAI-1 mutant protein at a concentration of about 0.2-5%, preferably about 1% is used. For example, aqueous treatment is given on alternate days for 2 hrs followed by topical application of the cream This is repeated 3 times during day. At night, continuous 8 hr application of the aqueous protein is administered in an occlusive dressing. Alternate day therapy is the cream applied thrice per day. At later stages of treatment, a maintenance dose of about 1-8% cream, preferably about 5% is given. This therapy may be combined with topical steroids. Maintenance therapy may be give for weeks to months, depending on the patients' response. A preferred emollient cream base is petroleum, mineral oil, mineral wax and alcohol (Aquaphor; Beiersdorf, Inc.) though other compositions known in the art may be used. Formulation is done using conventional methods.

Evidence exists for a T lymphocyte protein receptor with elastase-like character to participate in fusion of HIV-1 with permissive host cells (Bristow, C.L. et al., *International Iinmunol.* 7:239-249 (1995)). A synthetic elastase inhibitor (MAAPVCK: methoxysuccinyl-Ala-Ala-Pro-Val (SEQ ID NO: 29)-chloromethylketone) significantly reduced HIV infectivity when present during contact between virus and cells. The human T cell elastase-like homolog is membrane-associated and is protected from bystander proteolysis by association with its natural inhibitor, α1PI. Evidence suggests ligand exchange between gp41-gp120-CD4 complexes and elastase-like protease-α1PI complexes. Complexes between gpl20 and CD4 may induce dissociation of elastase and α1AT. and disruption of the latter complexes may explain ability of MAAPVCK to interfere in HTV infectivity. Blocking the catalytic site of elastase-like protease would preempt HIV fusion. Therefore the compositions of the present invention are useful to target such complexes, inhibit the elastase-like activity, and thereby contribute to the antiviral effect on HIV.

Atherosclerosis, Restenosis and Vascular Disease

Atherosclerosis and the formation of neointimna in blood vessels, especially in arteries, is stimulated by a number of events, including platelet activation leading to thrombosis and secretion growth factors, as well as stimulation of SMC migration and proliferation resulting in neointima formation (see, for example, Reidy, M. A. et al., *Circulation* 86III:43, 46 (1992); Jackson, C. L. et al., *Arterioscler. Thromb.* 13:1218-1226; Matsuno, H. etal., *Nippon Yakurigaku Zasshi* 106:143-155 (1995)). Peptides containing the RGD sequence, chief among them Vn, can prevent the binding of several integrins including $\alpha_v\beta3$ in SMC migration. By inhibiting integrin function, particularly the binding of $\alpha_v\beta3$ (also referred herein to as Vn receptor or VnR), the formation of neointima is inhibited as a consequence of lowering the percentage SMC migrating into and proliferating in the vascular media and neointima. The PAI-1 mutant proteins of the present invention, by blocking integrin interaction with Vn, are useful in reduction of thrombus and neointima formation, thereby preventing the generation of atherosclerosis.

Restenosis, the narrowing that occurs in certain patients as a result of neointimal SMC accumulation after balloon angioplasty as a treatment for end-stage atherosclerosis, is an important long term complication. Its incidence is about 30 to 50% within six months post-angioplasty (Libby, P. et al. *Circulation* 86:ffi 47-52 (1992); Groves, P. H. et al. *Atheroscler.* 117 83-96 (1995); Nikol, S., *Wien Klin Wochenschr.* 107:379-89 (1995). From animal models it is known that restenosis takes place in several phases: thrombosis, inflammation, cell-proliferation and matrix formation. The process is complex, with various factors interacting in each phase as agonists or antagonists. After more than 15 years experience in balloon angioplasty, there is an urgent need to develop therapeutic strategies based on currently available information. A number of approaches have been suggested, including selective elimination or alteration of proliferating cells, enhancement of natural growth inhibitors, blocking of signal transduction or inhibition of the gene expression for distinct growth stimulating proteins. The present invention provides a specific approach directed at disrupting the adhesion, migration and subsequent proliferation of SMC in the vasculature by providing a PAI-1 mutant capable of inhibiting these steps by binding to Vn and disrupting Vn interactions with its integrin receptors on cells.

Groves et al., supra described a quantitative pig carotid artery model which can be used in the evaluation of the present mutant PAI-1 compositions and which reflects two distinct kinds of injury which occur in human disease: medial dilation and deep medial tearing with rupture of the internal elastic lamina. In this model the time course of neointima formation is evaluated morophometrically and SMC proliferation is measured by immunocytochemical detection of the "proliferating cell nuclear antigen" (PCNA) at various times after balloon injury. In this model dilatation injury causes medial enlargement and neointima formation by 7 days, as does rupture of the internal elastic lamina. Balloon injury increases the PCNA index of SMCs in the media underlying an intact internal elastic lamina maximally after three days, and in the neointima and in the neomedia after 7 days.

A recently described improved model of human restenosis in monkeys utilizes atherosclerotic monkeys fed an atherogeruc diet for 36 months (Geary, R L. et al., *Arterioscler Thromb. Vasc. Biol.* 16:3443 (1996). Angioplasty is performed in one iliac artery. At varying time points (up to 28 days), proliferating cells are enumerated using bromodeoxyuridine labeling and arteries may be fixed in situ for examination. It has been observed that angioplasty often fractures the intimal plaque andmedia, transiently increasing the lumen caliber and artery sizes, which commonly returns to baseline by 7 days. Proliferation was increased throughout the artery wall at 4 and 7 days and declined later to control rates. The intimal thickened markedly from 14 to 28 days. This response to angioplasty closely resembles that in humans. PAI-1 mutants according to this invention are given to monkeys in conjunction with the angioplasty to evaluate dose and administration regimens. The results may be applied directly to human subjects or other mammalian species.

Libby et al., supra, discussed restenosis mechanisms based on a cytokine/growth factor cascade following angioplasty. Acute local thrombosis and/or mechanical injury triggers cytokine/growth factor gene expression by resident macrophages and SMCs which evokes a secondary growth factor and cytokine response that could amplify and sustain the proliferative response. Human atheromas contain variable numbers of macrophages. The variability in macrophage content of atheromas which may determine the propensity to develop restenosis could explain why all lesions do not restenose. In the context of these mechanisms, the PAI-1 mutant proteins, by inhibiting Vn-dependent SMC migration, would prevent or reduce the deranged behavior of SMCs during restenosis triggered by vascular injury.

Studies with transgenic mice over- or under-expressing components of the fibrinolytic system revealed a significant role in fibrin clot surveillance, reproduction, vascular wound healing, brain function, health and survival (Carmeliet, P. F., *Baillieres Clin Haematol* 8:391401 (1995)). Over time, both types of PAs appear to have evolved with specific yet overlapping biological properties. Loss of PA gene fumction is thought to be important in atherosclerosis, neoangiogenesis, inflammatory lung and kidney disease and malignancy. The PA knockout mice with their thrombotic phenotypes allowed study of the restoration of normal thrombolytic function and prevent thrombosis by gene transfer of wild type or mutant PA genes. Impaired thrombolysis of tPA-deficient mice was restored using viral-mediated gene transfer of recombinant tPA. Analysis of neointima formation in PA-deficient mice suggested that controlled reduction of fibrinolytic activity in the vessel wall might be beneficial for prevention or reduction of restenosis. This model permits evaluation of the present PAI-1 mutants, either by gene transfer or exogenous therapy, in preventing fibrinolytic processes as well as inhibiting cell migration as discovered by the present inventors.

Sawa, H. et al., *J. Am. Coll. Cardiol* 24:1742-1748 (1994), examined rabbit carotid arteries to test whether altered gene expression of PAI-1 occurred within the arterial wall after experimental balloon injury. Balloon injury (as a model for angioplasty) induced intramural PAI-1 expression (mRNA and protein) in vascular SMCs and ECs. The decreased cell surface fibrinolytic activity likely to result from the increased PAI-1 expression may initiate or exacerbate mural thrombosis. As a consequence, excessive stimulation with clot-associated mitogens may stimulate vascular SMC proliferation, which, coupled with increased accumulation of ECM attributable to a decreased plasma-mediated degradation, may contribute to restenosis.

The present invention provides a means to avoid or prevent the aforementioned events which involve PAI-1 in the pathogenetic process. By providing to a subject a PAI-1 mutant with high affinity for Vn, the Vn-dependent migration of SMCs is reduced or prevented, thereby avoiding the subsequent proliferation which contributes to the restenosis.

Cancer, Angiogenisis and Fibrosis

Work by Cheresh and colleagues has provided an insight into the various types of VnR integrins and their role in various biological reactions of clinical importance. Of particular importance to the present therapeutic methods are the interactions between the VnR $\alpha_v\beta_3$ and Vn, which are inhibitable by various of the PAI-1 mutants of this invention. By preventing interaction of these adhesion molecules, the important process of cell migration can be diminished or halted, with a number of important consequences for those diseases and conditions associated with undesirable cell migration, which leads to proliferation and pathogenesis. In addition to the vascular phenomena and diseases discussed above, such migration is important in tumor invasion and metastasis, which can be suppressed by the present compositions and methods. Furthermore, as detailed below, angiogenesis and neovascularization is dependent upon intact VnR-Vn interactions. Thus, disruption of cell binding to Vn by PAI-1 mutants will inhibit angiogenesis, an effect which can be harnessed to inhibit both local and metastatic tumor growth.

Homologous integrins with identical a subunits and structurally distinct β subunits result in different functional recognition repertoires among various cell types. For example, carcinoma cells were described as expressing an novel VnR integrin ($\alpha_v\beta_x$) which mediated cell adhesion to Vn, but not to fibrinogen or von Wdlebrand factor (Cheresh, D. A et al., *Cell* 57:59-69(1989)). In contrast, melanoma and ECs express a VnR ($\alpha_v\beta3$) that promotes cell attachment to all of these matrix components. The carcinoma cell integrin was composed of an α subunit indistinguishable from the $\alpha_v$ of the VnR and a previously unrecognized β subunit ($\beta_x$). These cells also lacked mRNA encoding integrin $\beta_3$. This variant receptor mediated cell adhesion to Vn as well as fibronectin based on antibody inhibition studies.

Integrin α chains can complex with more than a single β chain in the same cell (Krissansen, G. W. et al., *J. Biol. Chem.* 265:823-830 (1990)). Differential regulation of expression of the different β subunits that associate with the VnR α chain may play a role during cell differentiation of monocyte-macrophages.

Important for this invention is the discovery of the requirement for the integrin β3 subunit for carcinoma cells to spread or migrate on Vn (and fibrinogen) (Leavesley, D. I. *J. Cell Biol.* 117:1101-1107 (1992)). A human pancreatic carcinoma was found to use integrin $\alpha_v\beta5$ as its primary VnR as it failed to express $\alpha_v\beta_3$. These cells could not form focal contacts, spread or migrate on Vn but readily did so on collagen in a $\beta_1$ integrin-dependent manner. Transfection of these cancer cells with cDNA encoding the integrin $\beta_3$ subunit caused surface expression of a functional $\alpha_v\beta_3$ heterodimer providing these cells with novel adhesive and biological properties, namely the capacity to attach and spread on Vn or fibrinogen with $\beta_3$ localization to focal contacts. These cells gained the capacity to migrate through a porous membrane in response to either Vn or fibrinogen. These results demonstrated that the $\beta_3$ and $\beta_5$ integrin subunits, when associated with $\alpha_v$, promote distinct cellular responses to a Vn extracellular environment. According to this invention, all of the foregoing interactions between tumor ceuls and ECM are inhibitable by the PAI-1 mutants.

It is important to note that several different integrins are present on the same cells (e g., $\alpha_v\beta_1$, $\alpha_v\beta_3$ and $\alpha_v\beta_5$. However, it is the $\beta_3$ chain which is upregulated when cells are about to migrate. Nevertheless, any cell which utilizes any integrin to bind to the RGD site of Vn will be inhibited in this interaction and in its subsequent migration by the PAI-1 mutants described herein.

The requirement for vascular integrin $\alpha_v\beta_3$ for angiogenesis was shown by Brooks, P. C. et al., *Science* 264:569-571 1994). This VnR was expressed on blood vessels in wound granulation tissue and increased in expression during angiogenesis. An antibody to $\alpha_v\beta_3$ blocked angiogenesis induced by cytokines, growth factors and fragments of melanoma tumor. This identifies $\alpha_v\beta_3$ as a therapeutic target for diseases characterized by neovascularization. The present invention provides a therapeutic composition and method aimed at this target: PAI-1 mutants which are designed to inhibit migration and which maintain high affinity for Vn. Administration of effective amounts of these compositions will disrupt the molecular interactions required for angiogenesis. It is preferred to administer the compositions to the affected tissue, for example by intralesional injection into tumors, or by specific targeting using targeted liposomes.

Wound healing requires a coordinated influx of fibroblasts, vascular endothelium and epithelium. Agents which promote a more rapid influx of fibroblasts, endothelial and epithelial cells into wounds should increase the rate at which wounds heal. However, such stimulation may also result in unwanted tissue fibrosis and scarring. The PAI-1 mutants of the present invention preferably applied topically are useful in downregulating the influx of, for example, fibroblasts into a wound. Judicious use of these proteins will allow a balance to be achieved between wound healing and fibrosis or scarring.

Fibrosis in the lung is a major problem in chemotherapy with agents such as bleomycin and adriamycin. Fibroblasts migrate into the lung tissue (or other chronically inflamed tissue) on a fibrin matrix and lay down collagen. Endogenous PAI-1 bound to the fibrin matrix is displaced to allow these processes. Knockout mice overexpressing PAI-1 showed inhibition of lung fibrosis in response to bleomycin (Eitzman, D. T. et al., *J. Clin. Invest.* 97:232-237 (1996)). Pathogenesis of lung fibrosis as well as fibrosis in other chronically inflamed tissues involves increases in tissue factor which stimulates prothrombin activation to thrombin which results in fibrinogen conversion to fibrin and fibrin deposition. Inflammation also upregulates PAI-1. However, cells such as fibroblasts are able to displace PAI-1 in binding to and migrating along the fibrin matrix. Ultimately, their migration and secretion of collagen results in fibrosis. The PAI-1 mutant protein of this invention are used to disrupt this process by inhibiting the cell:matrix interaction and inhibiting fibroblast migration and generation of fibrosis in the lung or any other chronically inflamed tissue. The protein may be administered as an aerosol or by systemic injection or both. Alternatively, the protein may be targeted to a specific tissue by liposome carriers or other means known in the art for targeted drug delivery.

Thrombosis

Mutant PAI-1 proteins also serve as improved thrombin inhibitors. Thrombin bind to fibrin in a clot is protected from inhibition by normal thrombin inhibitors. The mutant PAI-1 proteins are able to inhibit such "protected" thrombin on surfaces In this way, the mutant PAI-1 compositions are used to treat deep venous thrombosis, where clot-bound thrombin serves to promote extension of the clot leading to blockage and myocardial infarction, for example Clot extension is resistant to traditional anticoagulant therapy. Administration of PAI-1 mutant protein will clear thrombin from a clot and thereby prevent clot extension and its pathologic sequelae.

Having now generally described the invention, the same will be more readily understood through reference to the following examples which are provided by way of illustration, and are not intended to be limiting of the present invention, unless specified.

EXAMPLE I

Inhibition of Elastase by PAI-1 Mutants

Studies were performed to test the ability of PAI-1 mutants to bind to elastase in a manner which permitted inhibition elastase enzymatic activity. Also tested was the ability of the PAI-1 mutant to stimulate endocytosis of elastase the dependence of this internalization on LDL-like receptor proteins.

Assay for Elastase Activity and its Inhibition

Neutrophil elastase and pancreatic elastase (1 µg/ml) were incubated with increasing concentrations of either wtPAI-1 or P1-Ala-PA-1, or α1AT for 30 min at room temperature in 50 mM Tris pH 7.5, 150 mM NaCl, 100 µg/ml BSA, 0.01% Tween-80 (100 µl). The chromogenic substrate Ala-Ala-Ala-pNA (Sigma) (100 µl) was added to 1 mM final concentration. The change in absorbance at 405 nm was measured at 37° C. for 30 min., and the rate of change was calculated for the last 15 min.

SDS-PAGE Analysis of Complex Formation between PAI-1 and Elastase

Neutrophil elastase (0.45 mg/ml) and pancreatic elastase (1 mg/ml) was incubated with a 4-fold molar excess of either wild-type PAI-1 (lanes 2 and 4) or P1-Ala-PAI-1 (lanes 3 and 6) for 30 minutes at room temperature and then samples were electrophoresed on a 12.5% SDS gel and stained with Coomassie blue.

Endocytosis of $^{125}$I-neutrophil Elastase by Type II Pneumocytes

Type II pneumocytes in 12 well plates (0.5-1×10$^6$ cells/well) were washed twice in serum-free medium and incubated for 30 min in serum-free medium+1.5% BSA. $^{125}$I-elastase from neutrophils (5 nM) was added to each group in the presence or absence of 1 mM of the receptor associated protein ("RAP") which inhibits binding of all ligands to the LDL-receptor-related protein (LRP). Cells were incubated for 30 min at 37° C. before the P1 Ala PAI-1 mutant or α1AT ("α1") (25 nM) were added to the wells. Cells were incubated for 4 hours at 37° C. Wells were washed twice using PBS and incubated for 5 min in serum-free medium containing 0.5 mg/ml trypsin and proteinase K and 0.5 mM EDTA. Cells were centrifuged and the radioactivity in the cell pellet was counted as a measure of internalized elastase.

Results

Figure 5:
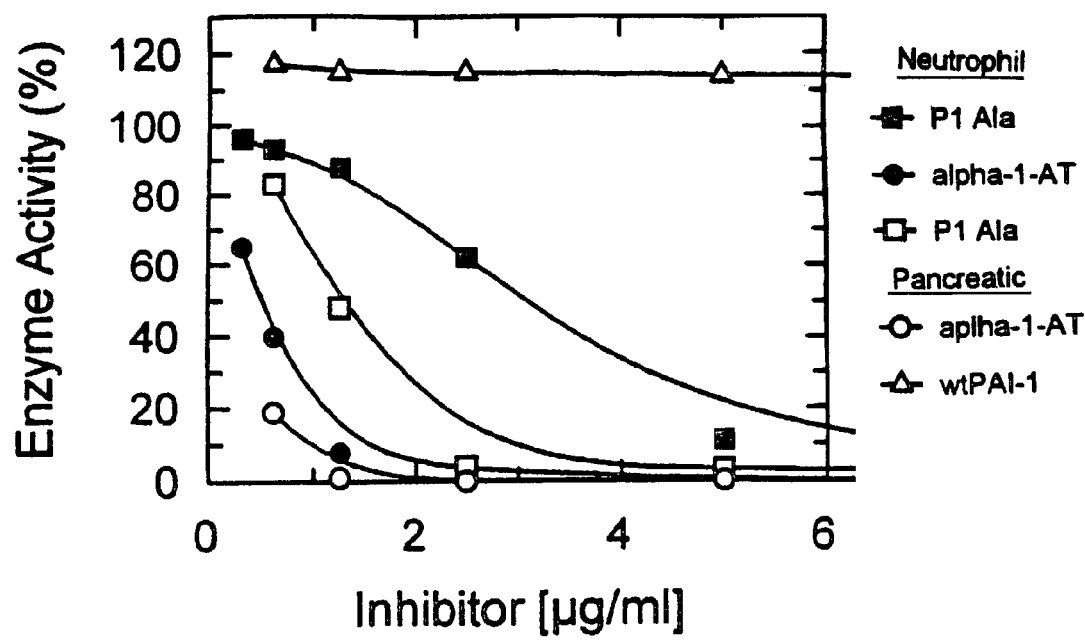
FIG. 5 is a graph showing the inhibition of neutrophil or pancreatic elastase by wtPAI-1, α1AT or P1 Ala-PAI-1. The ordinate represents the residual enzymatic activity following 30 min. incubation with increasing concentrations of the inhibitor.

Whereas wtPAI-1 did not inhibit pancreatic elastase (FIG. 5), the P1 Ala mutant PAI-1 did, although with less potency than α1AT. As for neutrophil elastase, both wild type and mutant PAI-1 inhibited enzymatic activity, with the mutant showin aout four-fold greater inhibitory capacity.

Figure 6:
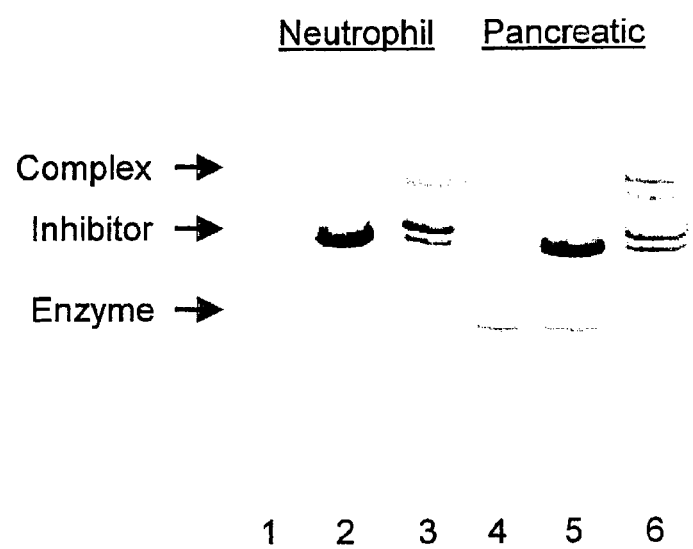
FIG. 6 shows the results of polyacrylamide gel electrophoresis (12.5% SDS-gels) of mixtures of elastase with wtPAI-1 or P1 Ala PAI-1. Lanes 1-3: neutrophil elastase. Lanes 1 & 4: elastase alone. Lanes 2 & 5: elastase+wtPAI-1. Lanes 3 & 6: elastase+P1 Ala PAI-1. The gels were stained with Coomassie blue. Bands can be seen representing the elastase enzyme, the inhibitor or the enzyme-inhibitor complex.

SDS-PAGE (FIG. 6) of mixtures of elastase with wtPAI-1 or P1 Ala PAI-1 showed the presence of the elastase and the inhibitor when wtPAI-1 was used, with no evidence of complex formation. In contrast, P1 Ala PAI-1 formed complexes with the elastase. Doublets indicate cleaved products which are still inhibited.

Figure 7:
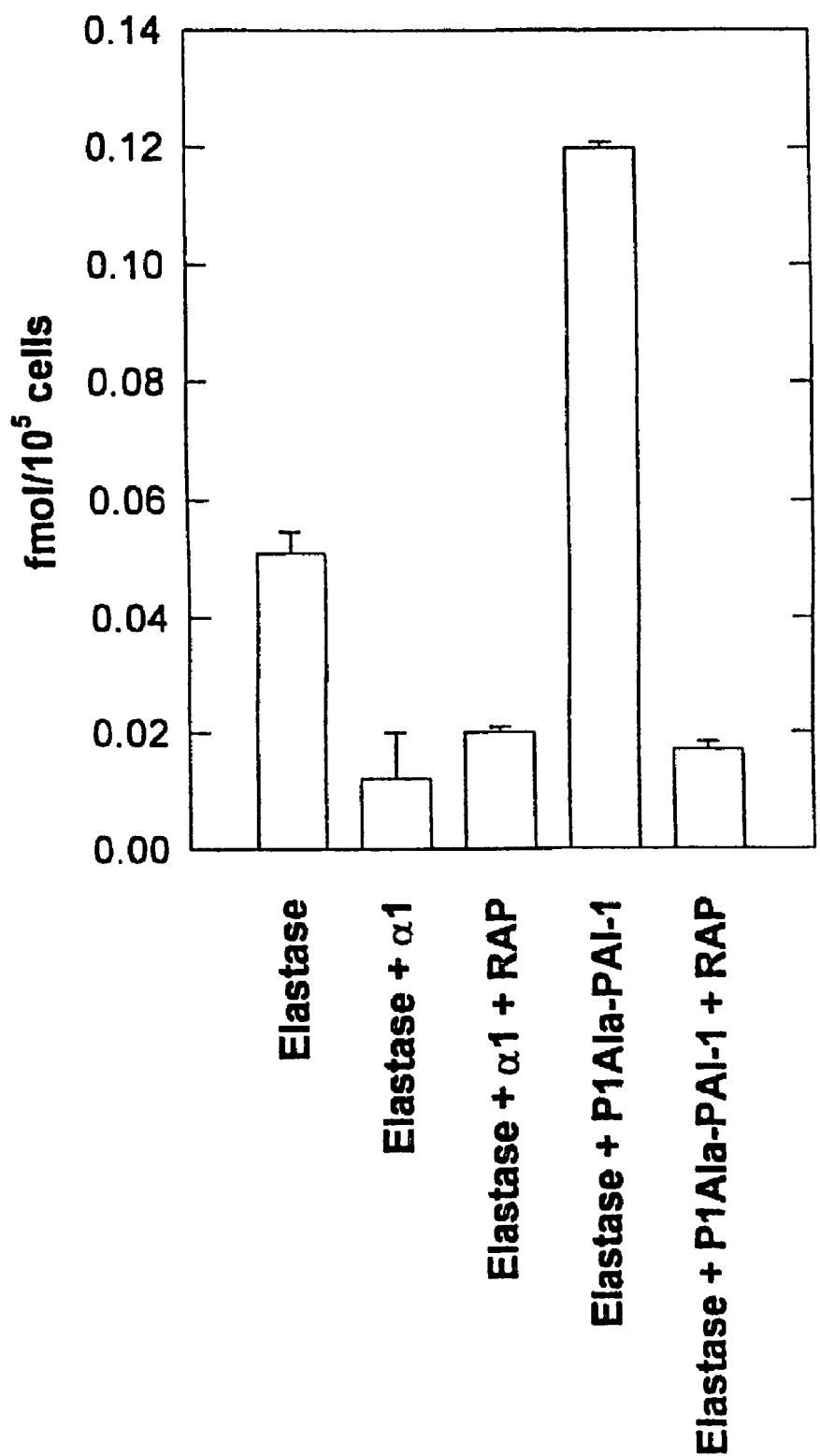
FIG. 7 is a graph showing the effect of the PAI-1 P1 Ala mutant on internalization of $^{125}$I-human neutrophil elastase by type II pneumocytes.

As for internalization (clearance) of elastase, α1AT did not promote, and even inhibited the internalization. RAP had no effect on this inhibition. In contrast, P1 Ala PAI-1 caused marked increase in elastase internalization, which was sensitive to the LRP inhibitor (FIG. 7). It was concluded that the PAI-1 mutant stimulated endocytosis and uptake of through the LDL-related clearance receptors.

EXAMPLE II

PAI-1 and Vitronectin Promote the Cellular Clearance of Thrombin by LDL-Receptor Related Proteins 1 and 2

(see: Stefansson et al., *J. Biol. Chem.* 271:8215-8229 (1996 Apr. 5)

The following study evaluated cell-mediated endocytosis as a potential mechanism for regulating levels of extravascular thrombin and determined whether PAI-1, Vn and receptors of the LDLR family have roles in the process.

I. Materials and Methods

Proteins

Human α-thrombin was obtained from Dr. F. Church (University of North Carolina, Chapel Hill, N.C.) or purchased from Enzyme Research Laboratories (South Bend, Ind.). Human HCII was obtained from Dr. F. Church. Human ATIII was obtained from Dr. K. Ingham (American Red Cross, Rockville, Md.). Human α$_1$AT was purchased from Sigma Chemical Co. (St. Louis, Mo.). Human fibrinogen was purchased from Enzyme Research Laboratories (South Bend, Ind.). D-phenylalanyl-L-prolyl-L-arginine chloromethyl ketone (PPACK) was purchased from Calbiochem (La Jolla, Calif.). Human 39 kDa receptor associated protein (RAP) was expressed and purified as described (Williams, S. E., et al., (1992) *J. Biol. Chem.*267: 9035-9040). Low density lipoprotein receptor-related protein (LRP-1) was purified as described (Ashcom, J. D., et al., (1990) *J. Cell. Biol.* 110: 1041-1048). Glycoprotein 330/ (LRP-2) was purified as previously described (Kounnas, W S. et al., (1994) *Ann. NY Acad. Sci.* 737:114-124). Native human Vn was provided by Dr. D. Mosher (University of Wisconsin, Madison, Wis.). Urea denatured human Vn (conformationally altered) was provided by Dr. T. J. Podor (McMaster University, Hamilton, Ontario, Canada). Human uPA was provided by Dr. J. Henkin (Abbott Laboratories, Abbott Park, Ill.), Bacterially expressed human PAI-1 was purchased from Molecular Innovations (Royal Oak, Mich.). A mutant form of PAI-1 having a $Gln_{123}$ to Lys substitution that makes it unable to bind to Vn (Lawrence, et al., (1994) supra) was prepared as described (Kvassman, J. D. et al., J. D. (1995) *Fibrinolysis* 9:215-221).

Radioiodination of proteins was performed by using IODO-GEN (Pierce Chemical Co., Rockford, Ill.). Complexes of thrombin and various inhibitors were prepared by incubating the $^{125}$I-thrombin with each inhibitor at a 2:1 molar ratio for 30 min at 25° C. followed by absorption of free thrombin by chromatography on a column ATIII-Sepharose (2 mg ATIII/ml resin). To prepare active site inhibited thrombin, $^{125}$I-thrombin (100 nM) was incubated with PPACK (5 mM) for 30 min at 25° C. in TBS. The complexes were tested for thrombin activity by incubation with a fibrinogen solution (1 mg fibrinogen/ml in TBS, 5 mM $CaCl_2$) at 25° C. for 30 min and assaying for fibrin formation.

Antibodies

The rabbit antisera against LRP-1 (rb777 and rb810), LRP-2 (rb239 or rb784), and a synthetic peptide corresponding to the 11 C-terminal residues of the cytoplasmic domain of LRP-1 (rb704) have been described previously (Kounnas, W. S. et al., (1994) *Ann. NY Acad Sci.* 737:114-124; Kounnas, M. Z. et al., (1992) *J. Biol. Chem.* 267:12420-12423; Strickland, D. K. et al., (1991) *J. Biol. Chem.* 266:13364-13369). Receptor-specific IgG were selected from the LRP-1 and LRP-2 sera by chromatography on columns of either LRP-1 or LRP-2-Sepharose (1-2 mg receptor/ml resin). Control rabbit IgG was purified from non-immune sera. IgG from each preparation was purified by affinity chromatography on protein G-Sepharose and absorbdeon a column of RAP-Sepharose (2 mg RAP/ml resin). Rabbit anti-murine PAI-1-serum was from Molecular Innovations (Royal Oak, Mich.).

Cells

Rat pre-type II pneumocytes (Mallampalli R. K., et al, (1992) *In Vitro Cell. Dev. Biol.* 28A: 181-187) were grown in Waymouth's media (Gibco) supplemented with 10% bovine calf serum (Hyclone, Logan, Utah), penicillin, and streptomycin.

Solid Phase Binding Assays

Solid phase binding assays were performed as described (Williams, S. E., et al. (1992) *J. Biol. Chem.* 267:9035-9040). $^{125}$I-thrombin:PAI-1 complexes (1 nM) in the presence of increasing concentrations of unlabeled complex or RAP were incubated with microtiter wells coated with LRP-1, LRP-2 or BSA (3 µg/ml). The program "Ligand" was used to analyze the competition data and to determine dissociation constants ($K_d$) for receptor-ligand interactions.

Endocytosis and Degradation of Thrombin and uPA

Type II pneumocytes were seeded into wells of 12-well plates (1-2.5×10$^5$ cells/well) and grown 18 h at 37° C., 5% $CO_2$ in Waymouth's medium containing 10% bovine calf serum. Before addition of $^{125}$I-thrombin:inhibitor complexes, the cells were washed twice in serum-free Waymouth's medium and incubated for 30 min in medium containing 1.5% BSA, 20 mM Hepes pH 7.4, Nutridoma serum-substitute, penicillin, and streptomycin (assay medium). $^{125}$I-complexes in assay medium were added to cell layers and incubated for 4-6 h at 37° C. Where indicated, unlabeled thrombin:PAI-1 (800 nM), RAP (1 µM) or IgG (150 µg/ml) were added 30 min prior to addition of $^{125}$I-ligand and were kept present during the assay. The quantitation of the amount of endocytosed and degraded ligand were done as described in (Stefansson, S. et al., (1995) *J. Cell Sci.* 108: 2361-2369). Briefly, following the incubation period, the medium was removed from the cells and precipitated with 10% trichloroacetic acid. Soluble radioactivity was taken to represent degraded ligand. Cell layers were washed twice with serum-free medium and incubated in serum free-medium containing trypsin and proteinase K (0.5 mg/ml) and 0.5 mM EDTA for 2-5 minutes at 4° C. The cells were then centrifuged at 6000× g for 2 minutes and the radioactivity in the cell pellet was taken to represent the amount of endocytosed ligand.

To evaluate the effects of wild-type and mutant PAI-1 on the clearance (endocytosis and degradation) of exogenously added $^{125}$I-thrombin, cells were grown in medium containing 10% serum as described above. Washed monolayers were then incubated either with wild-type PAI-1 (10 nM) or mutant PAI-1 (10 nM) for 20 min at 37° C. $^{125}$I-thrombin (10nM) or $^{125}$I-uPA (10 nM) was added and incubated for 4-6 h at 37° C. Where indicated, RAP (1 µM) was incubated for 30 min prior to addition of the ligands.

To evaluate the effects of native versus conformationally altered Vn on the clearance of exogenously added PAI-1 and active $^{125}$I-thrombin, cells were grown in serum-free medium for 18 h at 37° C. on tissue culture plates coated with 0.1% gelatin. Medium was removed and assay medium added for 1 h at 37° C. to block unoccupied binding sites with BSA. Cell monolayers were incubated with either native (50 nM) or conformationally altered Vn (50 nM) for 1 h at 37° C. Cell monolayers were then washed twice with assay medium to remove unbound Vn. Wild-type PAI-1 (10 nM) was added and incubated for 1 h at 37° C. $^{125}$I-thrombin (10nM) or $^{125}$I-uPA (10 nM) were added and incubated for 4-6 h at 37° C.

II. Results

The efficient endocytosis and degradation of active thrombin depends on PAI-1.

Figure 8:
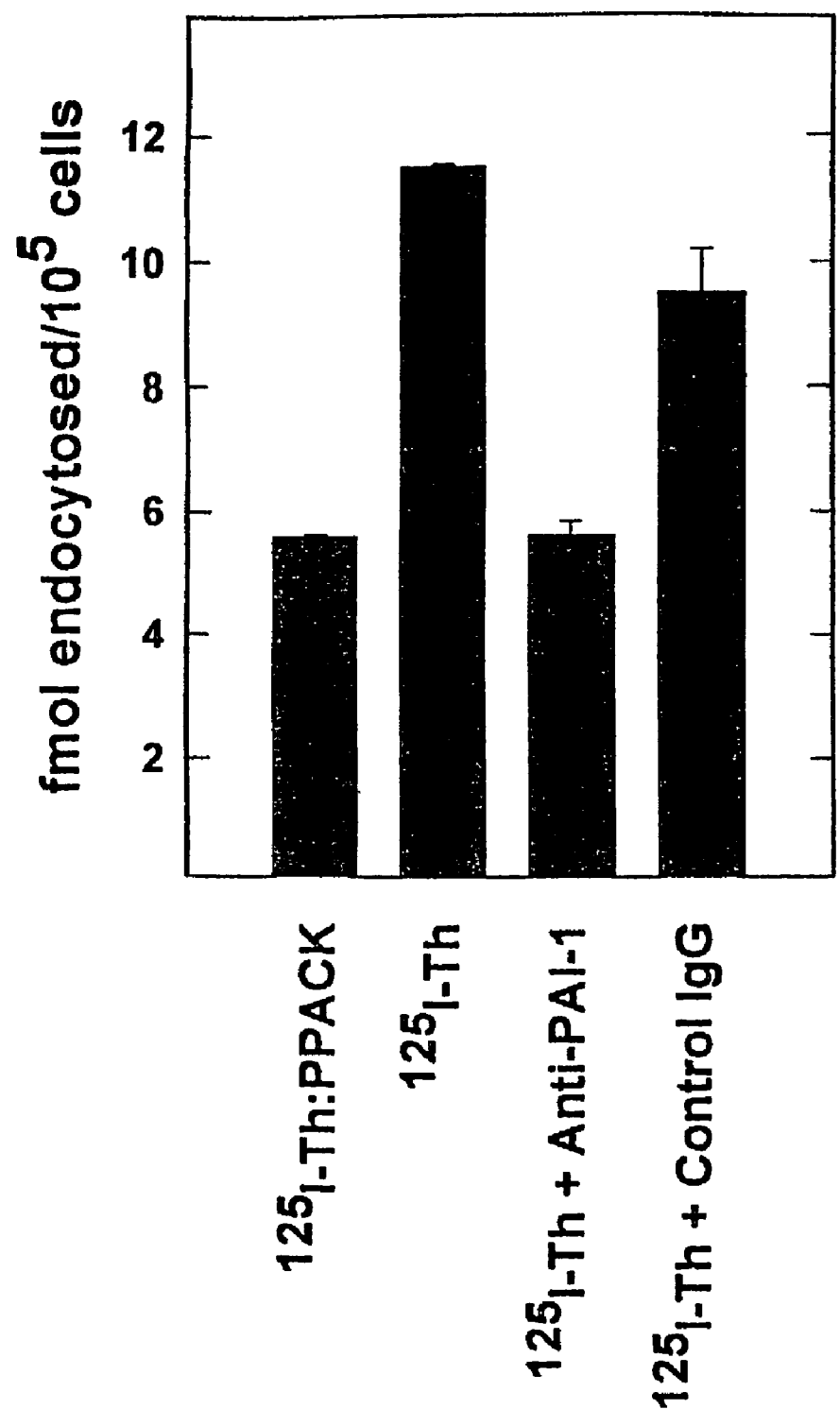
FIGS. 8 and 9 are a set of graphs showing endocytosis (FIG. 8) and degradation (FIG. 9) by pre-type II pneumocytes of active and active site-inhibited thrombin and effects of PAI-1 antibodies. $^{125}$I-thrombin;PPACK ($^{125}$I-Th:PPACK) and active $^{125}$I-thrombin ($^{125}$I-Th) each at 20 nM. Also shown in each panel are the effects of rabbit anti-mouse PAI-1 IgG (0.6 mg/ml) or normal rabbit IgG (Control IgG, 0.6 mg/ml) on active $^{125}$I-thrombin. The results represent 3 experiments each performed in duplicate. Each plotted value represents the average of duplicate determinations with the range indicated by bars.
Figure 9:
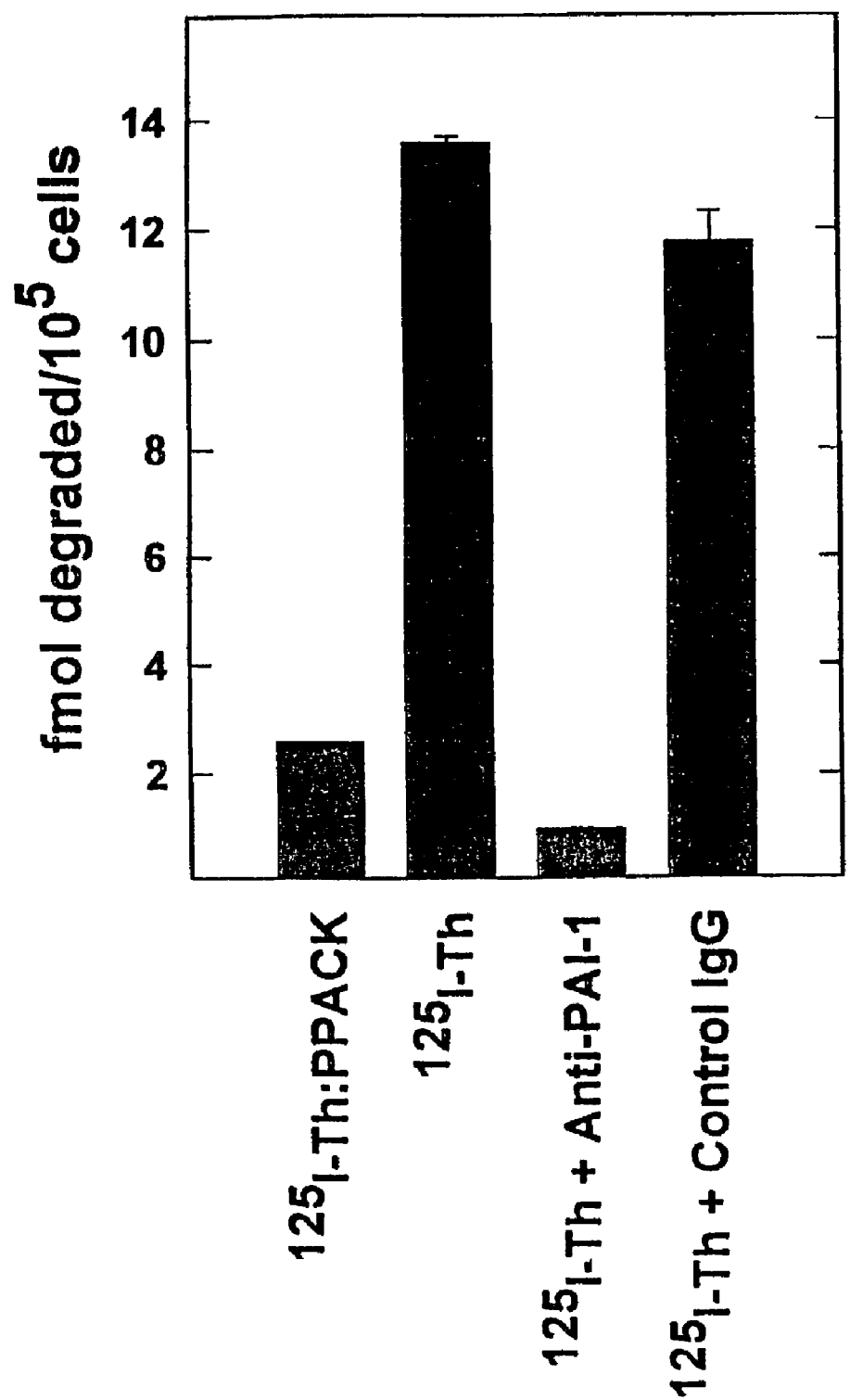

When the endocytosis and degradation of exogenously added active versus active site-inhibited $^{125}$I-thrombin was compared, the active thrombin was more efficiently endocytosed and degraded (FIGS. 8-9). Considering that the clearance of two other proteinases, tPA and uPA have been shown to be augmented by complex formation with PAI-1, the possibility that PAI-1 was mediating the clearance of the active thrombin in the cultured pre-type II pneumocyte cells was investigated. Pretreatment of cell layers with PAI-1 antibodies resulted in the inhibition of both endocytosis and degradation of active $^{125}$I-thrombin whereas control rabbit IgG had a negligible effect on either process (FIGS. 8-9). These data show that active thrombin is endocytosed and degraded and suggest that PAI-1 is involved.

Figure 10:
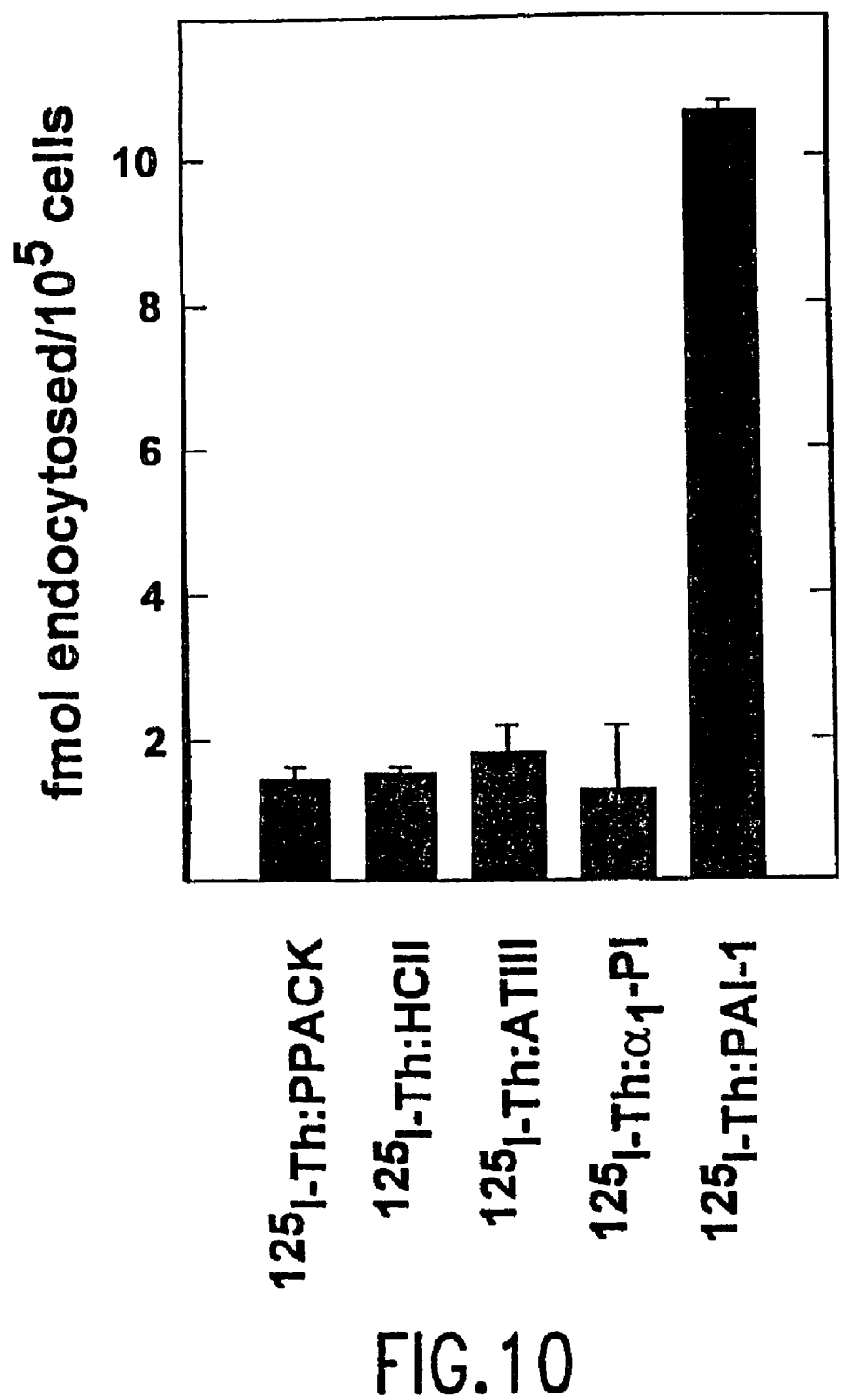
FIGS. 10 and 11 are a set of graphs comparing the level of endocytosis (FIG. 10) and degradation (FIG. 11) of $^{125}$I-thrombin in complex with serpins. Pre-type II pneumocyte cells were incubated with $^{125}$I-thrombin in complex with the synthetic inhibitor Phe-Pro-Arg-chloromethyl ketone ($^{125}$I-Th:PPACK), HCII ($^{125}$I-Th:HCII), ATII, ($^{125}$I-Th:ATIII), α$_1$PI ($^{125}$I-Th:α$_1$PI) each at 16 nM. The results represent 4 experiments. Each plotted value represents the average of duplicate determinations with the range indicated by bars.
Figure 11:
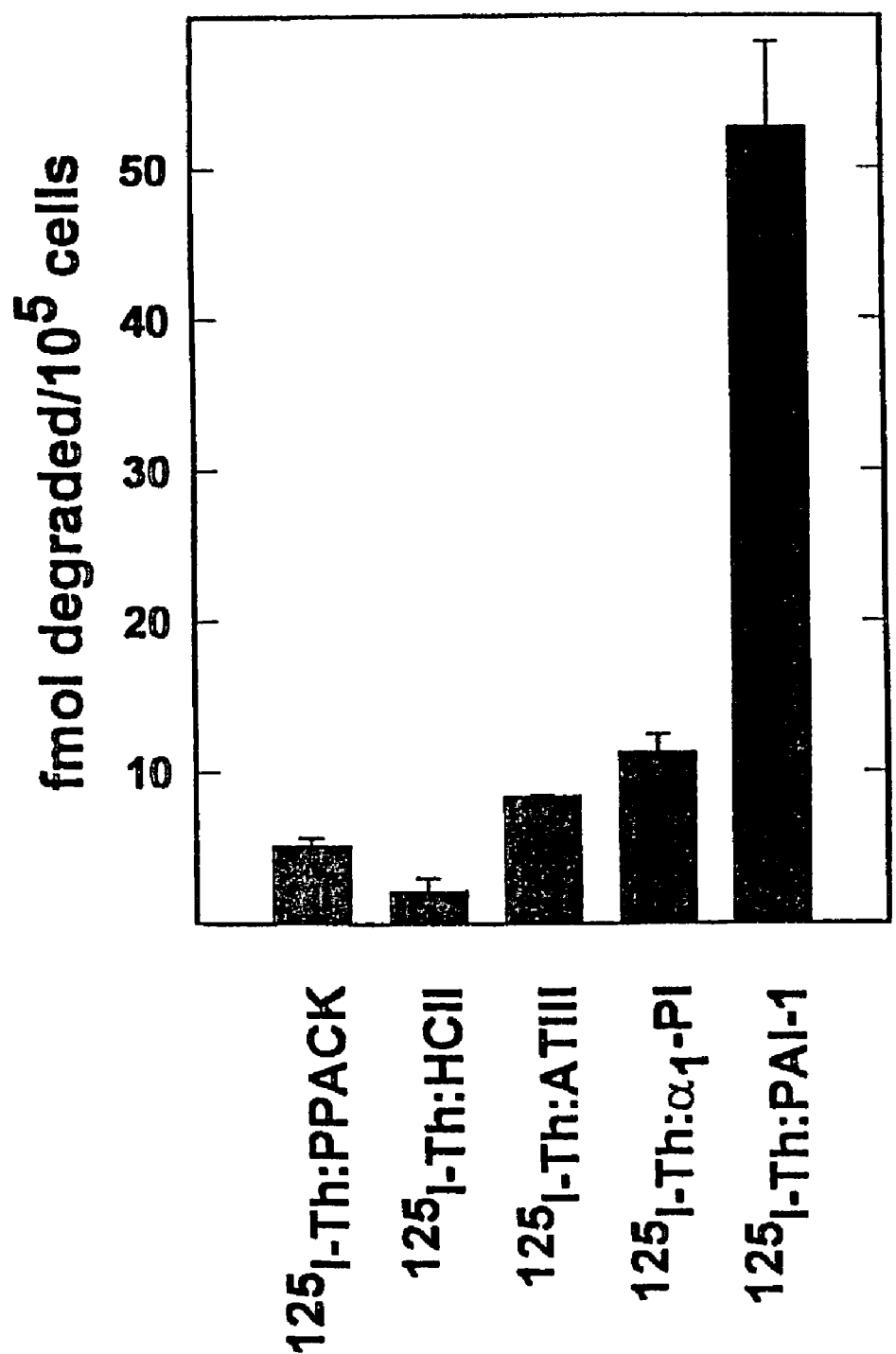

Thrombin in Complex with PAI-1 is More Efficiently Endocytosed and Degraded as Compared to Complexes with ATIII HCII or $\alpha_1$AT The relative efficiency of cell mediated clearance of $^{125}$I-thrombin in complex with various serpins was investigated using the pre-type II pneumocyte cell line. As shown in FIGS. 10-11, $^{125}$I-thrombin:PAI-1 complexes were endocytosed (panel A) and degraded (panel B) at levels six-fold greater (n=2) than complexes of thrombin and the serpins ATIII, HCII and $\alpha_1$AT or of thrombin and the synthetic peptide inhibitor PPACK.

Figure 12:
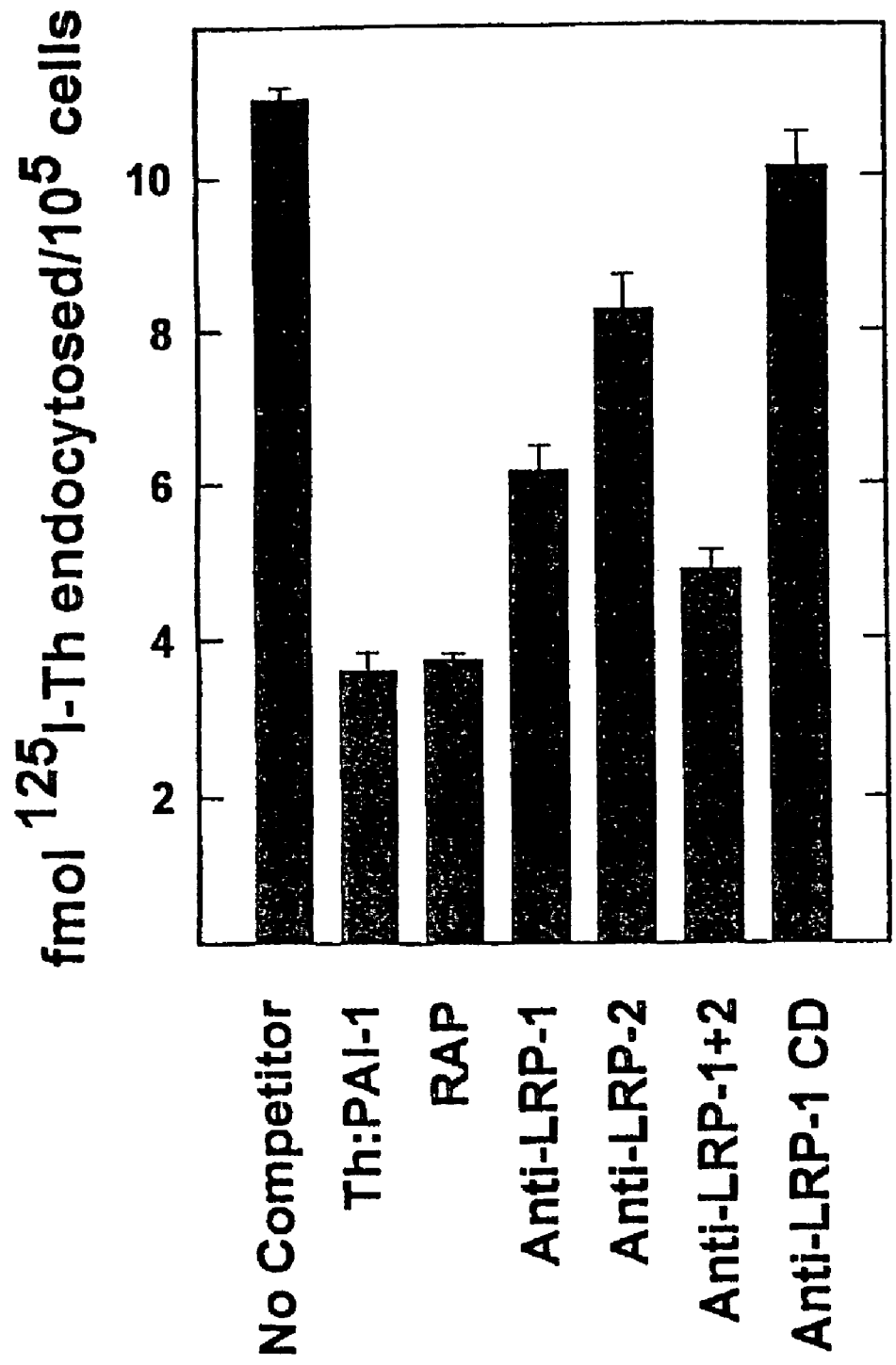
FIGS. 12 and 13 are a set of graphs comparing the level of endocytosis (FIG. 12) and degradation (FIG. 13) of $^{125}$I-thrombin:PAI-1 complex inhibited by antagonists of LRP function. $^{125}$I-thrombin:PAI-1 complex (10 nM) was incubated with cultured pre-type II pneumocyte cells in the presence of RAP (1 μM), affinity purified LRP-1 antibodies (anti-LRP-1, 150 μg/ml), affinity purified LRP-2 antibodies (anti-LRP-2, 150 μg/ml), a mixture of the LRP-1 and 2 antibodies (anti-(LRP-1+2)), 300 μg/ml) or antibody to a peptide corresponding to the cytoplasmic tail of LRP (anti-LRP-1 CD, 150 μg/ml). Specific endocytosis and degradation was determined by co-incubation with 500-fold molar excess of unlabeled thrombin:PAI-1. The results are representative of 2 experiments. Each plotted value represents the average of duplicate determinations with the range indicated by bars.
Figure 13:
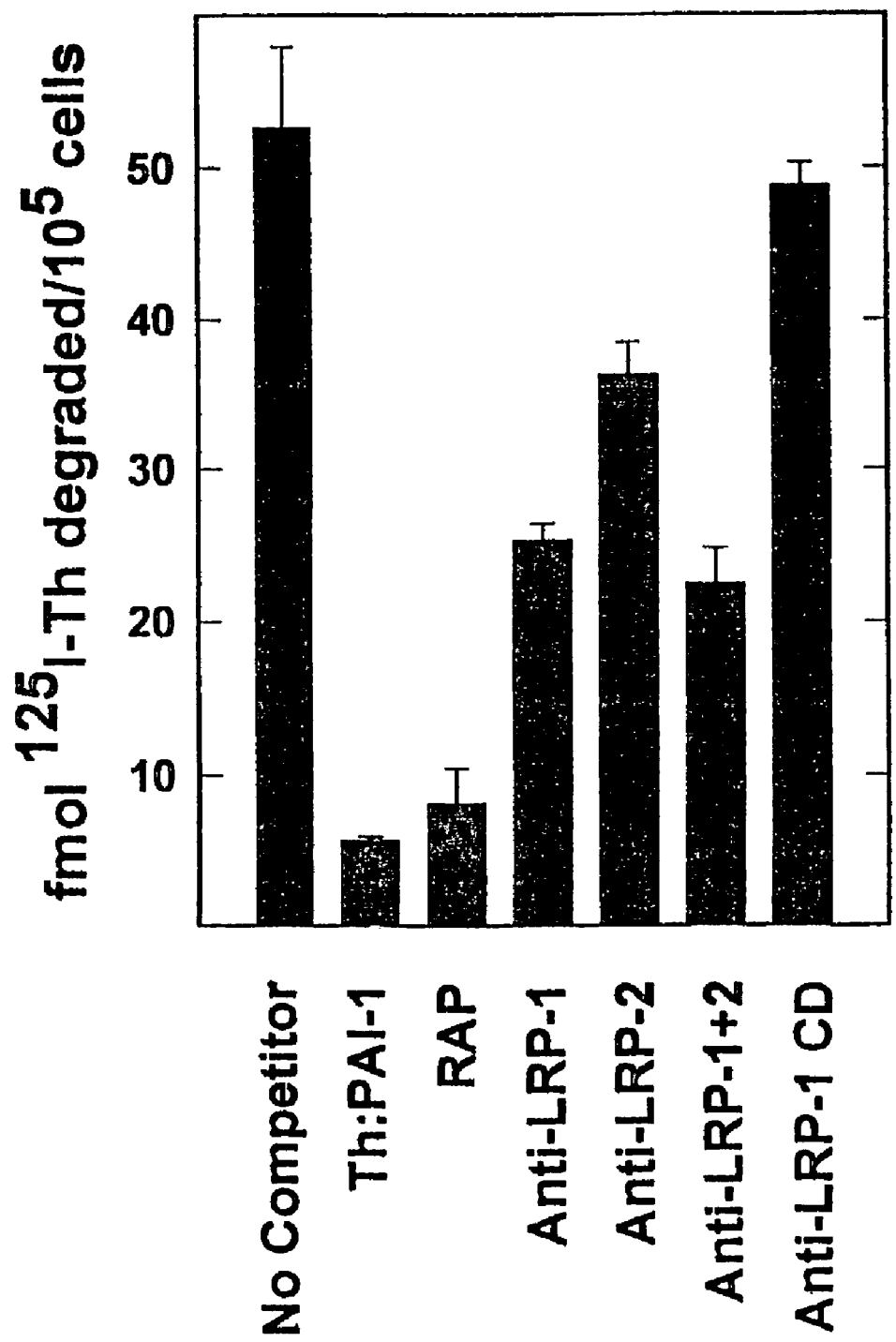

Members of the Low Density Lipoprotein Receptor Family Mediate the Endocytosis and Degradation of Thrombin:PAI-1 Complex Considering that PAI-1 facilitates the cellular clearance of active uPA via members of the LDLR family, the potential role of these receptors in the clearance of thrombin:PAI-1 with thrombin was studied. The pre-type II pneumocyte cell line was previously shown to express two members of the LDLR family, LRP-1 and LRP-2 (Stefansson, supra). As shown in FIGS. 12-13, antagonists of LRP-1 and LRP-2 function, namely the 39 kDa receptor-associated protein (RAP), and antibodies to either LRP-1 or LRP-2 each inhibited the endocytosis and degradation of $^{125}$I-thrombin:PAI-1 complex. The extent of RAP inhibition was similar to that using excess unlabeled thrombin:PAI complex suggesting that members of the LDLR family were mediating the endocytosis and degradation of thrombin:PAI.

The results indicate that at least two members of the LDLR family, LRP-1 and LRP-2 can mediate endocytosis and degradation of $^{125}$I-thrombin:PAI-1. The inability of the combination of both LRP antibodies to inhibit endocytosis and degradation to the same extent as did RAP (FIGS. 12-13) suggests that additional LDLR family expressed by the pre-type II pneumocytes are able to endocytose thrombin:PAI-1.

Thrombin PAI-1 Complex Binds LRP-1 and LRP-2 in Solid Phase Assay

Figure 15:
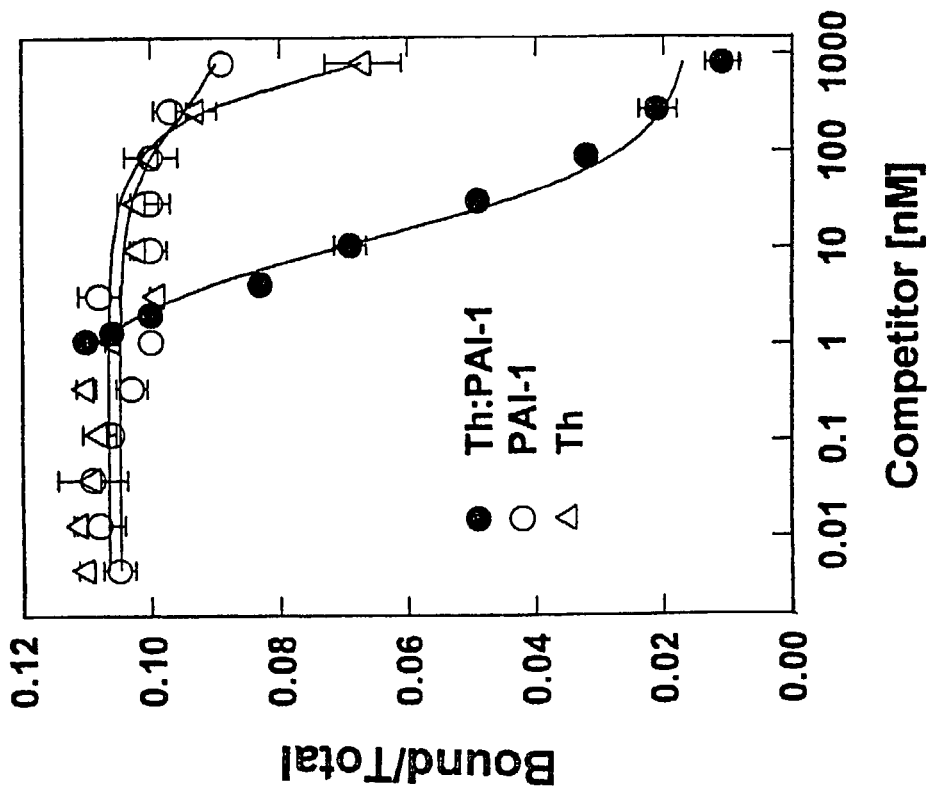
FIGS. 14 and 15 are a set of graphs showing the binding of $^{125}$I-thrombin:PAI-1 complex to LRP-1 (FIG. 14) and LRP-2 (FIG. 15). The binding was measured in the presence of increasing concentrations of unlabeled thrombin:PAI-1, thrombin or PAI-1. The curves represent the best-fit of the data to a single class of sites. The results represent 4 experiments each performed in duplicate. Each plotted value represents the average of duplicate determinations with the range indicated by bars.
Figure 14:
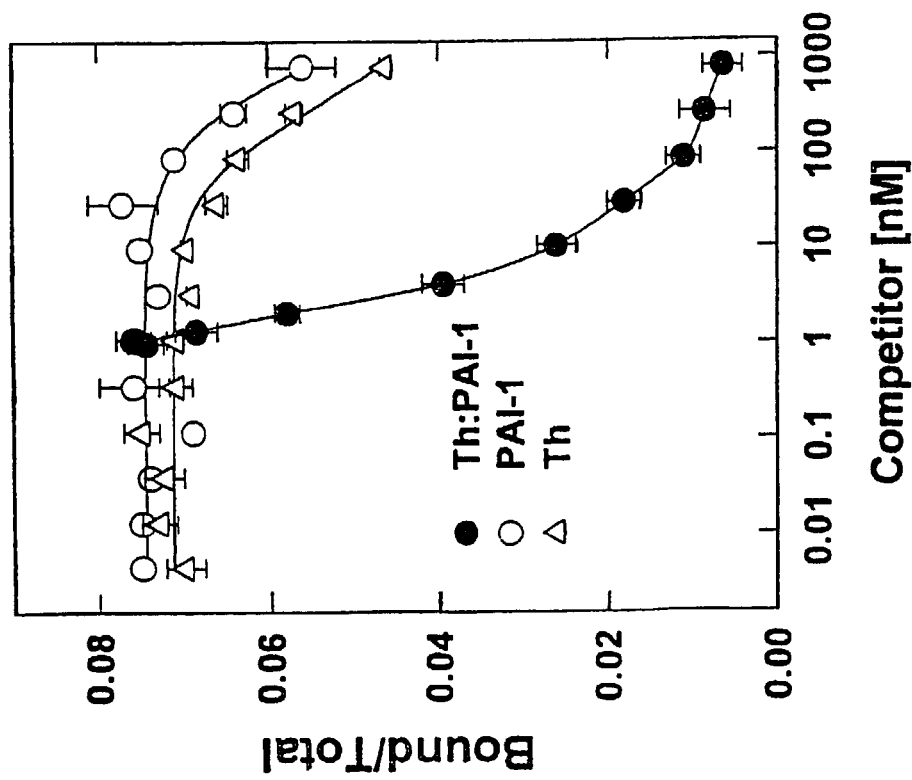

Solid phase binding assays using purified components were performed to determine whether thrombin:PAI-1 was able to bind directly to LRP-1 and LRP-2. As shown in FIGS. 14-15, $^{125}$I-thrombin:PAI-1 complex bound to microtiter wells coated with either receptor. By fitting the homologous ligand displacement data to a model of a single class of sites, dissociation constants ($K_d$) of 3.3 nM (n=3) and 13 nM (n=2) were derived for the binding of $^{125}$I-thrombin:PAI-1 to LRP-1 and LRP-2, respectively RAP was found to compete for the binding of $^{125}$I-complex to both receptors. Thrombin or PAI-1 alone did not compete efficiently for $^{125}$I-thrombin:PAI-1 binding to either receptor ($K_d$'s>700 nM).

The results indicate that thrombin:PAI-1 complex binds with high affinity to LRP-1 and LRP-2. The fact that PAI-1 binds to both receptors yet is unable to compete for thrombin:PAI-1 binding suggests that the complex possesses an additional receptor binding site not present on either thrombin or PAI-1 alone.

The Ability of PAI-1 to Bind Vn Facilitates the Efficient Clearance of Thrombin

Figure 16:
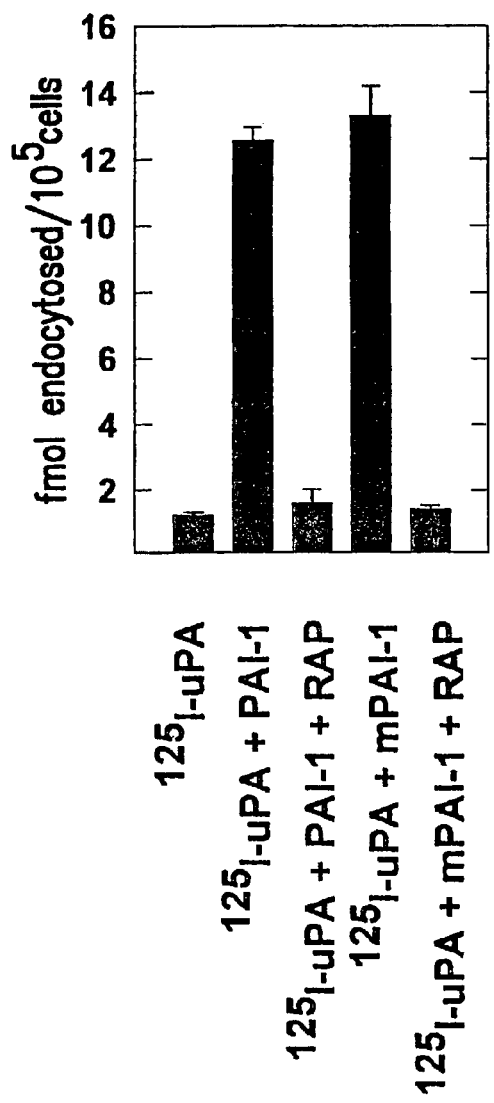
FIGS. 16-19 are a set of graphs showing the effect of wild-type PAI-1, or a mutant of PAI-1 that is unable to bind Vn, on the endocytosis and degradation of $^{125}$I-thrombin (FIGS. 16 and 18) or $^{125}$I-uPA (FIGS. 17 and 19). Pre-type II pneumocyte cells were incubated with either wild-type PAI-1 ("wtPAI-1", 10 nM) or mutant PAI-1 ("mPAI-1", 10 nM) that is unable to bind Vn. $^{125}$I-thrombin or $^{125}$I-uPA (10 nM) incubated with cells in the presence or absence of RAP (1 µM).
Figure 17:
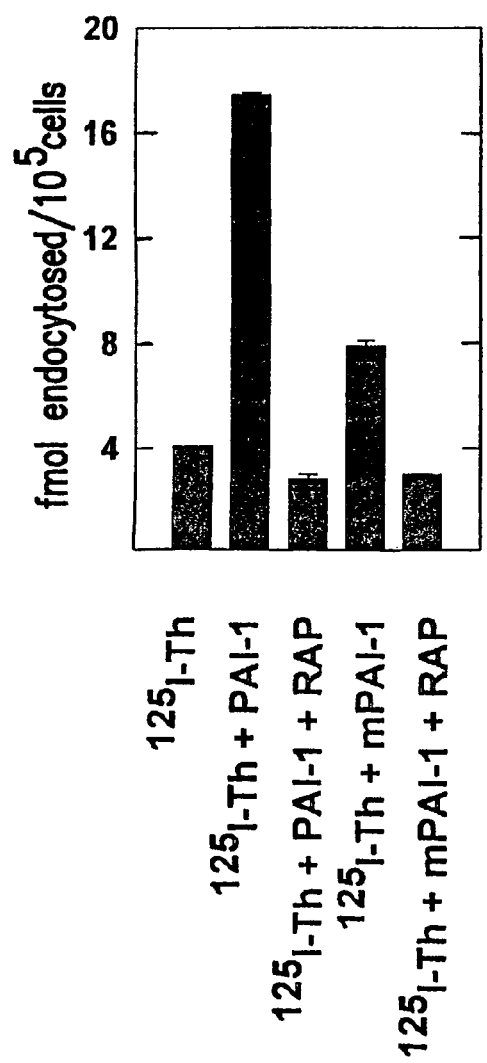
Figure 18:
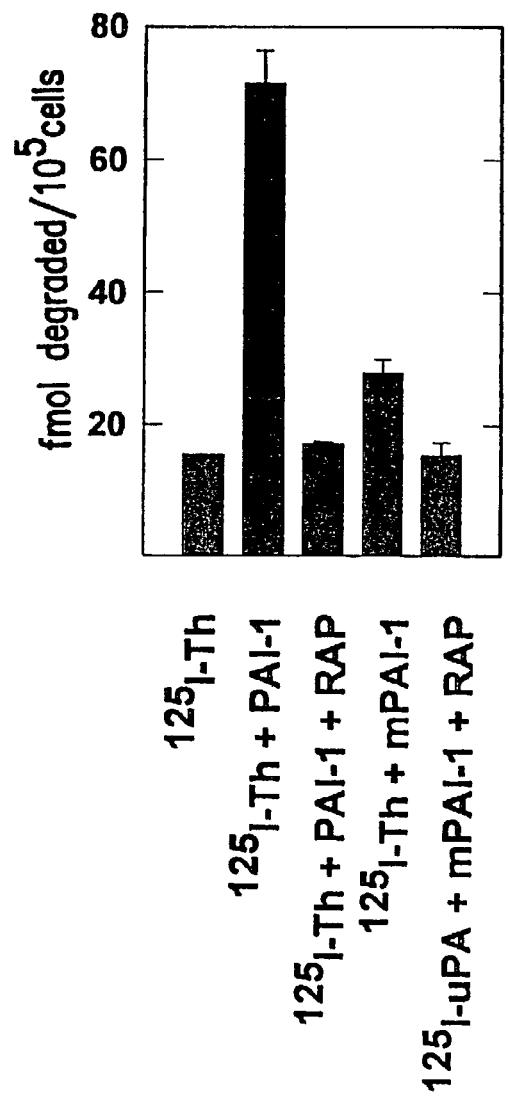
Figure 19:
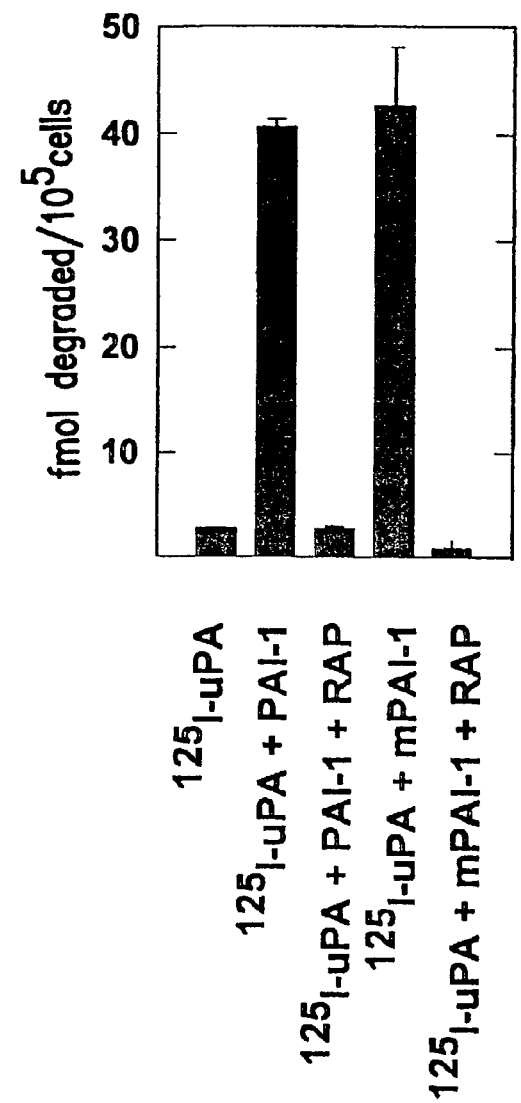

Because Vn had been shown to promote the inhibition of thrombin by PAI-1, studies were done to determine whether such a mechanism was involved in the pre-type II pneumocyte clearance of thrombin. Pre-type II pneumocyte layers grown in serum-containing medium were incubated with either wild-type PAI-1 or a mutant PAI-1 which is unable to bind Vn but is identical to wild-type PAI-1 in its ability to bind heparin or to inhibit uPA (Lawrence, D. A. et al., (1994) *J. Biol Chem.* 269, 15223-15228). As shown in FIGS. 16 and 18, inclusion of wild-type PAI-1 promoted greater endocytosis and degradation of $^{125}$I-thrombin compared to mutant PAI-1. In contrast, the endocytosis of $^{125}$I-uPA was enhanced to the same degree by either wild-type or mutant PAI-1 (FIGS. 17 and 19). RAP treatment blocked the wild-type PAI-1-promoted endocytosis of both thrombin and uPA. The results indicated that PAI-1 binding to Vn derived from serum is important for the clearance of thrombin. The present inventors believe that the clearance of free thrombin requires complex formation with PAI-1, a process known to be greatly accelerated by Vn. The low level of thrombin clearance promoted by mutant PAI-1 was likely due its ability to form a complex with thrombin, albeit inefficiently, in the absence of Vn. Given that heparin also stimulates complex formation although less efficiently than Vn (Gebbink, R. K. et al., (1993) *Biochemistry* 32, 1675-1680), proteoglycans present in the cell culture may act to accelerate complex formation in lieu of Vn. Since PAI-1 binds uPA with high affinity without a requirement for Vn, uPA clearance (FIGS. 17 and 19) was not expected to depend on the ability of PAI-1 to complex with Vn.

Figure 20:
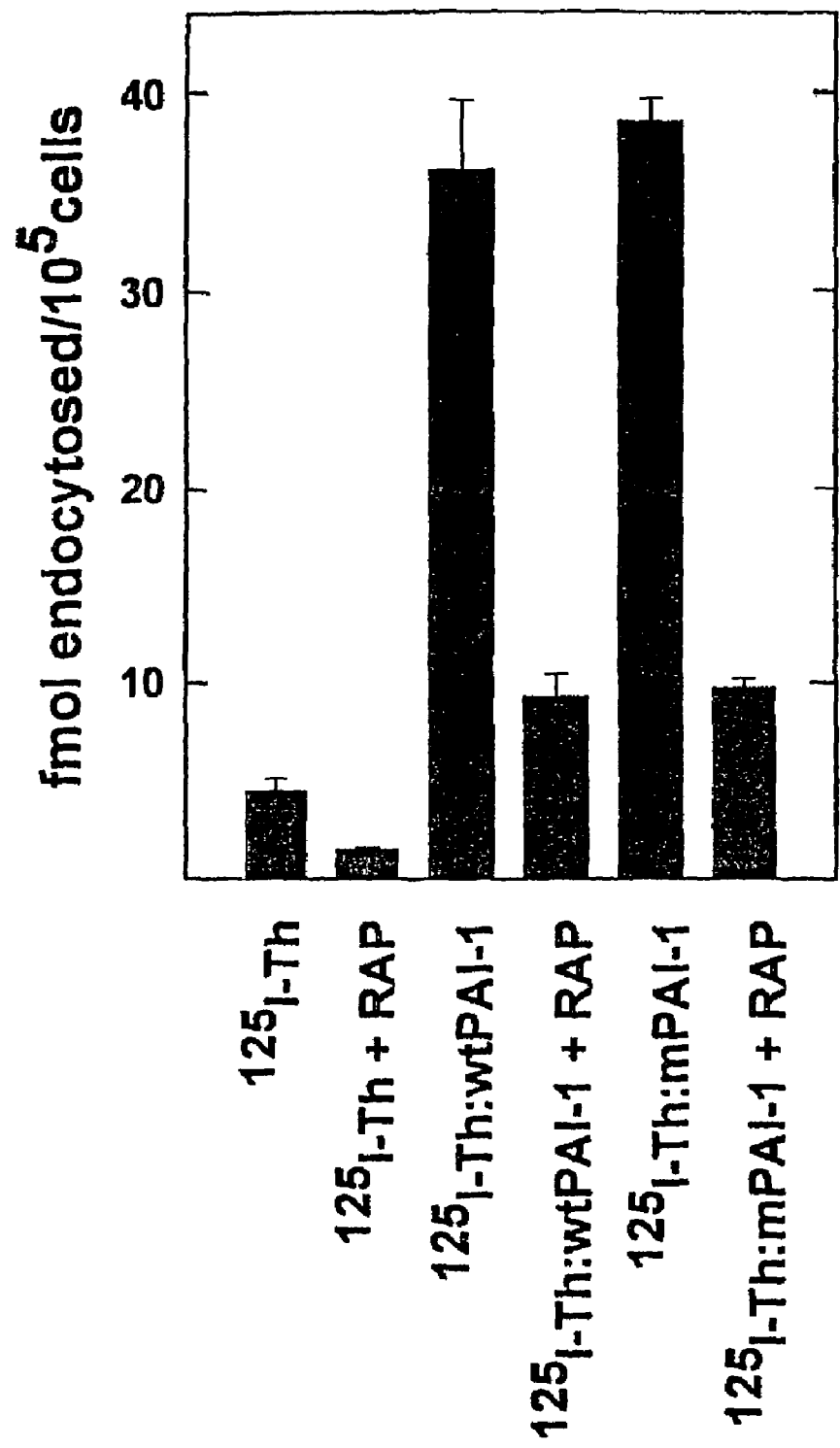
FIGS. 20 and 21 are a set of graphs showing endocytosis and degradation of $^{125}$I-thrombin that has been pre-complexed to either wild-type PAI-1 (FIG. 20) or mutant PAI-1 (FIG. 21). Pre-type II pneumocyte cells were incubated with $^{125}$I-Th:wtPAI-1 or $^{125}$I-Th:mPAI-1 (1 nnM complex). See FIGS. 16-19 for designation of groups. Where indicated, RAP (1 µM) was added along with the complex. Endocytosis and degradation of each type of $^{125}$I-complexes are shown. The results represent 2 experiments. Each plotted value represents the average of duplicate determinations with the range indicated by bars.
Figure 21:
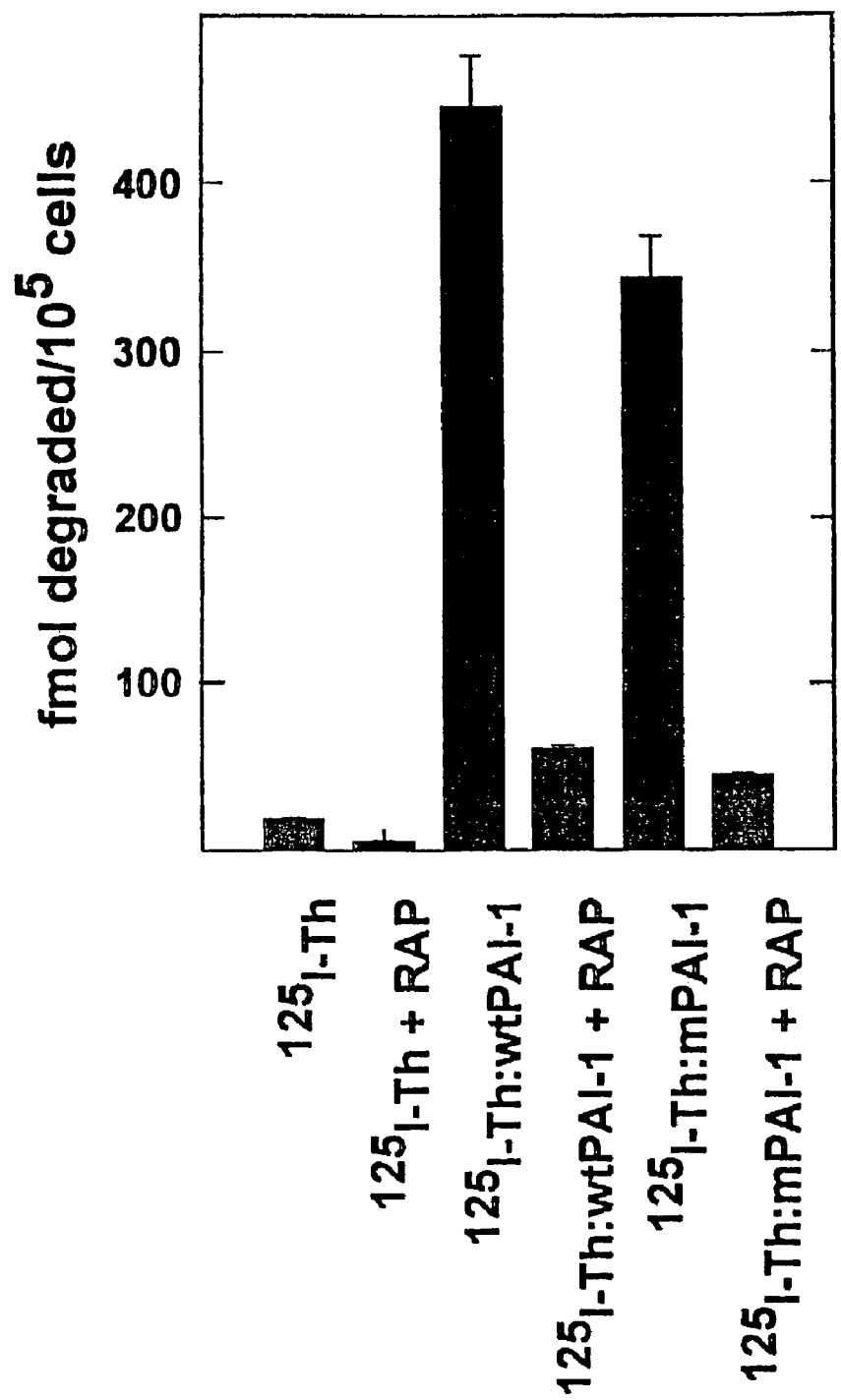

To show that the PAI-1 mutation did not effect the ability of its complex with thrombin to bind to LRPs, complexes of $^{125}$I-thrombin with either wild-type PAI-1 or mutant PAI-1 were formed in vitro. As shown in FIGS. 20-21, both types of complexes were readily endocytosed (FIG. 20) and degraded (FIG. 21) by the pre-type II pneumocytes. Both endocytosis and degradation were inhibited by RAP.

These results indicate that complexes of thrombin and either wild-type or mutant PAI-1 are recognized equally by LRP receptors. Therefore, when free $^{125}$I-thrombin was presented to cells as in FIGS. 16-19, the complex formation with PAI-1:Vn was required for efficient complex formation between thrombin and PAI-1 which led to rapid LRP-mediated endocytosis and degradation.

Figure 22:
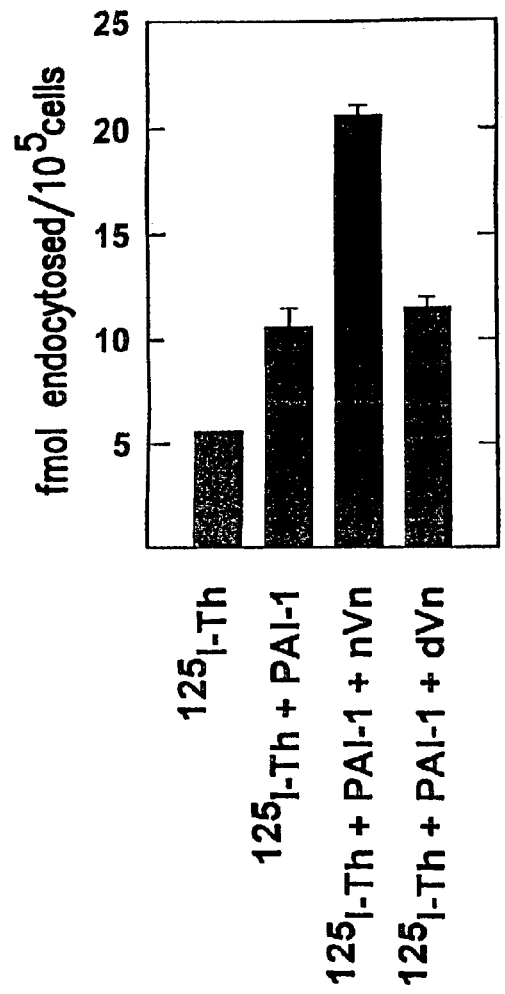
FIGS. 22-25 are a set of graphs showing the effect of native or conformationally-altered Vn on the endocytosis and degradation of $^{125}$I-thrombin (FIGS. 22 and 24) or $^{125}$I-uPA (FIGS. 23 and 25) in the presence of wtPAI-1. Pre-type II pneumocytes were incubated with either native Vn ("nVn", 50 nM) or conformationally-altered Vn (denatured="dVn", 50 nM). After washing the cells were incubated with wild-type PAI-1 (10 nM) followed by addition of either $^{125}$I-thrombin (10 nM) or $^{125}$I-uPA (10 nM).
Figure 23:
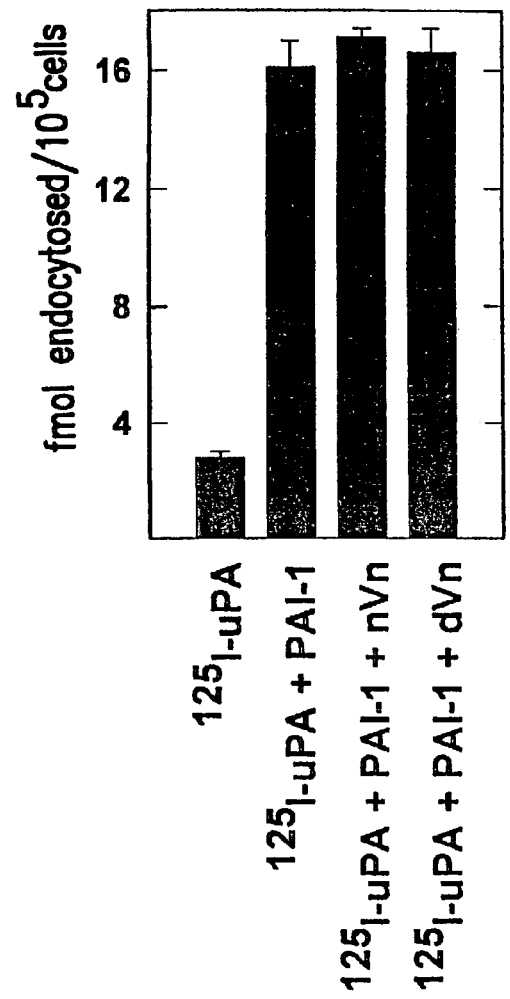
Figure 24:
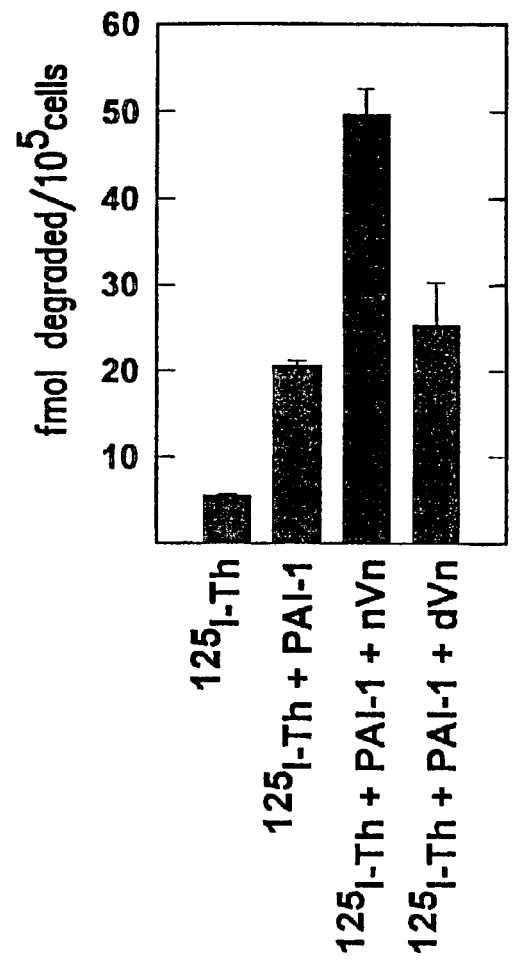
Figure 25:
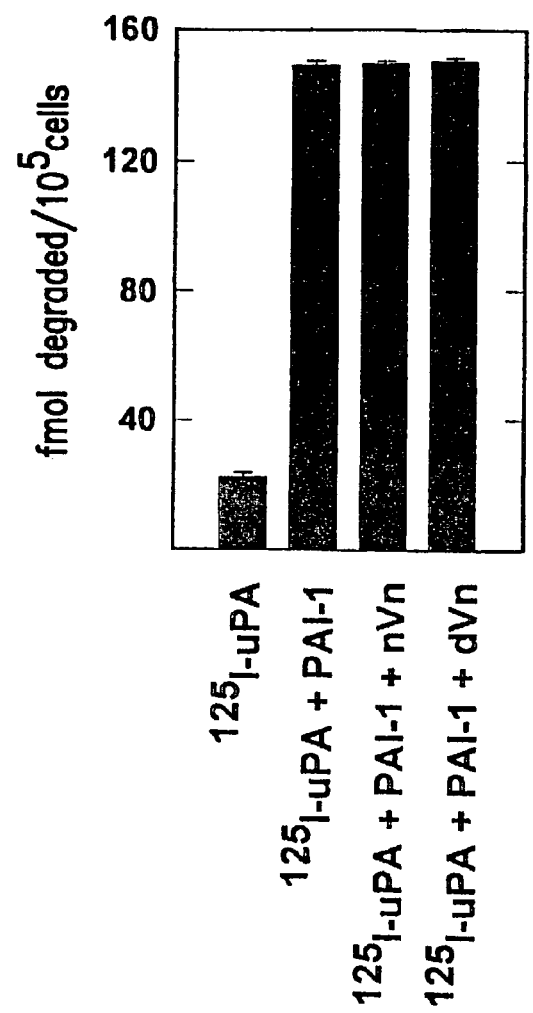

PAI-1-promoted Endocytosis and Degradation of Thrombin is Augmented by Native But Not Conformationally-altered Vn It is known that native Vn accelerates the formation of the thrombin:PAI-1complex whereas conformationally altered Vn does not (Naski et al., supra). To determine whether the conformational state of Vn influenced PAI-1-mediated cellular clearance of thrombin, studies examined the clearance of $^{125}$I-thrombin in the presence of PAI-1 and either native or conformationally altered Vn. As shown in FIGS. 22 and 24) (using cells grown in the absence of serum to eliminate exposure to serum Vn), exogenous native Vn enhanced $^{125}$I-thrombin clearance. Conformationally altered Vn was no more effective in promoting the clearance of $^{125}$I-thrombin than was PAI-1 alone. Giventhat glycosaminoglycans have been shown to promote inhibition of thrombin by PAI-1, proteoglycans may have contributed the low level of thrombin clearance observed with PAI-1 alone or PAI-1 plus conformationally altered Vn. By comparison, $^{125}$I-uPA clearance mediated by complexing with PAI-1 was not influenced by native or conformationally altered Vn (FIGS. 23 and 25).

III. Discussion

Based on these findings, it was concluded that active thrombin clearance by pre-type II pneumocytes is mediated through complex formation with PAI-1 and the subsequent interaction of the complex with either LRP-1 or LRP-2. The role of native Vn in this process is critical, presumably due to the fact that it augments the formation of the thrombin:PAI-1 complex which is otherwise inefficient.

Vn binds both PAI-1 and thrombin. These binding interactions apparently lead to more efficient interaction between PAI-1 and thrombin. It is not known whether Vn remains associated with PAI-1 and thrombin following their interaction. Vn forms a ternary complex with thrombin bound to either ATIII, HCII, proteinase nexin I or $\alpha_1$AT-Pittsburgh (III, C. R. et al. (1985) *J. Biol. Chem.* 260, 15610-15615; Rovelli, G. et al., (1990) *Eur. J. Biochem.* 192, 797-803; Tomasini, B. R. et al. (1989) *Biochemistry* 28, 7617-7623). However, the PAI-1: Vn complex dissociates following the interaction with either uPA or tPA. The above experiments did not evaluate whether Vn was endocytosed along with thrombin:PAI-1 complex. Other studies showed that active thrombin but not inactivated thrombin promoted the cellular clearance of $^{125}$I-native Vn. (Panetti, T. S. et al. (1993) *J. Biol. Chem.* 268, 11988-11993). Since inactive thrombin does not bind serpins whereas active thrombin can, the authors speculated that an interaction between thrombin and some endogenous inhibitor facilitated native Vn clearance. This is consistent with the present findings of (a) active thrombin being cleared more efficiently than inactivated thrombin and (b) PAI-1 antibodies inhibiting the clearance of active thrombin. The results indicate the possibility that a ternary complex of thrombin:PAI-1 and Vn may be cleared. The fact that RAP blocks thrombin clearance to the same extent as excess unlabeled thrombin indicates that LRP receptors are primarily responsible for mediating the clearance process A major concept to emerge from this study is that PAI-1 mediates thrombin catabolism but it raises the question of when and where this might occur in vivo. While PAI-1 inhibits uPA and tPA with a second-order rate constants of $10^7$ $M^{-1}$ $sec^{-1}$, the second-order rate constant for inhibition of thrombin is about 10,000-fold less. The physiological relevance of PAI-1 inhibition of thrombin may not be immediately obvious until one considers that cofactors such as heparin and Vn dramatically enhance the ability of PAI-1 to inhibit thrombin. For example, in the presence of Vn the second-order rate constant for the inhibition of thrombin by PAI-1 is increased by more than two orders of magnitude. This effect makes PAI-1:Vn a 10-20-fold better inhibitor of thrombin than ATIII (in the absence of heparin). However, in blood, where the concentration of ATIII is 10,000-fold higher than PAI-1, PAI-1as not likely to be an important inhibitor of circulating thrombin. In extravascular sites such as in the recesses of a fibrin-containing thrombus, the present inventors believe that PAI-1 may act as a physiological inhibitor of thrombin. Fibrin is thought to sequester thrombin, protecting it from circulating inhibitors until lysis of the clot by plasmin. The thrombin thereby released would be available to drive post-clotting events such as mitogenesis and chemotaxis of cells involved in clot remodeling and tissue repair. PAI-1, derived from (a) platelets or (b) synthesized by cells invading a clot or on the boundaries of the clot, and Vn derived from either platelets or blood, could inactivate thrombin and promote its clearance by LRP-expressing cells (e.g. smooth muscle cells, macrophages, fibroblasts). This could be the mechanism for the negative regulation of the post-clotting effects of thrombin.

EXAMPLE III

Interaction of Different Conformers of PAI-1 with Vitronectin (Vn)

The inventors examined the binding of 6 different conformational forms of PAI-1 to both native and urea-treated Vn. The results indicate that only the active form of PAI-1 binds to Vn with high affinity and suggest that the Vn-binding domain of PAI-1 is sensitive to the conformation of PAI-1 and thus its activity state. The findings suggest that the binding epitope on PAI-1 may have evolved such sensitivity to prevent the accumulation of inactive PAI-1 at sites of subcellular attachment.

Materials

Purified PAI-1 either, active (>95%) or latent (>95%) were obtained from Molecular Innovations (Royal Oak, Mich.). The PAI-1 mutant Q123K has been previously described, and was purified to homogeneity in either the active or latent conformation as described (Kounnas, M. Z., et al., (1992) *J. Biol. Chem.* 267:12420-12423). Purified Vn, both native (Naski, M. C. et al., (1993) supra) ("nVn") and urea-purified ("dVn") were obtained from Drs. D. Mosher and T. Podor, respectively, Recombinant high molecular weight uPA was obtained form Dr. J. Henkin of Abbott Laboratories, and tPA (Activase) was from Genentech. Porcine pancreatic elastase was from Elastin Products, and bovine β-trypsin and β-anhydrotrypsin were prepared as by conventional means. The eight residue synthetic peptide Ac-Thr-Val-Ala-Ser-Ser-Ser-Thr-Ala corresponding to the PAI-1 reactive center loop from $P_{14}$ to $P_7$, residues 333-340 of SEQ ID NO:3, was synthesized by the University of Michigan Biomedical Research Core Facilities.

Generation of Cleaved and Complexed Forms of PAI-1

PAI-1 cleaved at the P4 position of the reactive center loop (Lawrence, D. A., et al., (1994) *J. Biol. Chem.* 269: 27657-27662) was produced by treatment of 4.6 µM active PAI-1 with a ⅒ molar equivalent of elastase for 30 min. at 23° C. in Tris buffered saline, pH 7.5 (TBS) followed by treatment of the sample with 1 mM (final concentration) of PMSF to inactive the elastase. PAI-1 complexes with uPA and tPA were formed by incubation of 1.5 molar equivalents of either enzyme with 4.6 µM active PAI-1 for 30 min. at 23° C. in TBS, followed by inactivation of residual enzyme by 1 mM (final concentration) of APMSF. Following incubation with either PMSF or APMSF all samples had no detectable enzymatic activity, and SDS-PAGE analysis indicated only trace amounts of unreacted PAI-1 in each sample. This residual unreacted PAI-1 is believed to represent the small amount of latent PAI-1 contained in the active PAI-1 preparation. Complexes with bovine β-trypsin were formed by reacting 26 µM active PAI-1 with 13 µM trypsin in 25 mM sodium phosphate, 125 mM NaCl, 0 5 mM EDTA, 10 mM CaCl$_2$, pH 6.6 for 30 min. at 23° C., after which the remaining active PAI-1 was removed by chromatography on uPA-agarose. SDS-PAGE analysis indicated that the complexes contained no detectable uncleaved PAI-1 and about 20% free cleaved PAI-1. The PAI-1-peptide complex was produced by incubating 6.4μM active PAI-1 with 200 μM peptide in 0.1M HEPES, 0.1 M NaCl, 1% PEG-8000, 0.1% Tween-80, pH 7.4 at 25° C. until no detectable PAI-1 inhibitory activity remained. The free peptide was then removed by chromatography on Heparin Sepharose. PAI-1-peptide complex formation was confirmed by thermodenaturation, mass spectra analysis, and by SDS-PAGE with and without tPA. The latter analysis indicated that the peptide annealed PAI-1 was a substrate for tPA and contained approximately 15% latent PAI-1, consistent with previous studies.

Assay for Various PAI-1 Conformational Forms Binding to Vn

PAI-1 binding to immobilized Vn was determined as previously described ((Lawrence, D A, et al. (1994) *J. Biol. Chem.* 269, 15223-15228)). Briefly, Vn at 1 μg/ml in phosphate buffered saline (PBS), was coated overnight onto Immulon 2 (Dynatech) rmicrotiter plates in a volume of 100 μl at 4° C., and all subsequent steps were performed at room temperature. The plates were washed with PBS followed by dH$_2$O, allowed to air dry for 15 min., and then blocked with 200 μl of 3% bovine serum albumin in PBS for 30 minutes. Next, PAI-1 containing samples were added, in a final volume of 100 μl, and incubation continued for one hour. Bound PAI-1 was then detected with affinity purified, biotinylated, rabbit anti-PAI-1 antibodies (Sherman, P. M., et al. (1992) *J. Biol. Chem.* 267:7588-7595) and streptavidin conjugated to alkaline phosphatase using the substrate p-nitrophenyl phosphate, disodium (Sigma) at a concentration of 4 mg/ml in 100 mM Tris-HCl pH.9.5, 5 mM MgCl$_2$. For analysis of the PAI-1-anhydrotrypsin complex binding to Vn, 1 μM (final concentration) of anhydrotrypsin was included in all wells during the PAI-1 incubation step. This concentration of anhydrotrypsin was 20-fold higher than the highest concentration of PAI-1 tested, and ten-fold higher that the reported K$_d$ for the interaction of PAI-1 and anhydrotrypsin.

RESULTS

Figure 26:
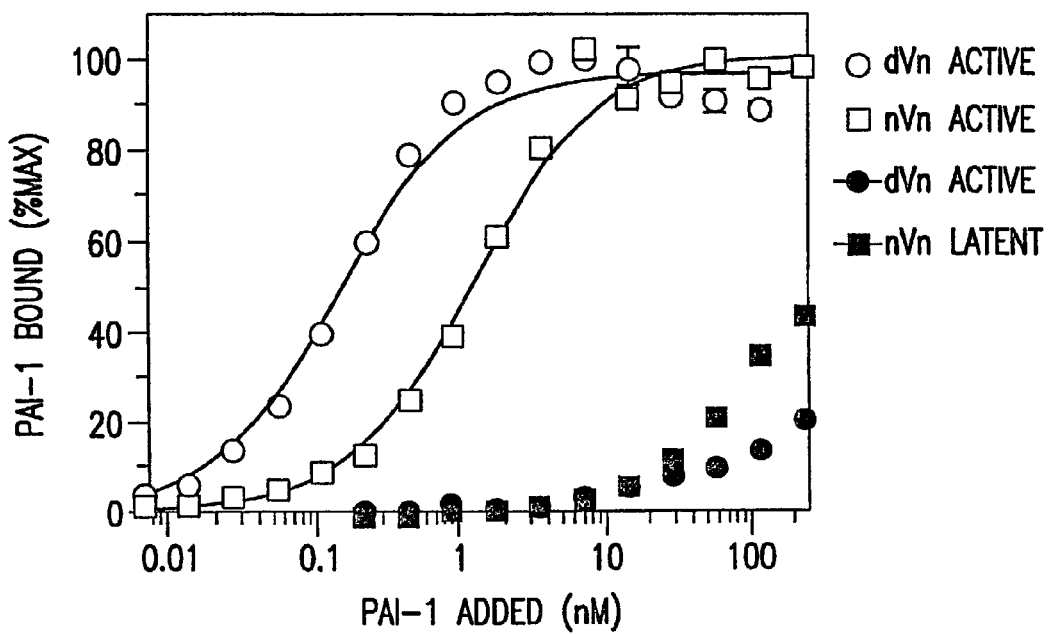
FIG. 26 is a graph showing binding of recombinant active or latent wtPAI-1 to microtiter plates coated with purified native (nVn) or urea-denatured(dVn) Vn. Bound PAI-1 was detected with affinity purified, biotinylated, rabbit anti-PAI-1 antibodies and streptavidin conjugated to alkaline phosphatase Data points represent the average of at least four separate determinations for each sample ±S.E.M.
Figure 27:
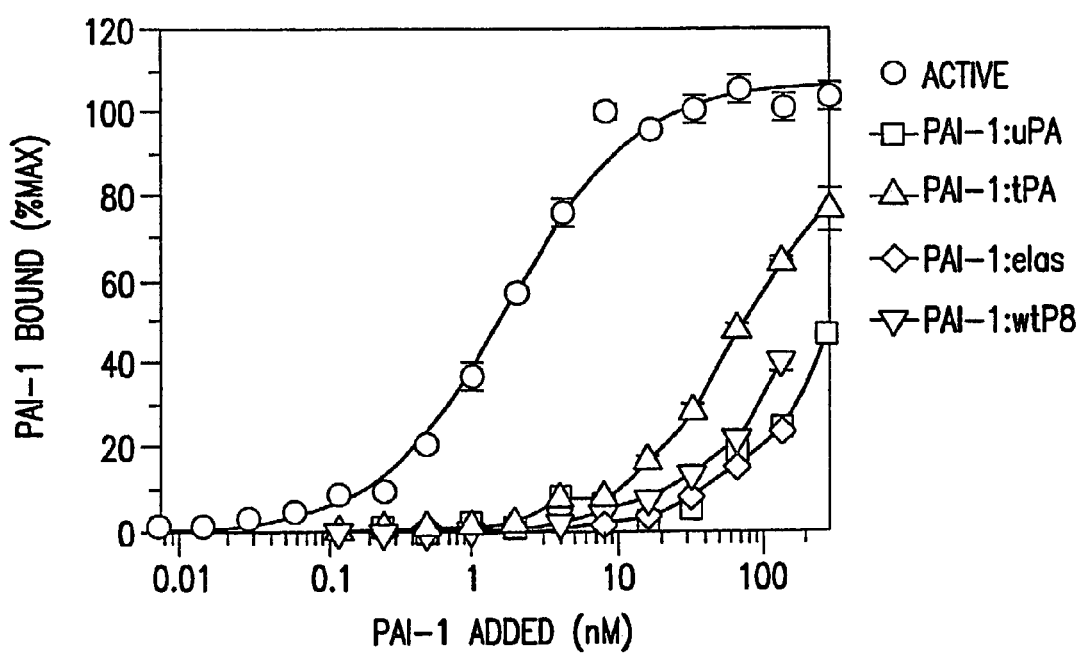
FIG. 27 is a graph showing the binding of four additional forms of PAI-1 to nVn coated microtiter plates. These forms include PAI-1 in a stable complex with either uPA or tPA, cleaved PAI-1 that is uncomplexed but has a reconstituted β-sheet A, and PAI-1 annealed to a synthetic RCL peptide, which has an intact RCL that is not inserted into β-sheet A, but has a reconstituted sheet A due to insertion of the synthetic peptide to form strand 4 of sheet A (Kvassman, J., et al., (1995) *J Biol. Chem.* 270, 27942-27947). The assay was performed as in FIG. 26 with the same number of determinations.

FIG. 26 demonstrates that pure active PAI-1 binds to both forms of Vn with high affinity. However, the K$_d$ for dVn is nearly 10-fold lower than for nVn (150 μM compared to 1.4 nM). In contrast pure latent PAI-1 binds to both forms of Vn with much lower affinity (K$_d$>225 nM). These results support the contention that only active PAI-1 binds to Vn with high affinity and contradict the suggestion that both forms of PAI-1 bind to Vn with equal affinity. The relative K$_d$'s calculated form the data in FIG. 14 are also consistent with previously reported values. Thus, the reported K$_d$ of 50-190 nM is much closer to the present estimate. (The K$_d$ values must be estimates since the binding did not saturate at the concentrations tested.] For latent PAI-1 binding to either native Vn or dVn, the K$_d$>225 mM (FIG. 26).

The observation that latent PAI-1 binds to Vn with a much lower affinity than active PAI-1 suggests that the conformational change associated with conversion to the latent form may be responsible for the reduced affinity. The present inventors and their colleagues (Lawrence et al., 1994, supra) had suggested that stabilization of PAI-1 by Vn binding occurs when Vn binding to strand 1 of β-sheet A limits the mobility of β-sheet A necessary for insertion of the PAI-1 RCL during transformation to the latent conformation. This model is consistent with the observation that reconstitution of the serpin β-sheet A from a five stranded primarily parallel β-sheet into a six stranded antiparallel β-sheet by insertion of the RCL into β-sheet A as strand 4, requires extensive rearrangement of β-strands 1, 2 and 3 of sheet A (Stein, P. et al, (1991) *Mol. Biol* 221.615-621). Restriction of this rearrangement by Vn could retard loop insertion and thus the conversion of PAI-1 to the latent form. The inventors predicted that rearrangement of sheet A would also modify the Vn binding epitope on PAI-1. This proposal was supported by the results shown in FIG. 14 indicating that latent PAI-1, which has a reorganized β-sheet A, binds both forms of Vn with a markedly reduced affinity compared to active PAI-1.

The present inventors and colleagues investigated the binding of four additional forms of PAI-1 to both native and dVn, and like latent PAI-1, each of these conformers is thought to have its β-sheet A in the six stranded form. They include:

(1) PAI-1 in a stable complex with either uPA or tPA, which was previously shown to be cleaved at the P$_1$ position of the RCL and to have the RCL inserted into β-sheet A;

(2) Cleaved PAI-1 that is uncomplexed but has a reconstituted β-sheet A; and (3) PAI-1 annealed to a synthetic RCL peptide, which has an intact RCL that is not inserted into β-sheet A, but has a reconstituted sheet A due to insertion of the synthetic peptide to form strand 4 of sheet A (Kvassman, J. et al, (1995) *J. Biol. Chem.* 270:27942-27947).

The results are shown in FIG. 15, and demonstrate that, like latent PAI-1, none of the other PAI-1 conformers bound to nVn with high affinity (estimated relative K$_d$s>100 nM). Similar results were obtained with dVn.

The relatively low affinity observed for both the tPA-PAI-1 and UPA-PAI-1 complexes with both forms of Vn is consistent with previous reports that tPA can dissociate PAI-1 from soluble Vn (Declerck et al. ,1988, supra), and that PAI-1 can be removed from ECM by treatment with uPA (Mimuro et al., 1987, sypra). Interestingly, PAI-1 in complex with the synthetic RCL peptide shows the same reduced affinity for Vn as the other conformers. This indicates that cleavage of the RCL is not required for the loss of binding affinity, but that it is the reorganization of β-sheet A that is necessary, since in the PAI-1-peptide complex the natural RCL remains intact (Kvassman, 1995, supra). Taken together, the results suggest that the Vn-binding epitope of PAI-1, which includes strand 1 of β-sheet A, is sensitive to conformational changes in β-sheet A.

Figure 28:
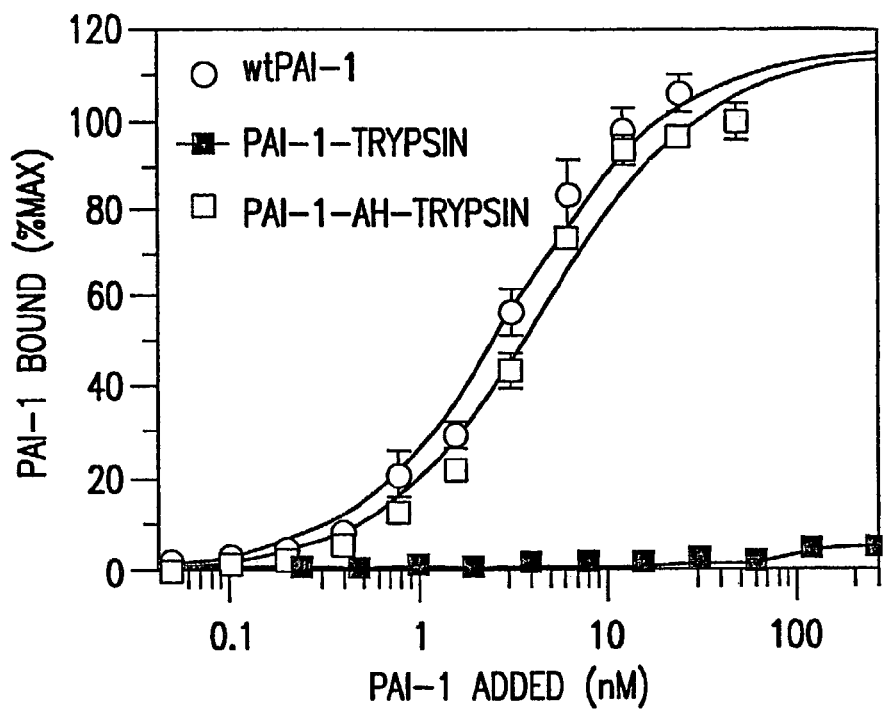
FIG. 28 is a graph showing binding of active wtPAI-1, covalent complexes of wtPAI-1-trypsin, or non-covalent PAI-1-anhydrotrypsin complexes to nVn coated microtiter plates. The assay was performed as in FIG. 26, except that for analysis of the PAI-1-anhydrotrypsin complex binding to Vn, 1 µM (final concentration) of anhydrotrypsin was included in all wells during the PAI-1 incubation step. Data points are as in FIG. 26.

To confirm that it is the rearrangement of sheet A that is responsible for the loss of affinity and not simply the association of PAI-1 with an enzyme, the relative binding affinity of PAI-1 in complex with either trypsin or anhydrotrypsin was tested. PAI-1 is an efficient inhibitor of trypsin and forms SDS-stable, RCL inserted complexes just as with uPA or tPA. In contrast, anhydrotrypsin binds to the PAI-1 RCL in a non-covalent association that does not result in cleavage of the RCL or its insertion into β-sheet A. These results are shown in FIG. 28 and indicate that like uPA and tPA, PAI-1-trypsin complexes have a very low affinity for Vn. However, PAI-1 in association with anhydrotrypsin binds to Vn with essentially the same affinity as active PAI-1 alone. This indicates that it is not the binding of an enzyme to the RCL that results in loss of Vn affinity but that it is cleavage of the RCL and subsequent insertion of the loop into β-sheet A. The results strongly suggest that the reorganization of β-sheet A leads to the reduction in PAI-1's affinity for Vn.

Figure 29:
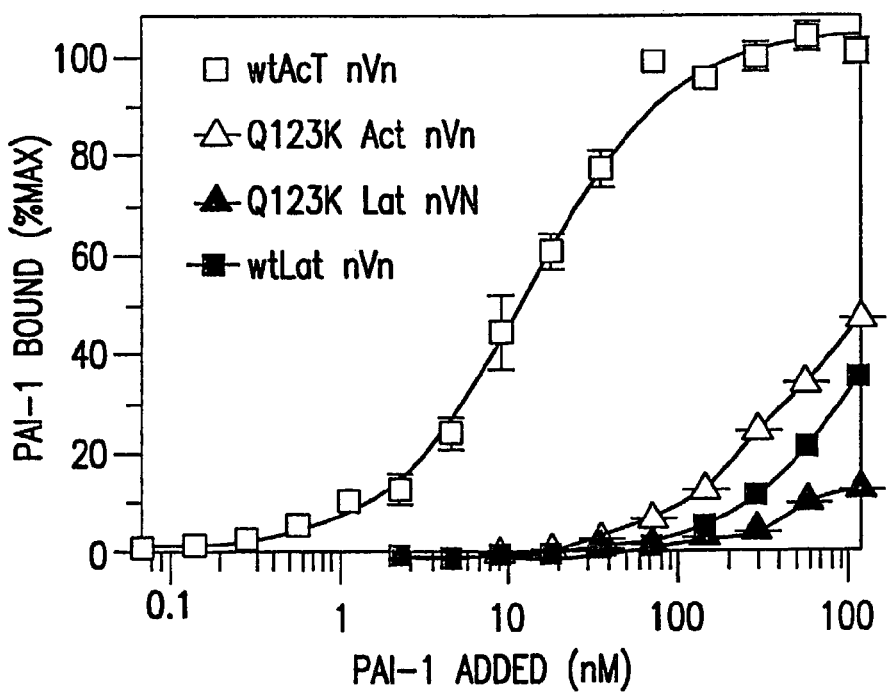
FIG. 29 is a graph showing binding of recombinant active or latent wtPAI-1 and active or latent mutant PAI-1 Q123K to nVn coated microtiter plates. Assay and data points are as in FIG. 26.

Presently, there has been only one region on PAI-1 that has been shown to interact with Vn (Lawrence et al. 1994, supra; Van Meijer et al. (1 994) *FEBS Lett.* 352:342-346; Padmanabhan, J. et al. (1995) *Thromb. Haemost* 73:829-834), and our data suggest that this site loses affinity for Vn following rearrangement of β-sheet A. However, PAI-1 may have two independent binding sites for Vn, one with high affinity that is only expressed on active PAI-1 and one with low affinity that is present on all conformations. While it is impossible to completely distinguish between these two possibilities, if the latter were true, then mutations that affect one site would not necessarily affect the other site. Conversely, if the different forms of PAI-1 interact with Vn through the same, though conformationally altered, site then a single point mutation in PAI-1 could affect binding in both high and low affinity interactions. Accordingly, the PAI-1 point mutation Q123K that has a greatly reduced affinity for Vn was purified and the active and latent forms separated and examined for Vn binding (FIG. 29). Comparison of the binding of active and latent Q123K PAI-1 to nVn with the binding of active and latent wtPAI-1 indicated that both the active and latent forms of the mutant bind to nVn with lower affinity relative to their wtPAI-1 counterpart. Similar results were obtained when dVn was used. This suggested that both the high and low affinity interactions utilize the same or at least overlapping binding epitope(s) on PAI-1 since they are affected to a similar extent by the Q123K mutation. This mutation has no affect on the inhibitory activity of PAI-1 or on its affinity for heparin-Sepharose, indicating that the affects of the mutation are local, and do not introduce significant global changes in the PAI-1 structure. Comparing the surface accessibility of Q123 on a model of active PAI-1 to its accessibility in the latent structure indicate that in latent PAI-1 Q123 becomes partially obscured by surrounding residues compared to its exposure in the active form. This is consistent with the loss of affinity for Vn observed with latent PAI-1, and support the notion that PAI-1 contains only one binding epitope for Vn which is conformationally sensitive.

Recent studies of the serpin mechanism of inhibition indicate that it follows a multi-step process that requires an exposed RCL (Shore et al. 1994, supra; Lawrence et al., 1995, supra; Fa, M. et al, (1995) *Biochem.* 34:13833-13840; Wilczynska, M. et al, (1995) *J. Biol. Chem.* 270:29652-29655). Upon association with a target proteinase the serpin RCL is cleaved at its P1-P1' bond and this is followed by a rapid insertion of the RCL into β-sheet A yielding the stable serpin-proteinase complex. In the present study we demonstrate that the PAI-1 Vn binding epitope on the edge of β-sheet A is sensitive to this conformational change in β-sheet A, as well as to similar changes associated with conversion of PAI-1 to the latent form or cleavage in the RCL by a non-target proteinase. This sensitivity may provide a way to ensure the expression of PAI-1 activity at specific sites of action. For example, it is thought that Vn serves to localize PAI-1 to the ECM where it regulates local proteolytic activity (Mimuro et al., 1987, supra). In this situation it may be beneficial to permit only functionally active PAI-1 to bind to Vn. On a cell surface, an inactive ligand can be internalized and degraded. However, this type of regulation may not be as efficient on the less dynamic ECM. Therefore, to prevent Vn from becoming saturated with inactive forms of the inhibitor, a system may have evolved that is sensitive to the conformation of PAI-1 which is closely linked to its activity state.

EXAMPLE IV

PAI-1 Prevents Integrin Vitronectin Receptor ($\alpha_v\beta_3$)-Mediated Cell Migration by Blocking the RGD Cell Attachment Site on Vitronectin The PAI-1 binding site on Vn was recently localized to the first 50 amino acid residues. This region also contains the RGD (Arg-Gly-Asp) cell attachment site. To determine whether these binding sites overlap, competition studies between purified VnR and PAI-1 were performed. The competition of active wtPAI-1 was compared to two different PAI-1 mutants. One, Q123K-PAI-1 has a single amino acid substitution, that does not affect inhibitory activity, but reduces its affinity for Vn approximately 2 orders of magnitude. The second, P1 Ala-PAI-1 also has a single substitution (R346A) that destroys its ability to inhibit PAs, but has no affect on Vn binding.

Materials and Methods

Active forms of wtPAI-1 and the PAI mutants were prepared as described (Kvassman, J. et al., *Fibrinolysis* 9:120-125 (1995)). Native Vn (Molecular Innovations) was coated to microtiter wells (1µg/ml) for 2 hours at 37° C., followed by blocking with 2% BSA in 50 mM Tris, pH 7.5 containing 10 nmM NaCl and 5 mM $CaCl_2$ (Binding buffer). Vitronectin receptor (VnR) ($\alpha_v\beta_3$ integrin) was purified from human placenta as described (Smith, J. W. et al., *J. Biol. Chem.* 265:11008-11013 (1990)). Radiolabeled VnR (2.5 nM) was allowed to bind to microtiter wells in the presence of increasing concentrations of either wild-type PAI-1, Q123K-PAI-1 or P1Ala-PAI-1. The samples were processed as described (Stefansson, et al., 1995, supra). The results (shown in FIG. 30) were plotted using the program "Grafit" and represents three experiments performed in duplicate.

Figure 30:
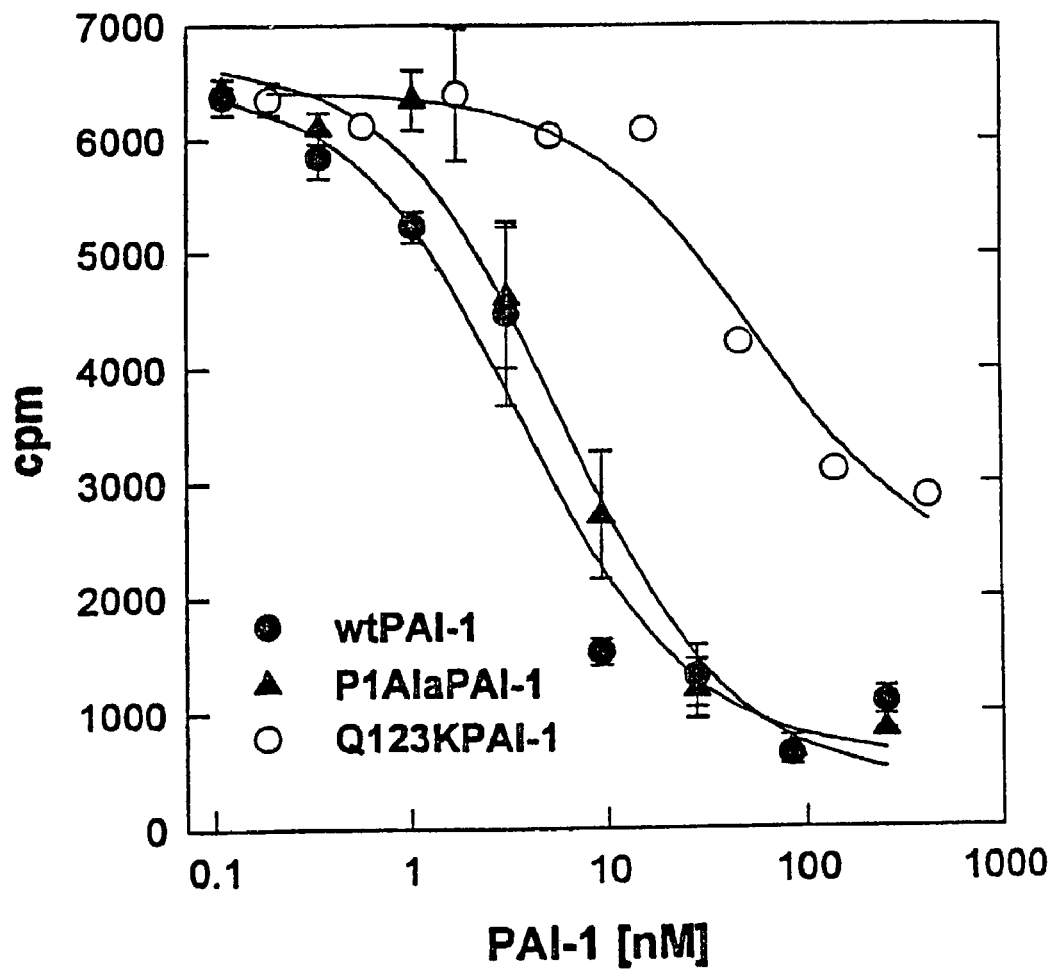
FIG. 30 is a graph showing the binding of radiolabeled VnR to Vn and its competition by wtPAI-1 and PAI-1 mutants. The results represents three experiments performed in duplicate.
Figure 31:
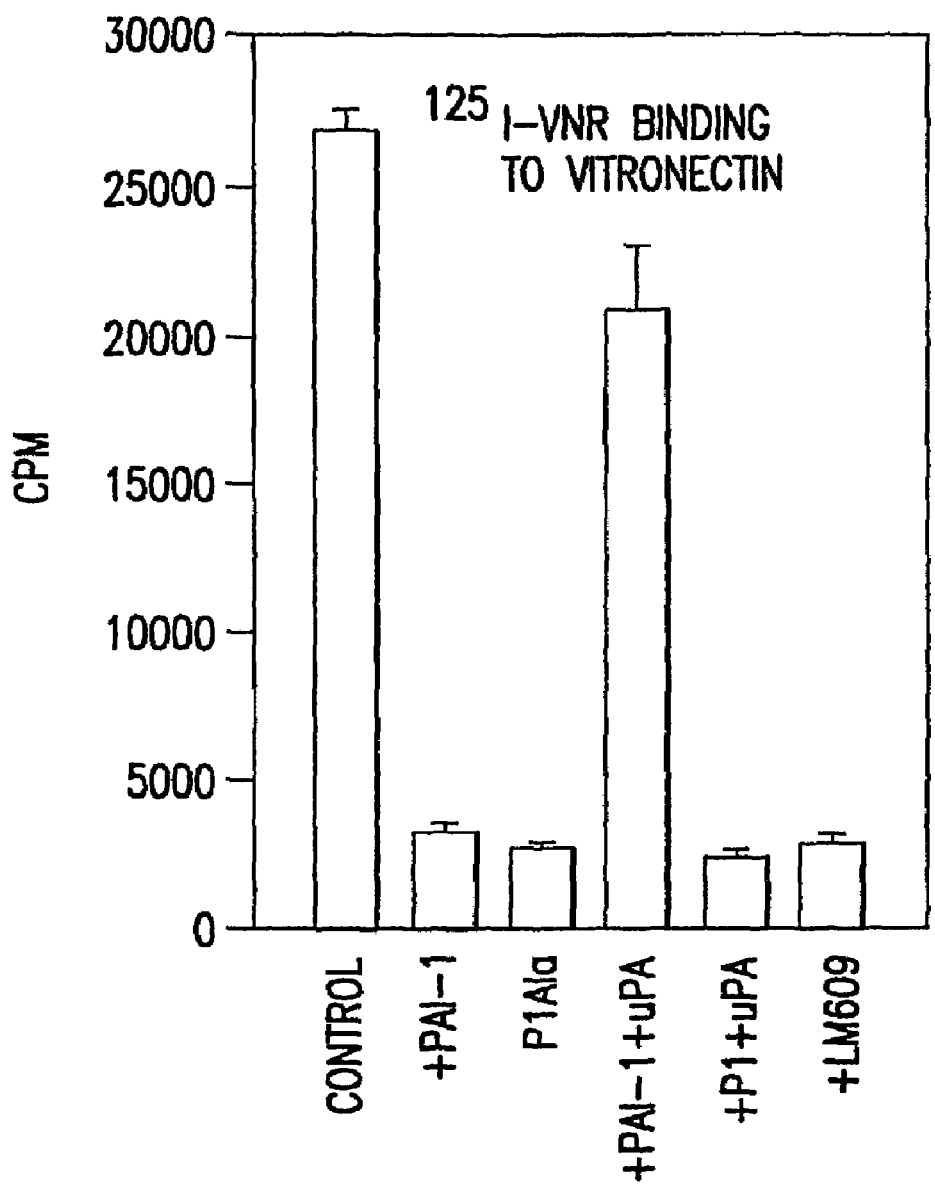
FIGS. 31 and 32 are a set of graphs showing the inhibition by PAI-1 and the P1 Ala mutant of the binding of VnR to Vn (FIG. 31) or fibronectin (FIG. 32) and its reversal by uPA. The results represent 2 experiments, each performed in duplicate.
Figure 32:
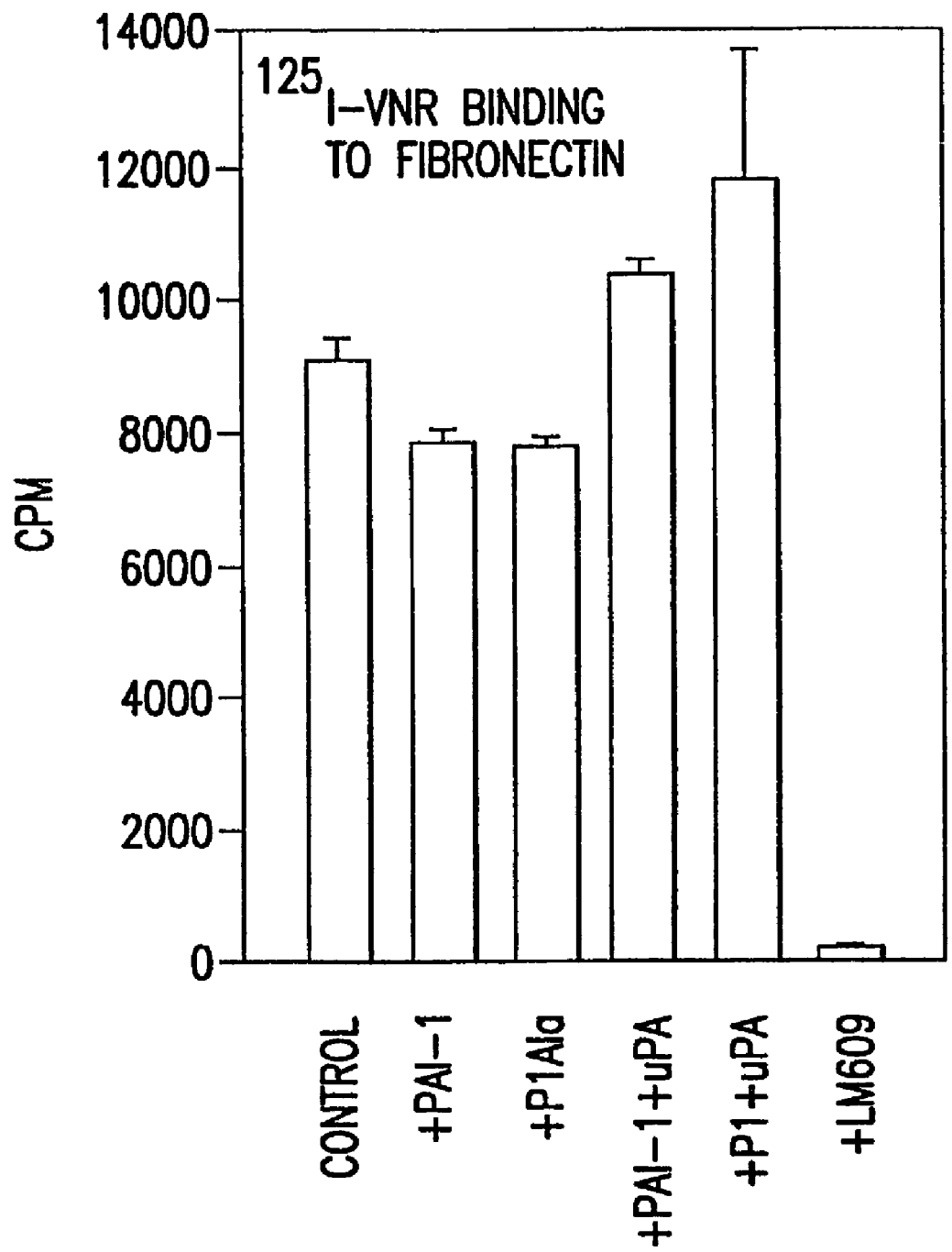

In the experiment shown in FIGS. 31 and 32, $^{125}$I-VnR (5 nM) was allowed to bind to native Vn (FIG. 31) or fibronectin (FIG. 32) coated on microtiter plates in the presence of wtPAI-1 (500 nM), and P1-Ala-PAI-1 (500 nM), unbound PAI-1 was removed and uPA (400 nM) was added where indicated. A mAb specific for integrin $\alpha_v\beta_3$, LM609 (50 µg/ml), was incubated similarly as a positive control for inhibition of binding. Samples were incubated and developed as described above (for FIG. 30). The results represents 2 experiments, each performed in duplicate.

Figure 33:
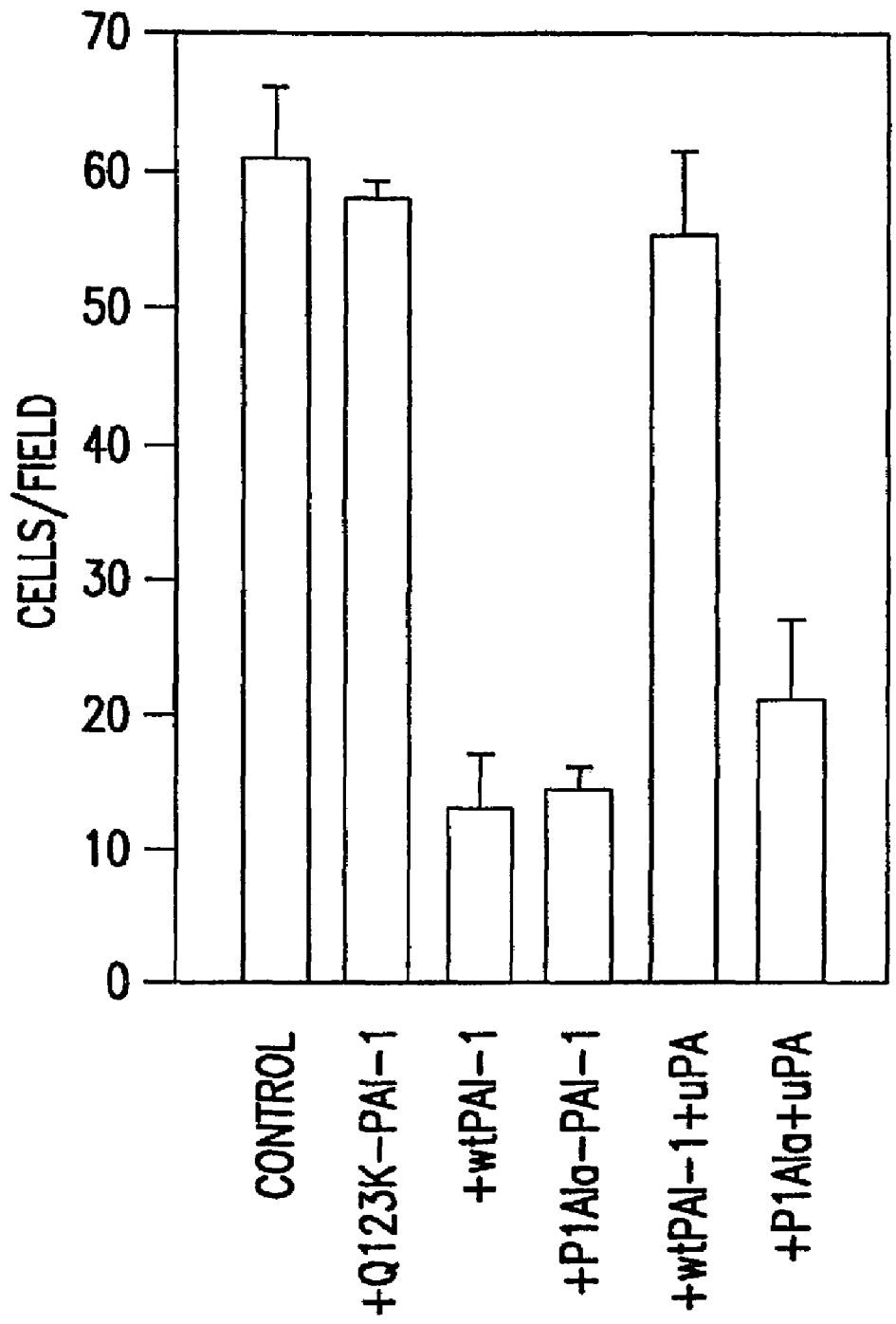
FIGS. 33 and 34 are a set of graphs showing the inhibition by PAI-1 and mutants thereof of smooth muscle cell adhesion to Vn (FIG. 33) and fibronectin (FIG. 34) and its reversal by uPA. The results represents 4 experiments performed in duplicate.
Figure 34:
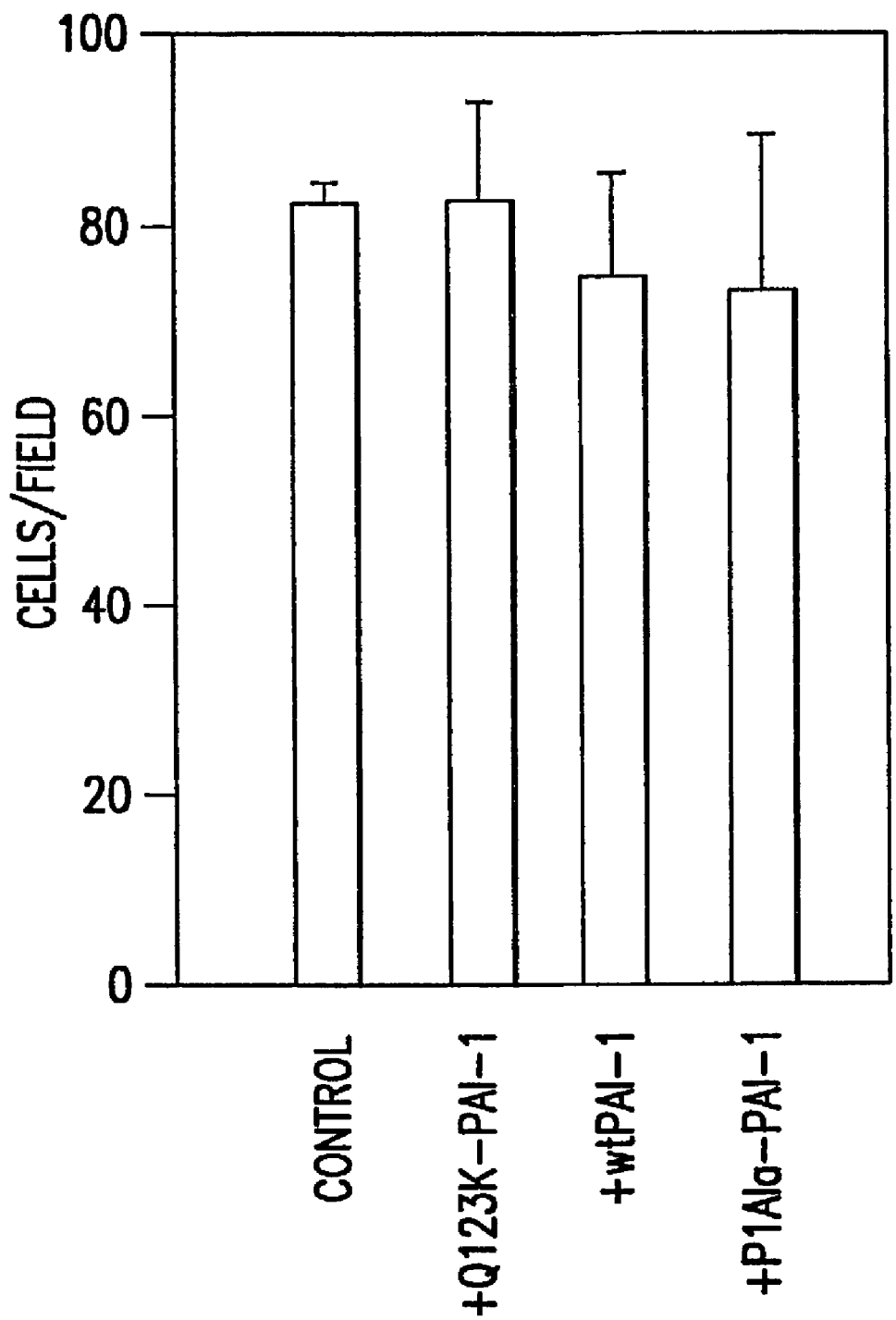

In the study depicted in FIGS. 33-34, rabbit SMC were detached using a non-enzymatic cell dissociation solution (Sigma). Cells were resuspended in serum-free medium containing either wtPAM-1, Q123K-PAI-1 or P1Ala-PAI-1 (75 nM final concentration) and allowed to attach for 30 min at 37° C. The plates were washed and stained using 2% crystal violet. Cells were counted on two random fields in duplicate wells. The results represent 4 experiments performed in duplicate.

In the next study, Transwells were coated with Vn and blocked as described above for FIG. 30. Rabbit SMC were detached using a mild trypsin treatment, washed in 0.5 mg/ml trypsin inhibitor and pelleted by centrifugation. Cells were allowed to attach and spread on the upper chamber in serum-free medium (0.5-1 hour) before PAI-1 (500 nM) was added. After 30 min incubation, serum was added, and the wells were incubated for 3-4 hours. Migrated cells were stained and counted.

Results

Both active wtPAI-1 and P1Ala-PAI-1 were found to be efficient competitors of the binding of purified $^{125}$I-VnR to native Vn ($K_i$ was about 4 nM, FIG. 30). In contrast, Q123K-PAI-1 was a poor competitor of VnR binding, yielding an estimated $K_i$ greater than 100 nM. Together, these results demonstrated that the high affinity of PAI-1 for Vn, and not the ability of PAI-1 to inhibit PAs, is responsible for the inhibition of VnR binding to Vn.

Neither the wt PAI-1 nor the two different PAI-1 mutants affected binding of $^{125}$I-VNR to fibronectin, indicating the specificity of the interaction for Vn.

PAI-1 undergoes profound conformational changes upon inhibition of a proteinase (Shore et al., 1995, supra), which leads to loss of its high affinity for Vn. Therefore, PAs might be expected to regulate the ability of PAI-1 to block the RGD site on Vn. To examine this possibility, competition assays were performed with and without uPA. uPA in 2-fold molar completely blocked the inhibition of $^{125}$I-VnR binding to Vn by wtPAI-1 (FIGS. 31-32). These findings are in accord with the observation that the PAI-1:uPA complex has significantly lower affinity for Vn than does the VnR, allowing the VnR to displace the PAI-1:uPA complex. As expected, P1 Ala-PAI-1 did not reduce the inhibition of VnR binding in the presence of uPA, consistent with the mutant's lack of reactivity with uPA.

A mAb specific for integrin $\alpha_v\beta_3$, LM609, inhibited the binding of $^{125}$I-VnR to Vn to the same extent as did PAI-1, indicating that (a) the VnR preparation contained primarily $\alpha_v\beta_3$ and (b) PAI-1 specifically blocked the binding of $\alpha_v\beta_3$ to Vn (FIGS. 31-32).

To test whether PAI-1 could similarly inhibit the interactions of cells with Vn, adhesion and migration assays were performed with vascular smooth muscle cells (SMC). Both active wtPAI-1 and P1 Ala-PAI-1 inhibited adhesion of SMC to Vn (FIGS. 33-34). In contrast, Q123K-PAI-1 did not inhibit adhesion, indicating that the binding of PAI-1 to Vn, and not the ability of PAI-1 to inhibit PAs, was responsible for blocking cell attachment. Furthermore, addition of uPA to wtPAI-1 bound to Vn prevented the inhibition of cell attachment whereas uPA had no affect on the inhibition of SMC attachment by P1 Ala-PAI-1.

Interestingly, whereas PAI-1 inhibited adhesion of SMC, the mAb to $\alpha_v\beta_3$ did not, indicating that SMC must have other integrins that play a role in attachment to Vn, and that PAI-1 blocks access to all of these adhesion molecules. Consistent with the results using purified VnR, PAI-1 had no effect of SMC adhesion to fibronectin.

Active wtPAI-1 and R346A-PAI-1 also inhibited SMC migration, as measured in Transwells coated with Vn. This inhibition was similar to that caused by LM609. The Q123K-PAI-1 mutant did not inhibit migration. As with cell attachment, inclusion of uPA reversed the inhibition by wtPAI-1 but not by P1Ala-PAI-1.

Wound conditions were simulated in vitro using a razor cut monolayer model. Migration and adhesive properties of type II pneumocytes on a Vn-coated surface were observed microscopically. The results indicated that the PAI-1 mutant with low affinity for Vn had no effect on cell migration. Wild type PAI-1 inhibited migration. The presence of P1 Ala PAI-1 mutant not only prevented migration but actually resulted in holes in the monolayer itself indicating detachment of cells from the plate. The anti-Vn antibody had similar effects. In contrast, wild type PAI-1, which binds normally to the Vn binding site, had an intermediate effect above with thinning of the monolayer due to inhibition of migration, but without the stark effect of the holes which were caused by the P1 Ala mutant.

Discussion

Vn has known profound effects on the properties of PAI-1. In addition to stabilizing PAI-1 in the active conformation (Declerck, P. *Verh. K. Acad. Geneeskd. Belg.* 55:457-473 (1993)), Vn also alters the specificity of PAI-1, rendering it an efficient inhibitor of thrombin (Naski et al., supra) and mediating the clearance of thrombin by cellular receptors (see above). Based on this, the present inventors conclude that thrombin, a known mitogen and chemoattractant (Bar-Shavit, R. et al., *Cell Regul.* 1:453-463 (1990)) may promote cell migration by removing PAI-1 from Vn. Others have shown that both elastase and cathepsin G produced by activated neutrophils can efficiently remove PAI-1 from the matrix (Wu, K. et al., *Blood* 86:1056-1061 (1995)). Since PAI-1 is a substrate for these latter proteinases, only catalytic amounts would be required to inactivate PAI-1. This could account in part for the remarkable ability of these cells to migrate.

Together, the above findings indicate that a wide variety of proteinases, even those which are not targets for PAI-1, are able to interact with PAI-1 and expose the RGD integrin binding site on Vn. Such a general ability of many divergent proteinases to modify cellular adhesive properties through a common mechanism suggests that the known relationship between increased cell migration and proteinase activity in a wide variety invasive cellular processes is mediated at least in part by proteolytic interaction with PAI-1. The present inventors also conclude that the role of proteinases in cellular migration may not simply be that of generalized matrix degradation but rather the generation of cell attachment sites through specific interaction with PA-1.

EXAMPLE V

Characterization of the Binding of Different Conformational Forms of PAI-1 to Vitronectin The inventors examined the binding of different conformation forms of PAI-1 to both native Vn (nVn) and urea-purified Vn (uVn) using a solid phase binding assay and found that active PAI-1 binds to uVa with approximately 6-fold higher affinity than to nVn. In contrast, inactive forms of PAI-1 (latent, elastase cleaved, synthetic reactive center loop peptide annealed, or complexed to PA's) displayed greatly reduced affinities for both forms of adsorbed Vn, with relative affinities reduced by more than 2 orders of magnitude. Structurally, these inactive conformational all differ from active PAI-1 by insertion of an additional strand into β-sheet A, suggesting that the rearrangement of sheet A is responsible for reduced Vn affinity. This is further supported by the observation that PAI-1 associated with b-anhydrotrypsin (which does not undergo rearrangement of β-sheet A) showed no decrease in affinity, whereas PAI-1 complexed to b-trypsin (which does undergo sheet A rearrangement) displayed reduced affinity for Vn similar to PAI-1:PA complexes. Together the results demonstrates that the interaction between PAI-1 and Vn depends on the conformational state of both proteins, and suggest that the Vn binding site on PAI-1 sensitive to structural changes associated with loss of inhibitory activity.

As described above, PAI-1 bound to Vn in the extracellular matrix has been shown to block the binding of integrins (Stefansson, S. et al. (1996) *Nature* 383:441-443) and uPAR (Deng, G. et al. (1996) *J. Cell Biol.* 134:1563-1573) to Vn, and this interaction inhibited cell adhesion and migration on Vn. The precise nature of the PAI-1/Vn interaction has been the subject of considerable debate. Using solid-phase binding assays to quantitate this interaction, several studies mentioned above suggested that only active PAI-1 binds Vn; however, others reported no apparent difference in the binding of active and latent PAI-1 (Salonen et al. supra; Kost et al., supra). In addition, the reported dissociation constant for PAI-1 binding to immobilized Vn ranges from 0.3 nM to 190 nM. The Vn binding domain wihtout PAI-1 is localized to a region on the surface of PAI-1 that includes b-strand 1A. The Vn binding site for PAI-1 appears to be located to the somatomedin B domain at the N-terminus of Vn, although other reports suggested that PAI-1 binds to the C-terminus of Vn, between residues 348 and 370 (Kost et al., supra ), or to a site near the center of Vn between amino acids 115 and 121 (Mimuro et al., *Biochemistry* 32:2314-2320 (1993)).

The present inventors postulated that a critical dependence of the PAI-1/Vn interaction on the PAI-1 and/or Vn conformation could explain these conflicting reports. To test this hypothesis the following studies were performed in which the binding of PAI-1 in six different conformations to immobilized nVn and uVn were examined. The results indicated that the two forms of Vn bind to PAI-1 with markedly different affinities and that the Vn binding domains on PAI-1 is very sensitive to the PAI-1 conformation. There may have been an evolutionary selection of the PAI-1 structure to permit efficient removal of inactive PAI-1 at sites of subcellular attachment.

Experimental Procedures

Materials. Purified PAI-1, either active(>95%) or latent (>95%), were obtained from Molecular Innovations (Royal Oak, Mich.). To eliminate any active PAI-1 present in the latent preparations, latent PAI-1 was treated with a 1/100 molar equivalent of elastase for 30 min. at 23° C. in Tris buffered saline, pH 7.5 (TBS) followed by inactivation of the elastase with 1 M (final concentration) PMSF. Purified nVn was obtained from Dr. D. Mosher, and uVn was either received from Dr. T. Podor or purchased Calbiochem. Recombinant high molecular weight uPA was obtained from Dr J. Henkin of Abbott Laboratories, and tPA (Activase) was from Genentech. Porcine pancreatic elastase was from Elastin Products, and bovine b-trypsin and b-anhydrotrypsin as described earlier. The eight residue synthetic peptide Ac-Thr-Val-Ala-Ser-Ser-Ser-Thr-Ala corresponding to the PAI-1 reactive center loop from $P_{14}$ to $P_7$, residues 333-340, was synthesized by the University of Michigan Biomedical Research Core Facilities.

Generation of cleaved and complexed form of PAI-1 was accomplished as described in Example III supra.

PAI-1 binding to Vn was determined either functionally as describe din Example III, or in a Vn specific ELISA as previously described (Lawrence et al., 1994, supra. Briefly, Vn at 1 µg/ml in phosphate buffered saline (PBS), was coated overnight onto Immulon 2 (Dynatech) microtiter plates in a volume of 100 µl at 4° C., and all subsequent steps were performed at room temperature. The plates were washed with PBS followed by $dH_2O$, allowed to air dry for 15 min., and then blocked with 200 µl of 3% bovin serum albumin in PBS for 30 minutes. Next, PAI-1 samples in TBS, containing 100 µg/ml BSA and 0.01% Tween 80 were added, in a final volume of 100 µl, and incubation continued for one hour, after which the unbound PAI-1 was washed away. During this incubation period <15% of the active PAI-1 should have converted to the latent form, since we have determined the $t_{1/2}$ for this conversion to be ~8 hours at 25° C. in the absence of Vn (data not shown). In the functional assay PAI-1 binding was determined by reacting the bound PAI-1 with 0.7 nM uPA for 30 minutes followed by the addition of the chromogenic substrate S-2444 (Kabi) as described by Lawrence et al. (*J. Biol. Chem* 265:20293-20301 (1990)). The PAI-1 bound was then calculated from the loss of uPA amidolytic activity. $K_d$s for the solid-phase binding of PAI-1 to immobilized Vn were calculated using the following form of the standard binding equation from the GraFit program (Eritacus Software):

$$y=[L] \ Cap/(K_d+[L])  \hspace{2cm} \text{Equation 1}$$

where y is the amount of PAI-1 bound, L is free PAI-1 and "Cap" is the Vn capacity for PAI-1 binding.

The Vn dependent ELISA assay was performed as above except that bound PAI-1 was detected with affinity purified, rabbit anti-PAI-1 antibodies and streptavidin conjugated to alkaline phosphatase using the substrate p-nitrophenyl phosphate, disodium (Sigma) at a concentration of 4 mg/ml 100 mM Tris-HCl pH 9.5, 5 mM $MgCl_2$. To control for nonspecific binding all assays were simultaneously analyzed on plates coated with BSA alone and processed in parallel. The background binding to BSA was subtracted from all samples prior to data analysis. For examination of the PAI-1-ahnydrotroypsin complex binding to Vn, 1 µM (final concentration) of anhydrorypsin was included in all wells during the PAI-1 incubation step. This concentration of anhydrotrypsin was 20-fold higher than the highest concentration of PAI-1 tested, and ten-fold than the reported $K_d$ for the interaction of PAI-1 and anhydrotrypsin (17). For data analysis of ELISA experiments, the $K_d$ was estimated for active PAI-1 with equation 1 above by assuming that PAI-1 bound as a percent of the maximal binding was proportional to the actual PAI-1 and that free PAI-1 was approximately equal to PAI-1 added. For the inactive PAI-1 samples examined no value for $K_d$ could be established since none of these samples achieved saturation at the concentrations tested.

Competitive Inhibition of PAI-1 Binding to Immobilized Vn By Solution-Phase Vn

Microtiter plates were coated with nVn, and blocked with BSA as above. Next, either native or urea-purified Vn was added to the plate and serially diluted three-fold in TBS, containing 100 µg/ml BSA and 0.01% Tween 80, after which active PAI-1 was added to a final concentration of 2 nM (final volume 100 µl). The samples were allows to react for 1 hour at 23° C., washed and bound PAI-1 determined as in the ELISA assay as above. $IC_{50}$ values for the inhibition by solution-phase Vn were calculated using a four parameter logistic fit from the GraFit program (Erithacus Software). The $K_d$ for solution-phase interaction of PAI-1 with Vn were determined by analysis of competition data by methods previously described (Olson, S. T. et al., (1991) *Arch. Biochem. Biophys.* 286, 533-545). According to this analysis, the concentration of PAI-1 bound to the competitor Vn in solution is equal to the difference between the total PAI-1 concentration used in the presence of the competitor and the total PAI-1 concentration yielding as equivalent extent of saturation of the immobilized Vn in the absence of the competitor. The latter was calculated based on the fit of binding data in the absence of competitor Vn (FIG. 37) by equation 1. Knowledge of the concentrations of PAI-1 bound to competitor Vn in solution allowed calculation of the concentration of free PAI-1 and free competitor Vn for the solution interaction from which $K_d$ was calculated. Reasonable agreement was obtained for $K_d$ value determined at competitor Vn concentrations yielding significant extents of displacement of PAI-1 from the immobilized Vn (>15%).

Results and Discussion

Figure 35:
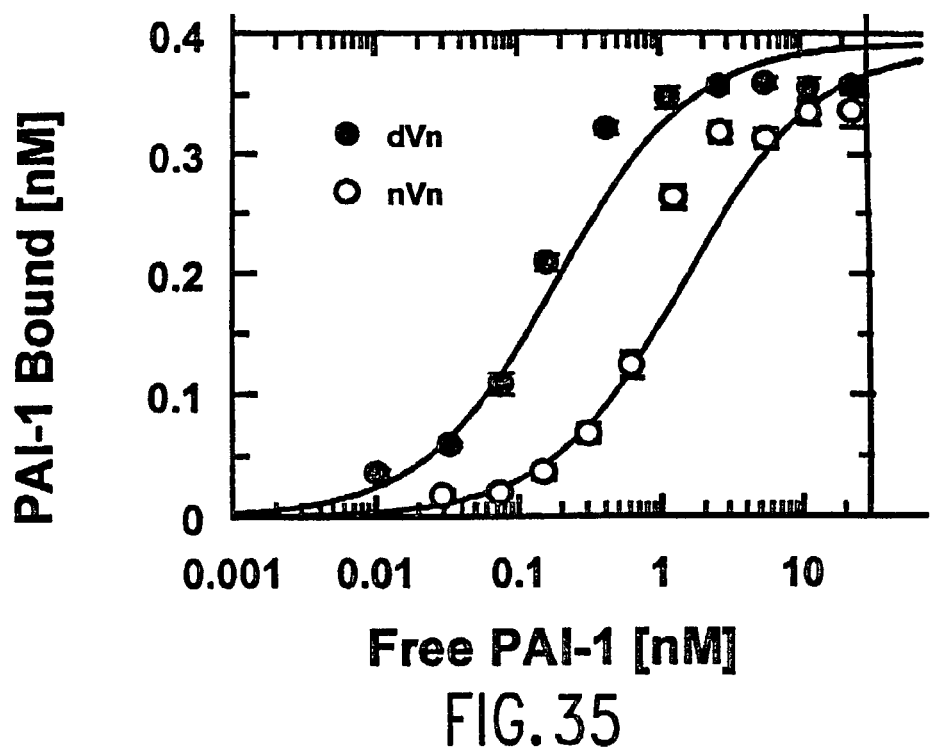
FIG. 35 shows a functional assay for the binding of recombinant active wtPAI-1 to native or urea-purified Vn. The amount of active PAI-1 bound was determined functionally. Active wtPAI-1 binding to nVn (○); or uVn (●). Data points represent the average of at least four separate determinations for each sample ±the S.E.M, and the plots were generated with the GraFit program (Erithacus Software).

The basis for the debate in the literature concerning the interaction between Vn and PAI-1 may be the conformational variability of both proteins. This study directly examined the binding of alternative conformations of PAI-1 to both native and urea-purified Vn. Previously, we described a functional assay for PAI-1 binding to Vn, in which active PAI-1 was shown to bind specifically to surface adsorbed nVn in a dose dependent and saturable manner. This assay was used to compare the binding of active wtPAI-1 to both forms of immobilized Vn (FIG. 35). These results demonstrated that both urea-purified and native Vn have a similar binding capacity for active PAI-1, and that active PAI-1 binds to both forms with high affinity. However, the calculated $K_d$ for the immobilized uVn is approximately 6-fold lower than for immobilized nVn (127±20 pM compared to 825±190 pM). This difference may reflect the different conformational states of the two Vn preparations, since nVn is predominantly monomeric, while uVn is a disulfide linked multimer. The observation that PAI-1 has a higher affinity for immobilized multimeric Vn than for immobilized monomeric Vn is consistent with the result that PAI-1 isolated from plasma is predominantly completed with a high molecular weight form of Vn even though the majority of Vn in plasma is monomeric.

Figure 36:
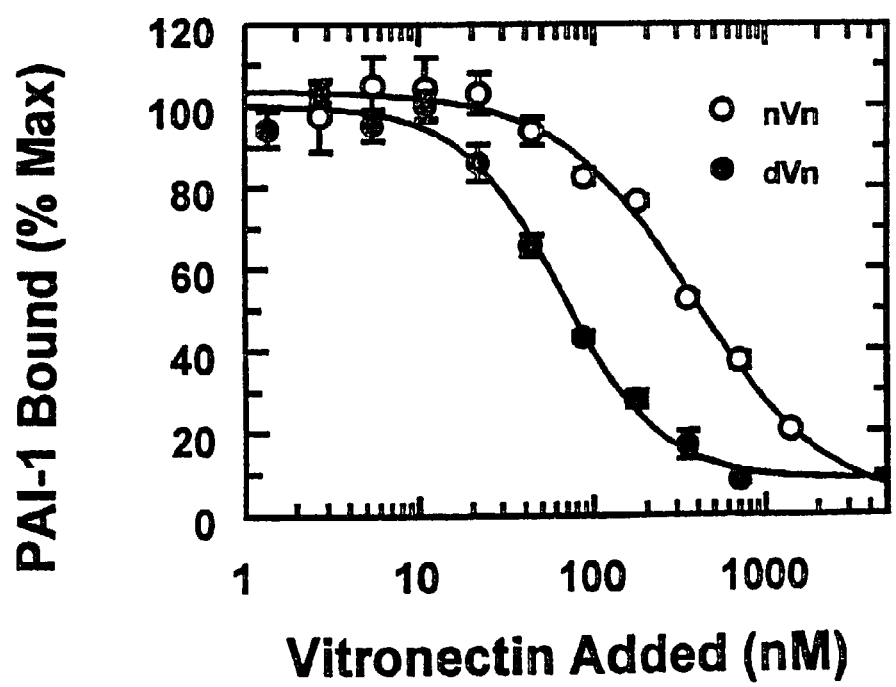
FIG. 36 shows competitive inhibition of PAI-1 binding to immobilized nVn by solution-phase Vn. The amount of PAI-1 bound to nVn is plotted vs. the concentrations of solution-phase native or urea-purified Vn. PAI-1 bound was determined by ELISA. Competition of PAI-1 binding by nVn (○); or by uVn (●). Data points and generation of plots (four parameter logistic fit) were as described for FIG. 35.

Therefore, to see if solution-phase multimeric Vn also bound PAI-1 with higher affinity than solution-phase monomeric Vn, competitive inhibition assays were performed with both nVn and uVn competing for PAI-1 binding to immobilized nVn. These results shown in FIG. 36 demonstrate that both uVn and nVn compete for PAI-1 binding to immobilized nVn. This suggests that PAI-1 binds to the same site on both nVn and uVn, either when th Vn is in solution or immobilized. Furthermore, solution-phase uVn is a more efficient competitor for PAI-1 binding ($IC_{50}$=65 nM) than is solution-phase nVn ($IC_{50}$=375 nM). This approximate 6-fold difference is similar to that shown in FIG. 35, and indicates that either in solution or when immobilized, uVn has a higher affinity for PAI-1 than does nVn. $K_d$ values of 20±1.4 nM and 125±12 nM for the interaction of PAI-1 with solution forms of uVn and nVn, respectively, were calculated from these data. This indicates that PAI-1 binds to immobilized Vn with a significantly higher affinity than to solution-phase Vn, having an approximately 150-fold higher $K_d$ for the solution-phase interaction with either form of Vn. This enhanced binding to immobilized Vn may result from the different conformation that Vn is known to assume when it adsorbs to a surface (Stockmann, A. et al., *J. Biol. Chem.* 268:22974-22882(1993); Preissner, K. T. et al., *J. Biol. Chem.* 265:18490-18498 (1990)).

Figure 37:
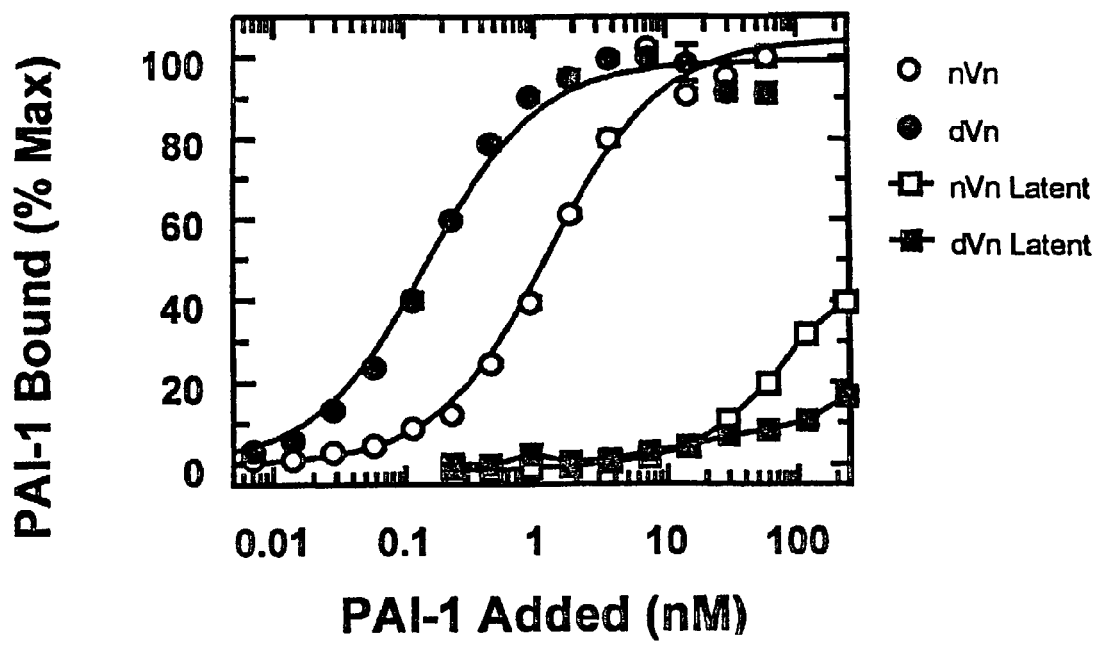
FIG. 37 shows binding of recombinant active or latent wtPAI-1 to native Vn (nVn) or urea-purified Vn (uVn)-coated microplates. The amount of PAI-1 bound was determined by ELISA. Open symbols show PAI-1 binding to nVn and filled symbols indicate PAI-1 binding to uVn. Active PAI-1 (○, ●); Latent PAI-1 (□, ■). Data points and generation of plots were as for FIG. 35.

To examine the binding of alternative conformational forms of PAI-1, an ELISA based assays was performed similar to the solid-phase assay described above except that PAI-1 is detected with an anti-PAI-1 antibody, permitting analysis of inactive conformations of PAI-1. FIG. 37 shows the binding of both active and latent PAI-1 to surface-adsorbed urea-purified and native Vn. Analysis of the binding of active PAI-1 to the two forms of immobilized Vn yields calculated $K_d$s of 150±16 pM with uVn and 1300±200 pM with nVn. These values are similar to those calculated using the PAI-1 functional assay (FIG. 35), indicating that the indirect antibody assay is also for evaluating PAI-1 binding to immobilized Vn. In contrast to activate PAI-1, latent PAI-1 binds to both forms of immobilized Vn with much lower affinity. In this case a $K_d$ could not be determined since saturable PAI-1 binding was not obtained at the concentrations tested. However, if we assume that latent PAI-1 is binding with the same stoichiometry as active PAI-1, then we can estimate a minimum value for $K_d$ of >225 nM (the highest concentration tested) in both cases (FIG. 37). These results are consistent with previous reports that only active PAI-1 binds to Vn with high affinity, and contradict the suggestion by others that both forms of PAI-1 bind Vn with equal affinity.

The $K_d$s calculated for active PAI-1 binding to immobilized Vn were similar to previously reported values. 127 pM vs. 300 pM (Seilffert et al., 1991, supra) with uVn, a 825 pM vs. 4.4 nM (Lawrence et al., *J. Biol. Chem.* 1994, supra) with nVn. An earlier report that calculated a lower affinity $K_d$ of 55-190 nM for these interactions using a similar assay failed to account for the presence of both active and latent PAI-1 in the preparation and may have been measuring primarily the binding of latent PAI-1 (Salonen et al., supra). Consistent with this interpretation, the reported $K_d$ of 190 nM is similar to our estimated minimum $K_d$ for latent PAI-1 binding to either native or uVn ($K_d$>225 nM) (FIG. 37). Salonen et al. also noted a high affinity, "low capacity" binding site ($K_d$<100 pM) that may have represented the active PAI-1 in their preparation.

The observation that latent PAI-1 binds to Vn with a much lower affinity than active PAI-1 suggests that the conformational change associated with conversion to the latent form may be responsible for the reduced affinity. We suggested earlier (Lawrence et al., supra) that the stabilization of PAI-1 by Vn occurs when Vn binding to strand 1 of β-sheet A limits the mobility of β-sheet A necessary for insertion of the PAI-1 RCL during transformation to the latent conformation. This model is compatible with the observation that conversion of the serpin β-sheet A from a five stranded to a six stranded antiparallel β-sheet by insertion of the RCL as strand 4 of β-sheet A, requires extensive rearrangement of b-strands 1, 2 and 3. Restriction of this rearrangement by Vn could retard loop insertion and thus the conversion of PAI-1 to the latent form. Also consistent with this model is the apparent modification of the Vn binding site on PAI-1 following RCL insertion, as indicated by he reduced affinity of latent PAI-1 for Vn (FIG. 37).

Figure 38:
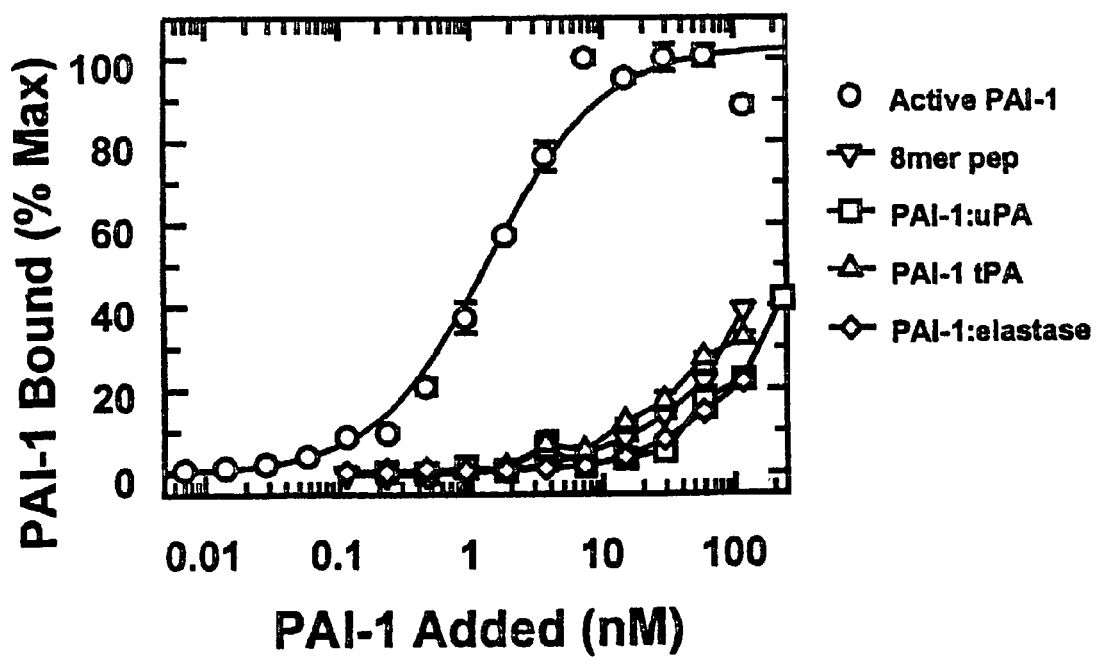
FIG. 38 shows the binding of active PAI-1 (○), PAI-1:tPA complex (Δ), PAI-1 uPA complex (□), PAI-1 in complex with the synthetic RCL peptide (∇), or PAI-1 cleaved by elastase (◇) to nVn. Assays were performed as in JBC FIG. 3. Data points and generation of plots were as described for FIG. 37.

Next to be examined was the binding of native and uVn to PAI-1 complexed to tPA or uPA, cleaved by elastase, or inactivated by insertion of a synthetic RCL peptide. Each of these conformers is thought to have its β-sheet A in the six stranded form, similar to the structure of latent PAI-1. The results are shown in FIG. 38. Like latent PAI-1, none of these RCL inserted forms of PAI-1 bound to immobilized nVn with high affinity, with all having estimated $K_d$s>112-225 nM (the highest concentrations tested). Similar results were immobilized uVn. The relatively low affinity observed for both the tPA-PAI-1 and uPA-PAI-1 complexes with both forms of Vn is consistent with previous reports that tPA dissociates PAI-1 from solution-phase Vn, and that PAI-1 can be removed from extracellular matrix by treatment with uPA (Mimuro et al., 1987, supra). Of note, PAI-1 in complex with the synthetic RCL peptide showed a reduced affinity for Vn similar to the other loop inserted forms. This indicates that it is not the loss of an exposed RCL that results in a reduction of binding affinity for Vn, since in the PAI-1- peptide complex the natural RCL remains intact and fully accessible. Rather, it appears to be the reorganization of β-sheet A that leads to reduced affinity.

Figure 39:
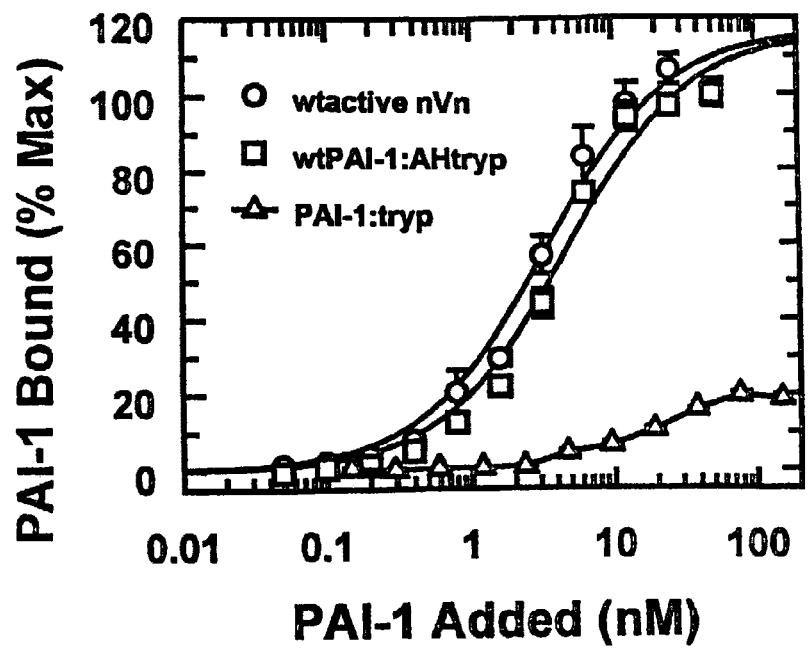
FIG. 39 shows binding of active wtPAI-1 (○), wtPAI-1-trypsin covalent complexes (Δ), or non-covalent PAI-1-anhydrotrypsin complexes (□) to nVn coated microplates. The assay was performed as in FIG. 38, except that for analysis of the PAI-1-anhydrotrypsin complex binding to Vn, 1 µM (final concentration) of anhydrotrypsin was included in all wells during the PAI-1 incubation step. Data points represent the average of at least four separate determinations for each sample±the S.E.M, and the plots for active PAI-1±anhydrotrypsin were generated as for FIG. 37.

To confirm that rearrangement of sheet A (and not simply the association of PAI-1 with an enzyme) was responsible for the loss of affinity, the relative binding affinity of PAI-1 in complex with either trypsin or anhydrotrypsin was tested. PAI-1 is known to be an efficient inhibitor of trypsin and forms SDS-stable, RCL inserted complexes, as with uPA or tPA. In contrast, anhydrotrypsin binds to the PAI-1 RCL in a non-covalent association that does not result in cleavage of the RCL or its insertion into β-sheet A. Like uPA and tPA, PAI-1-trypsin complexes had a very low affinity for immobilized nVn (FIG. 39). However, PAI-1 in association with anhydrotrypsin bound to immobilized nVn with nearly the same affinity as did active PAI-1 alone. This confirms that it is not simply the association of an enzyme with the RCL that leads to a loss of Vn affinity, but instead it is the enzyme induced insertion of the RCL into β-sheet A.

As discussed in other sections, above, recent studies indicate that the serpin mechanism of inhibition is a complex process requiring an exposed RCL. Upon association with a target proteinase the serpin RCL is cleaved at its $P_1$-$P_1'$ bond, and the RCL is inserted into β-sheet A, yielding the stable serpin-proteinase complex. Here, it has been demonstrated that the PAI-1 Vn binding site on the edge of β-sheet A was sensitive to this conformational change in β-sheet A, as well as to similar changes associated with conversion of PAI-1 to the latent form or cleavage in the RCL by a non-target proteinase. This sensitivity may provide a way to ensure the expression of PAI-1 activity at specific sites of action. For example, Vn is believed to localize PAI-1 to the extracellular matrix where it regulates local proteolytic activity (Mimuro et al., supra), and blocks cell adhesion and migration. In this setting it would be beneficial to permit only functionally active PAI-1 to bind to Vn. On a cell surface an inactive ligand can be internalized and degraded. However, this type of regulator may not be as efficient on the less dynamic extracellular matrix. It is proposed, therefore, that to prevent Vn from becoming saturated with inactive forms of PAI-1, a system sensitive to the comformational state of PAI-1, which in turn is closely linked to its activity state, has been selected during evolution.

EXAMPLE VI

The Serpin PAI-1 Inhibits Cell Migration by Blocking Integrin Binding to Vn

The following study shows that Vn significantly enhances SMC migration, and that the specific VNR is required for cell motility. Also demonstrated are (a) the overlap of the attachment site on Vn with the binding site for PAI-1 and (b) the blocking of SMC migration by the active conformation of PAI-1. This effect required high affinity binding to Vn and was not dependent on PAI-1's ability to inhibit PAs. Complex formation between PAI-1 and PAs resulted in loss of PAI-1 affinity for Vn and restored cell migration. These results provide a direct link between PAs and integrin-mediated cell migration, and show that PAI-1 can control cell-matrix interaction by regulating the accessibility of specific cell attachment sites. Hence, the localization of PA activity at sites of focal contact is apparently not there to initiate a proteolytic cascade leading to generalized matrix destruction, but rather is required to expose cryptic cell attachment sites necessary for SMC migration.

METHODS

A PAI-1 Competition of $^{125}$I-VNR Binding to Vn

Active forms of wtPAI-1 (from Molecular Innovations) and PAI-1 mutants were prepared as described by Kvasman et al., supra. Vn was coated onto plates as described in Example III. Radiolabled VNR (2.5 nM) was allowed to bind Vn in the presence of increasing concentrations of WtPAI-1 or PAI-1 mutants. For analysis (with and without uPA), 500 nM PAI-1 was allowed to bind to Vn as above, unbound PAI-1 was then removed, and 5 nM $^{25}$I-VNR added either alone or in the presence of 1 mM uPA or 50 mg/ml LM609 (Chenicon). Assays were processed and analyzed as described.

B. Attachment and Migration of Rabbit SMC on Vn (See Example IV for description of attachment methods) Washed cells were resuspended in serum free media±500 nM of wtPAI-1, Q123K-PAI-1, or R346A-PAI-1 either alone, or with 1 mM uPA or with LM609 (0.5 μg/ml) alone. Cells were allowed to attach to Vn coated plates (1 mg/ml) for 30 min, then washed twice with TBS, fixed in methanol/acetic acid (75/25 v/v), and stained 2% crystal violet. Absorbance of stained cells was measured using a Sony CCD/RGB color video system with Image-1 software (Universal Imaging). Cell attachment to Vn alone was established as 100%, and the attachment of each experimental condition was calculated as a ratio to this value. Analysis of known cell numbers treated similarly indicted that the absorbance was linear over the range of cells examined. Migration assays were performed on Transwells® (3 mm pore size) coated with Vn. SMC were allowed to attach and spread for 45 to 60 min. on the upper chamber in serum free media. Next, 0.5 μg/ml of LM609, or 1 μM wtPAI-1, or PAI-1 with or without 2 mM uPA were added in 0.5% BSA, 1 mM $CaCl_2$; 0.5 mM MnCl2 and Nutridoma® (Boeringer-Manheim). After 4-5 hours the upper cell layer was removed with a cotton swab and cells on the underside of th Transwell were fixed, stained and analyzed as above, with the amount of cell migration observed with Vn alone established as 100%. Migration on Matrigel with and without Vn was as above except that Transwells® were first coated with Matrigel® (1:20 dilution) in serum-free media overnight at 4° C., followed by washing with PBS and blocking with 1% BSA in PBS. Transwells were then incubated±Vn (0.2 mg/ml) followed by washing with PBS prior to addition of cells. Migration was determined after 14-16 hours incubation.

Results and Discussion

The interaction between cells and their substrata is an important regulator of cellular function. During wound healing, migrating cells exhibit enhanced expression of the Vn receptor (VNR) integrins, including which is transiently expressed at the leading edge of cells invading a fibrin clot (Vassalli, J. -D. et al., (1991) *J. Clin. invest.* 88:1067-1072). Like, urokinase plasminogen activator (uPA) is also located at the leading edge of migrating keratinocyes during the early stages of re-epithelization, and migrating vascular cells show elevated expression of uPA and its receptor (uPAR), which localize to focal contacts. Vn enhances this co-localization, and also accelerates the association of the VNR with vinculin at focal contacts. Thus, during wound healing, cells display a similar pattern of expression for uPA and $α_vβ_3$ both temporally and spatially, suggesting a possblie link between these two systems. In vivo, uPA and its inhibitor PAI-1 are important regulators of vascular wound healing. Mice deficient in uPA are protected from neointima formation following vascular injury. However, PAI-1 null mice exhibit excessive intimal thickening due to SMC migration and proliferation, and over-expression of PAI-1 reduces neointima formation to levels similar to uPA null mice. The traditional interpretation of these data is that PAs are required to initiate a proteoplytic cascade at the cell-substratum interface that results in matrix destruction necessary for cellular migration and invasion (Declerck et al., 1988, supra). However, in the current example provides results suggesting a more subtle role for PAs during wound healing, and demonstrating for the first time a direct link between PAs and the VNR integrin.

Figure 40:
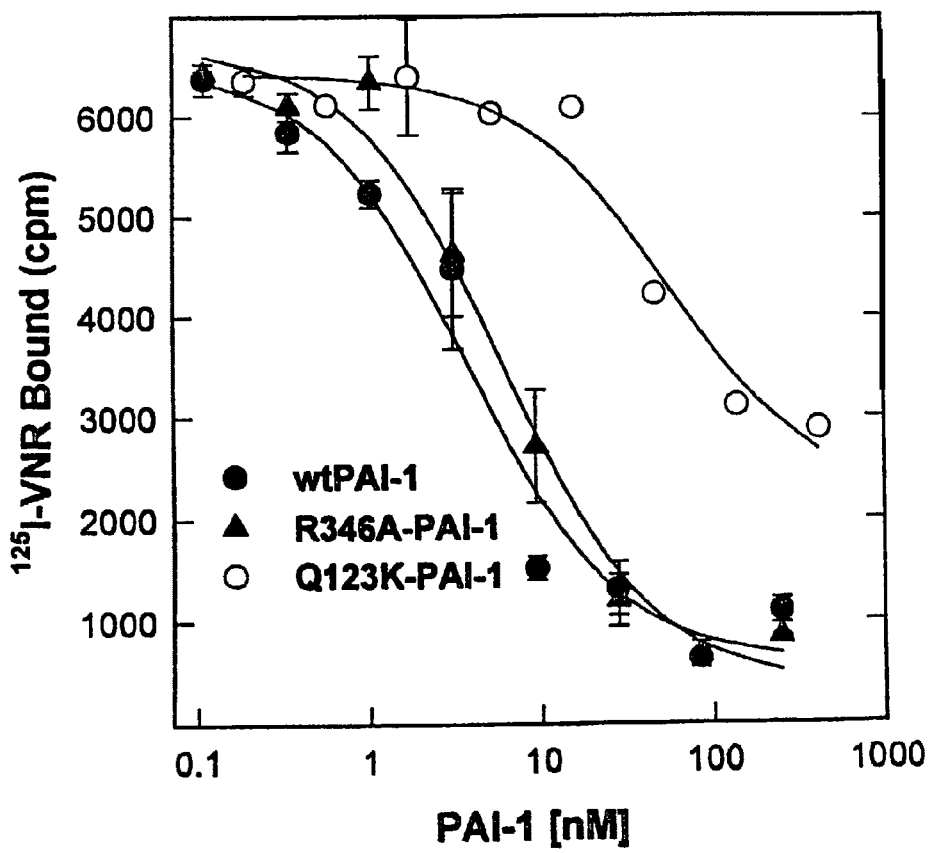
FIG. 40 shows PAI-1 inhibition of $^{125}$I-VNR binding to Vn. Plot of $^{125}$I-VNR bound to Vn vs. the concentration of PM-1 added. wtPM-1 (●), R346A-PAI-1 (▲), and Q123K-PAI-I (○). The data represent the average of 5 experiments performed in duplicate.

The PAI-1 binding site was recently localized to the first 50 residues of Vn, a region that also contains the RGD cell attachment site. To determine whether these binding sites overlap, competition studies between purified radiolabled VNR and PAI-1 for binding to Vn were performed. Wild-type PAI-1 (wtPAI-1) efficiency competed with $^{125}$I-VNR for binding to immobilized Vn (FIG. 40). A mutant PAI-1 (R346A) that binds to Vn normally, but does not inhibit PAs, inhibited the binding of $^{125}$I-VNR to Vn identically to wtPAI-1 (Ki~4 nM). However, a second PAI-1 mutant (Q123K) that inhibits PAs normally, but has a significantly reduced affinity for Vn, was a relatively poor inhibitor of $^{125}$I-VNR binding to Vn. These results demonstrate that PAI-1 binding to Vn was sufficient to block VNR binding. None of the PAI-1 variants had any effect on the binding of $^{125}$I-VNR to fibronectin, indicating that the interaction is specific for Vn, and that the loss of VNR binding is not due to interactions between PAI-1 and the VNR.

Figure 41:
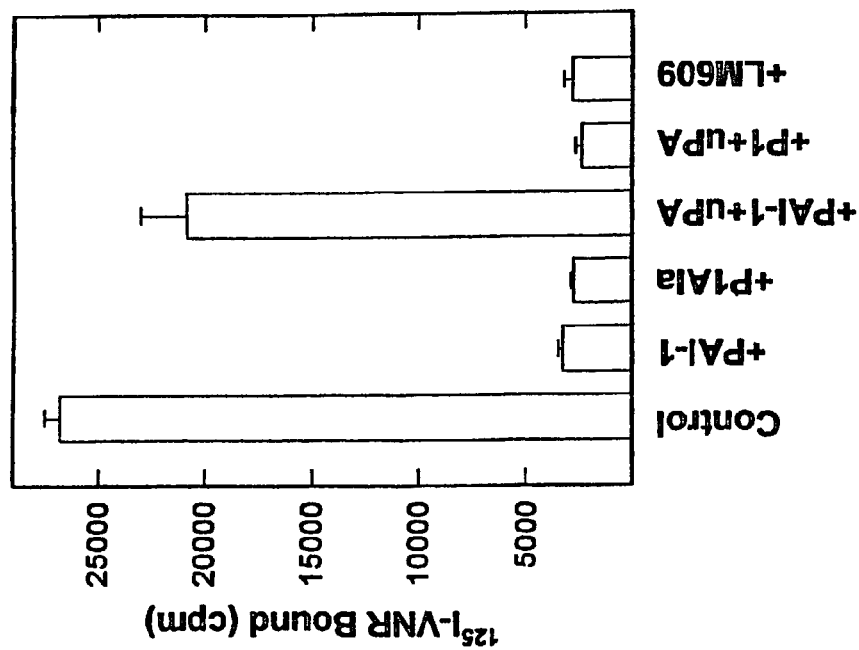
FIG. 41 shows inhibition of $^{125}$I-VNR binding to Vn by PAI-1 with or without uPA. $^{125}$I-VNR bound to Vn in the presence of each competitor. The data represent the average of 2 experiments both performed in duplicate.

PAI-1 undergoes profound conformational changes upon reaction with a proteinase. This structural change results in loss of high affinity for Vn and rapid clearance of the PAI-1:proteinase complex by members of the LDL receptor family. Therefore, to examine the possibility that PAs might regulate integrin attachment by decreasing the affinity of PAI-1 for Vn, competition assays were performed in the presence and absence of uPA. In the presence of a 2-fold molar excess of uPA, the ability of wtPAI-1 to inhibit $^{125}$I-VNR binding to Vn was largely abrogated (FIG. 41). The data are consistent with the PAI-1:uPA complex having a significantly reduced affinity for Vn which permits the receptor to displace the inactive complex. In contrast, uPA did not reduce the inhibition of $^{125}$-VNR binding to Vn by R346A PAI-1. This indicates that uPA enhances VNR binding by forming a complex with wtPAI-1 and is not due to proteolysis of either the VNR or Vn. A monoclonal antibody to $\alpha_v\beta_3$ (LM609) also inhibited the binding of $^{125}$I-VNR to Vn to the same extent as did PAI-1 (FIG. 41), confirming that this VNR preparation contained primarily $\alpha_v\beta_3$ and that PAI-1 blocks the binding of this integrin to Vn.

Figure 42A:
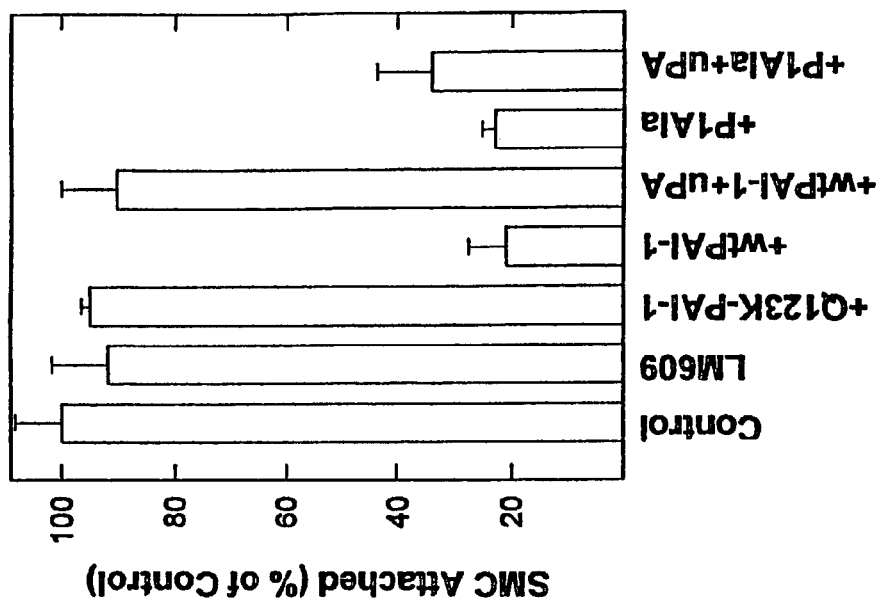
FIGS. 42A and 42B show attachment and migration of rabbit SMC on Vn.

To see whether PAI-1 can inhibit the interaction of cellular integrinsa with Vn in a similar manner, attachment and migration assays using SMC were performed. Both active wtPAI-1 and R346A-PAI-1 inhibited SMC attachment to Vn (FIG. 42A). In contrast, Q123K-PAI-1 had no affect on cell attachment, indicating that the inhibition of cell attachment by PAI-1 is due to its ability to bind Vn ad not its inhibitory activity towards PAs. Furthermore, adding uP to wtPAI-1 and Vn reversed the inhibition of cell attachment, whereas uPA had no affect on the inhibition of SMC attachment by R346A-PAI-1. Interestingly, PAI-1is able to inhibit the attachment of SMC to Vn, while LM609 is not. This suggests that SMC have other integrins that can mediate attachment to Vn through the RGD integrin binding site and that PAI-1 blocks access of these integrins as well. Consistent with this interpretation a synthetic RGD containing peptide also blocked SMC attachment to Vn.

Figure 42B:
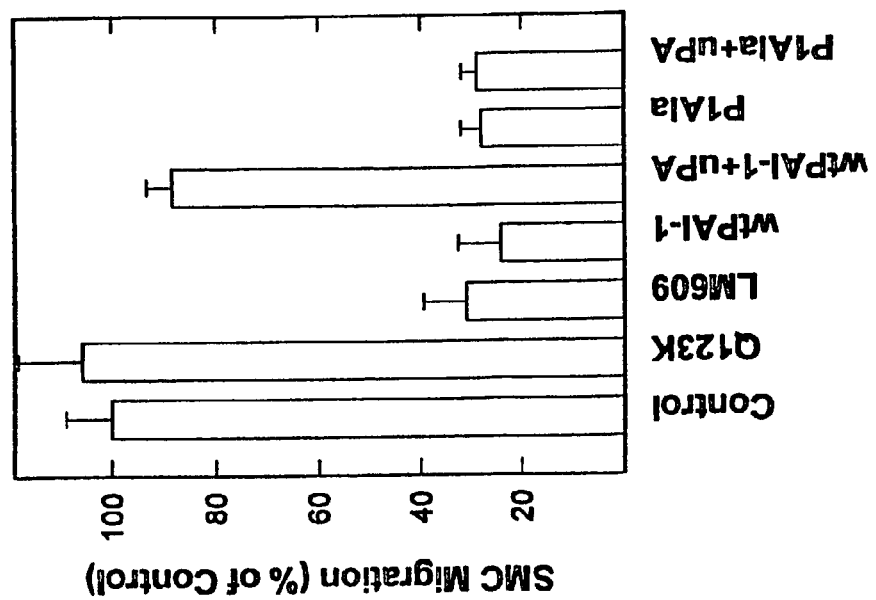

PAI-1 also inhibited the migration of SMC through Vn coated Transwells®. As observed with cell attachment, both active wtPAI-1 and R346A-PAI-1 prevented cell migration, whereas active Q123K-PAI-1 had no affect (FIG. 42B). Inclusion of uPA negated the inhibition of migration by wtPAI-1 but not by R346A-PAI-1. This proved that as with attachment, the inhibition of cell migration was due to PAI-1's capacity to bind Vn and not its inhibitory activity towards PAs. LM609, which did not prevent attachment, inhibited migration, confirming that SMCs require $\alpha_v\beta_3$ for motility. These results are consistent with the observations that migrating vascular cells show elevated expression of both uPA and the VNR and that SMC show enhanced migration on Vn compared to other matrix proteins.

Figure 43:
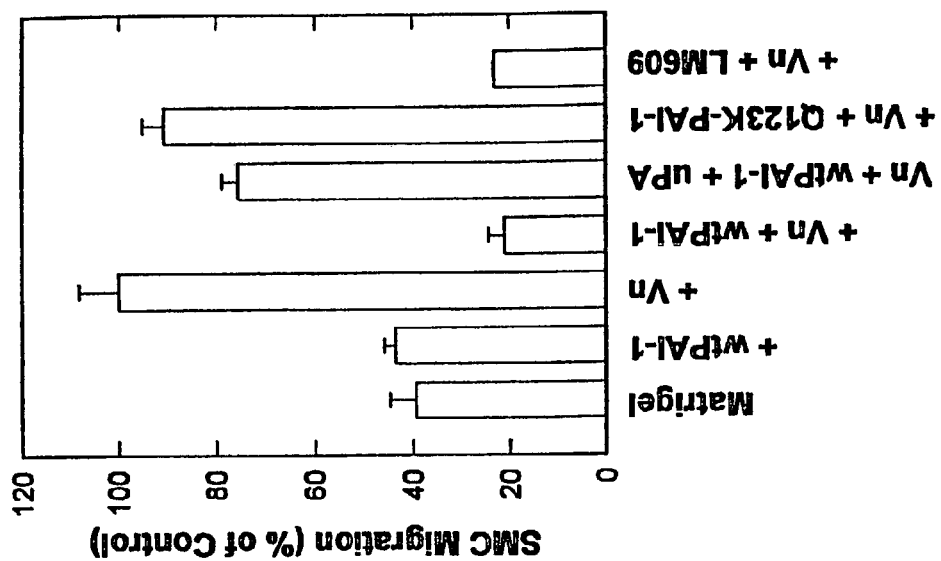
FIG. 43 shows migration of rabbit SMC through Matrigel coated Transwells with or without Vn. The extent of cell migration through Matrigel coated Transwells±Vn in the presence of each competitor. The data represent the average of 3 experiments each performed in duplicate

The results presented above suggest that SMC migration during normal wound healing requires both the cellular expression $\alpha_v\beta_3$ and the presence of Vn in the matrix, and that PAI-1 may act as an important regulator of this process. However, subcellular matrices in vivo are much more complex, containing collagens, glycoaminoglycans, and other proteins such as laminin. Therefore, to examine the role of PAI-1 and Vn in cellular attachment and migration on such a heterogeneous matrix, and to see if PAI-1 could regulate this process, attachment and migration assays were performed on a complex basement membrane matrix derived from murine sarcoma cells (Matrigel®) in the presence or absence of Vn. Unlike cell attachment to purified Vn, PAI-1 had no affect on attachment to Matrigel even in the presence of Vn. This indicates that other proteins in the matrix are support cell attachment, and, as was seen with fibronectin, PAI-1 had no affect on this association. PAI-1 also did not affect SMC migration through Matrigel-coated Transwells in the absence of added Vn. However, adsorption of Vn to the Matrigel markedly increased SMC migration (FIG. 43). This is consistent with previous report demonstrating that Vn significantly enhances migration of both SMC (Lawrence et al., 1995, supra; Wilczynska et al., supra) and primary keratinocytes (Aergeets, K. et al. (1995) *Nature Structural Biology* 2, 891-897) and suggests that the presence of Vn in an exposed matrix or fibrin clot might stimulate cell migration. Furthermore, even though PAI-1 and LM609 had no affect on cell attachment to Matrigel containing Vn, they were able to inhibit cell migration on this matrix (FIG. 43). As with purified Vn, the Q123K-PAI-1 had no effect on cell migration and the addition of uPA reversed the inhibition by wtPAI-1. Together, these results demonstrate that SMC migration on a complex matrix is enhanced by adsorption of Vn, and that this induction is $\alpha_v\beta_3$ dependent. PAI-1 can prevent this induction by blocking $\alpha_v\beta_3$ binding, and PAs can promote the induction by reversing the PAI-1 block. This suggests that in vivo, the binding of plasma Vn to an exposed matrix following injury may act to accelerate cell migration during wound healing, and that PAI-1 may be an important factor regulating this process. Supporting this hypothesis, treatment of Matrigel coated Transwells with bovine serum enhanced SMC migration, in a PAI-1 inhibitable manner. These results are also consistent with the observation that PAI-1 null mice show enhanced SMC migration and proliferation, while in uPA null mice SMC migration is reduced.(Carmeliet, P. et al., *Fibrinolysis* 10 (Suppl. 3):19 (abstr 57) (1996).

The specificity of the inhibition of integrin attachment to Vn by active PAI-1 further illustrates the unique functional interdependence that exist between PAI-1 Vn. In addition to stabilizing PAI-1 in the active conformation, Vn also alters the specificity of PAI-1, making it an efficient inhibitor of thrombin, and promotin its clearance by members of the LDL receptor family. This suggests that thrombin, a known mitogen and chemotactic molecule, migration also promote cell migration by removing PAI-1 from Vn. In addition, several studies have shown that both elastase and cathepsin G produced by activated neutrophils can efficiently remove PAI-1 from the matrix. Since PAI-1 is a substrate for these enzymes, only catalytic amounts are required to inactivate PAI-1. Together the findings indicate that a wide variety of proteinase are able to interact with PAI-1 and expose the RGD integrin binding site on Vn. This general ability to modify cellular adhesive properties by many divergent proteinase through a common mechanism suggests that the known correlation between increased cell migration and proteinase activity may be mediated, at least in part, by proteolytic interaction with PAI-1 in a wide variety of invasive cellular processes. It also that the role of some proteinases in cellular migration may not be to cause generated matrix degradation but instead maybe to expose cryptic cell attachment sites by inactivating PAI-1.

EXAMPLE VII

PAI-1 and Mutants in Cell Attachment, Migration, Angiogenesis and Clearance

The interactions between cells and their substrate is an important regulator of cellular function Signals from the extracellular matrix are conveyed to cell surface adhesion proteins such as members of the integrin family. Integrins bind to immobilized matrix protein and help direct the cellular response to specific surface environments by mediating adhesion and/or migration. Cell migration is an important step in many physiological processes such as wound healing and angiogenesis and is also an important factor in pathologic situations such as tumor progression and metastasis. Under normal conditions cell migration is a tightly controlled proces which depends on the coordination of many factors (Lauffenburger, D. A. et al., *Cell* 84:359-369 (1996)). Following injury the early matrix of a wound is primarily a cross-linked fibrin network associated with significant amounts of vitronectin. During wound healing migrating cells, such as smooth muscle cells (SMC), endothelial cells and keratinocytes, exbibit an increased expression of the vitronectin receptor (VNR) integrins including $\alpha_v\beta_3$ and $\alpha_v\beta_5$ (Liaw,L. et al., *J Clin Invet* 95:713-724 (1995);

Liaw et al., *Circ Res* 77:665-672 (1995); Brooks et al., 1994, supra; Brooks, P. C. et al., *Cell* 79:1157-1164 (1994)). The integrin $\alpha_v\beta_3$ has also been shown to be transiently expressed at the leading edge of cells invading a fibrin clot (Clark R. A. F. et al., *Am J Pathol* 148:1407-1421 (1996)). This association between VNR expression and cellular migration has led to the suggestion that the $\alpha_v\beta_3$ integdn is important for cell motility.

Figure 44:
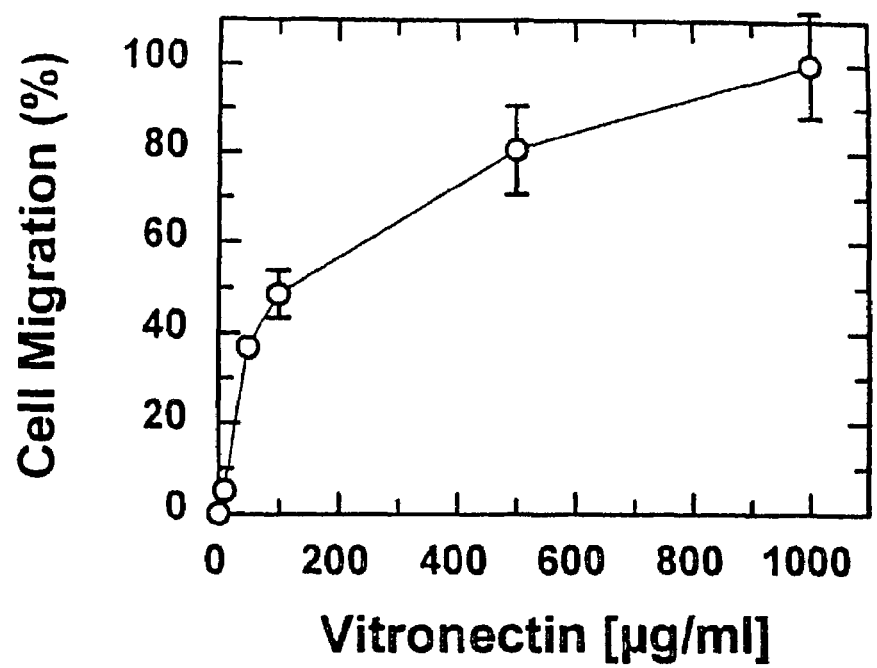
FIG. 44 shows the effect of increasing concentrations of immobilized Vn (Vn) on SMC migration. Vn in TBS was coated onto Transwells at the indicated concentrations and incubated for 2 hours at 37° C. after which the wells were blocked using 3% BSA in TBS. SMC in serum free DMEM media were added to the top Transwell chamber and allowed to migrate for 8 hours. After which the cell migration was assessed (See Example VI).
Figure 45:
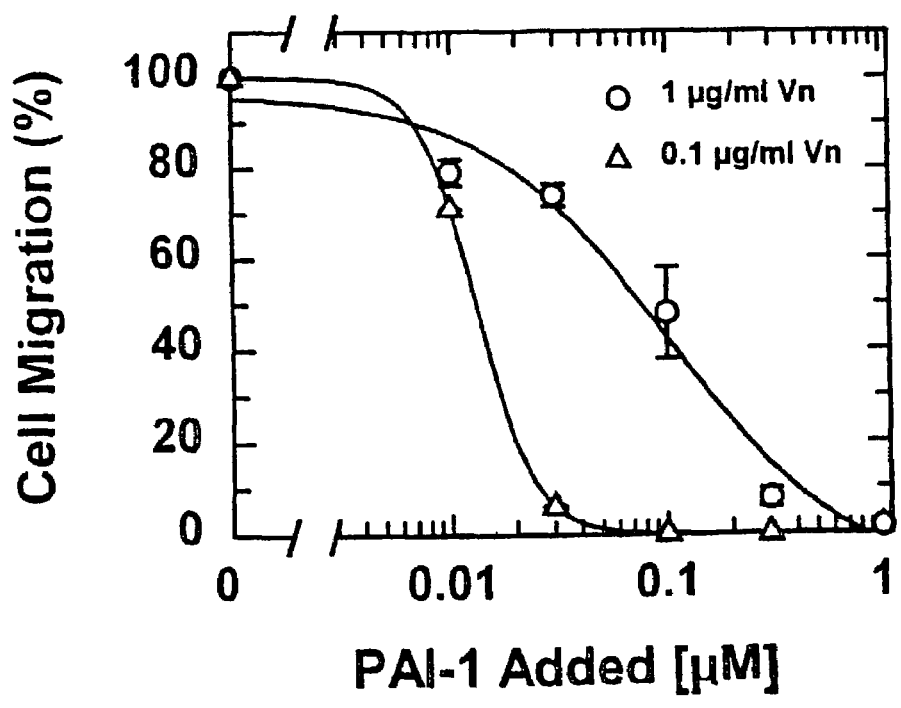
FIG. 45 shows the effect of increasing concentrations of PAI-1 on SMC migration on Vn. Vn was coated onto Transwells as in FIG. 44. SMC in serum free DMEM media were added to the top Transwell chamber and allowed to attach for 30 min. before PAI-1 was added to the cell layer. SMC were allowed to migrate for 8 hours after which the migration was assessed as noted above.
Figure 46:
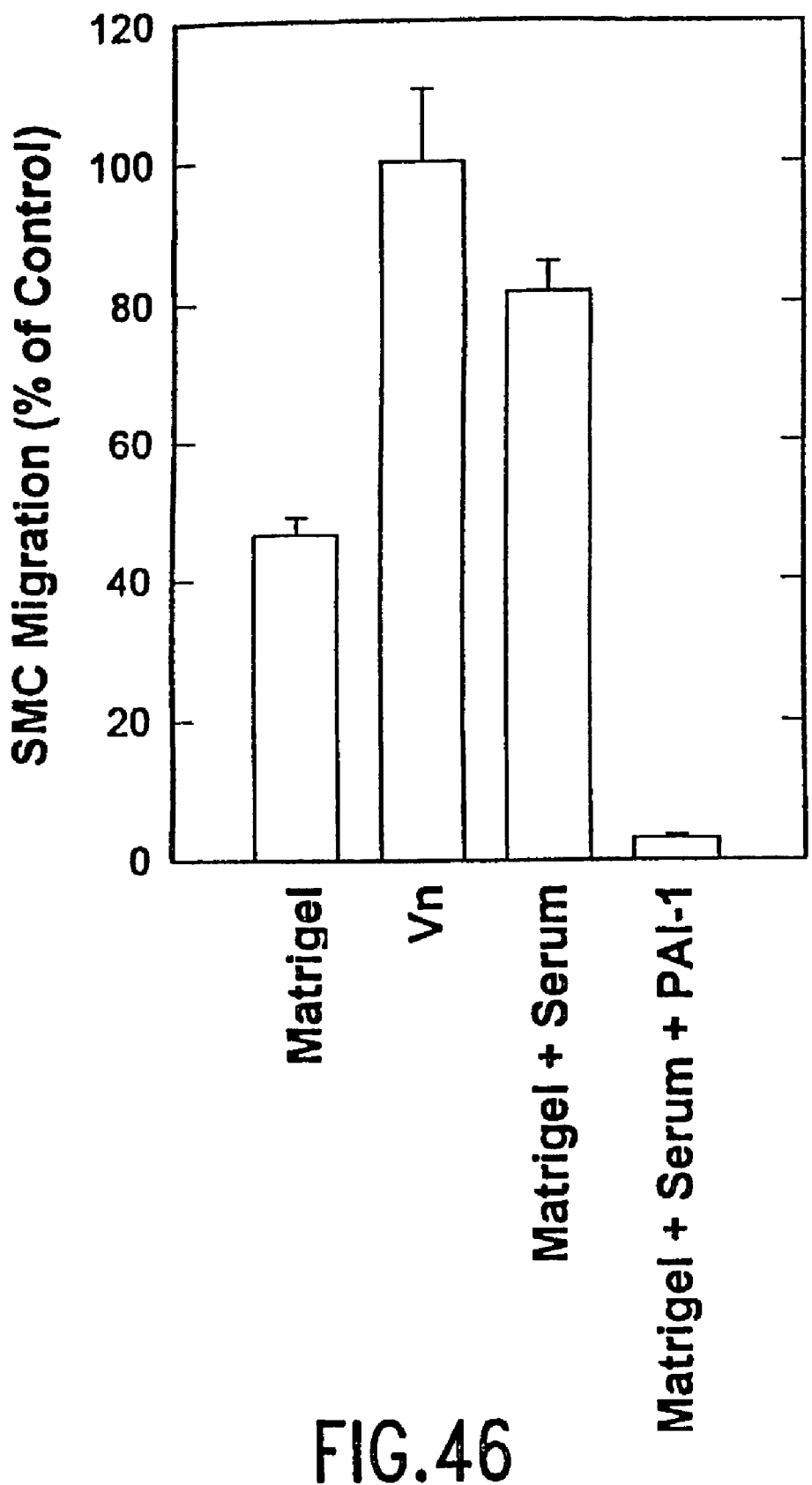
FIG. 46 shows that Vn in serum enhances SMC migration on Matrigel. Transwells were coated with Matrigel (1:20 dilution in TBS) for 2 hours at 37° C. after which the Transwells were washed and incubated with TBS, bovine serum or purified native Vn (0.2 mg/ml in TBS). Cells were allowed to attach for 30 min before PAI-1 (1 µM) was added (fourth bar). Migration was assayed as noted above.
Figure 47:
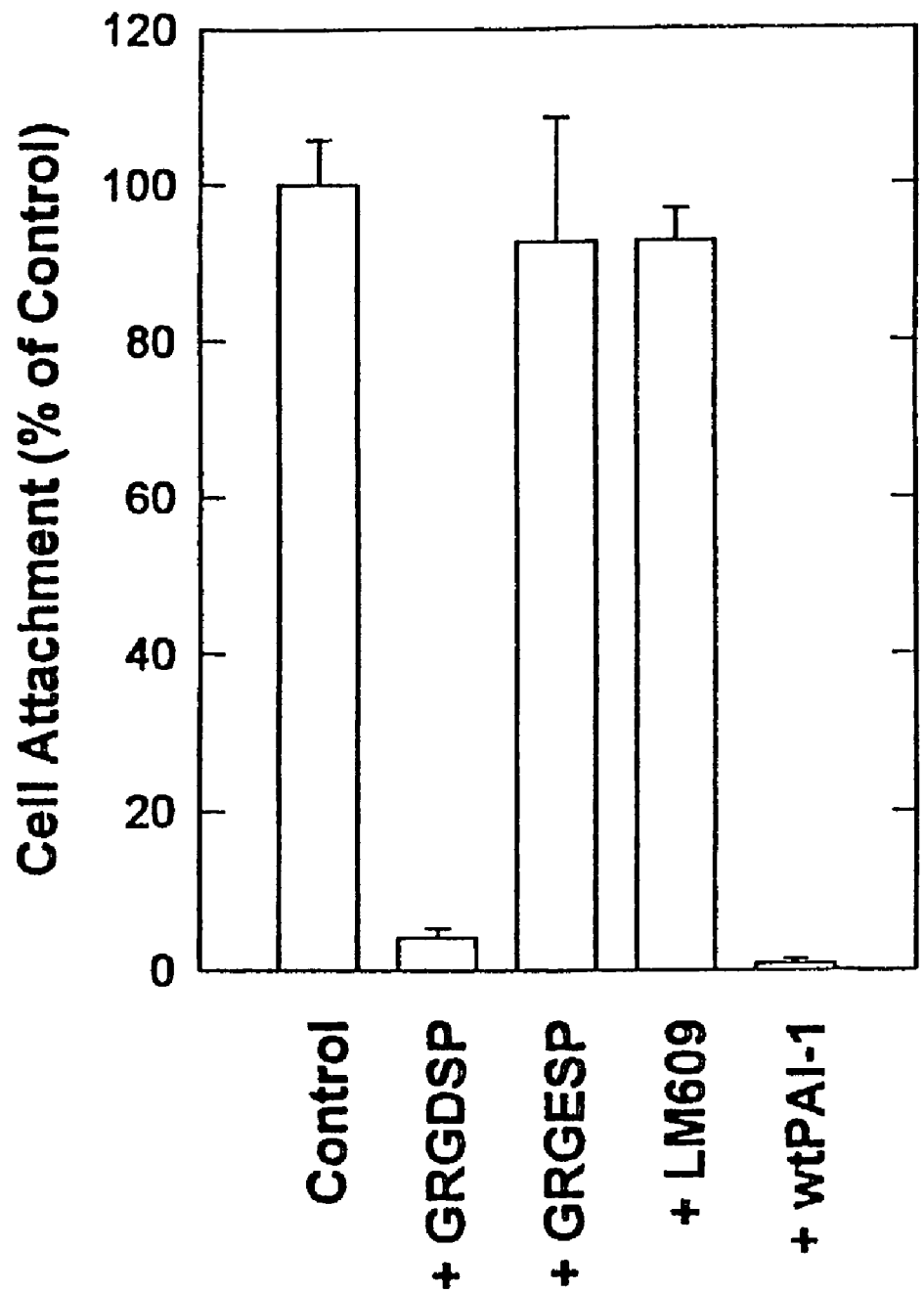
FIG. 47 shows the effect of an RGD peptide on the attachment of SMC to native Vn. Native Vn (1 µg/ml in TBS) was coated onto 96 well plates in incubated for 2 hours at 37° C., after which plates were blocked with 3% BSA in TBS. SMC were added to wells in the absence or presence of the peptides (SEQ ID NO:14) GRGDSP (100 µM in DMEM) or (SEQ ID NO:15) GRGESP 100 µM in DMEM), or LM609 (0.5 µg/ml in TBS) or wtPAI-1 (1 µM in DMEM). Cells were allowed to attach for 45 mm before assay was terminated.
Figure 48:
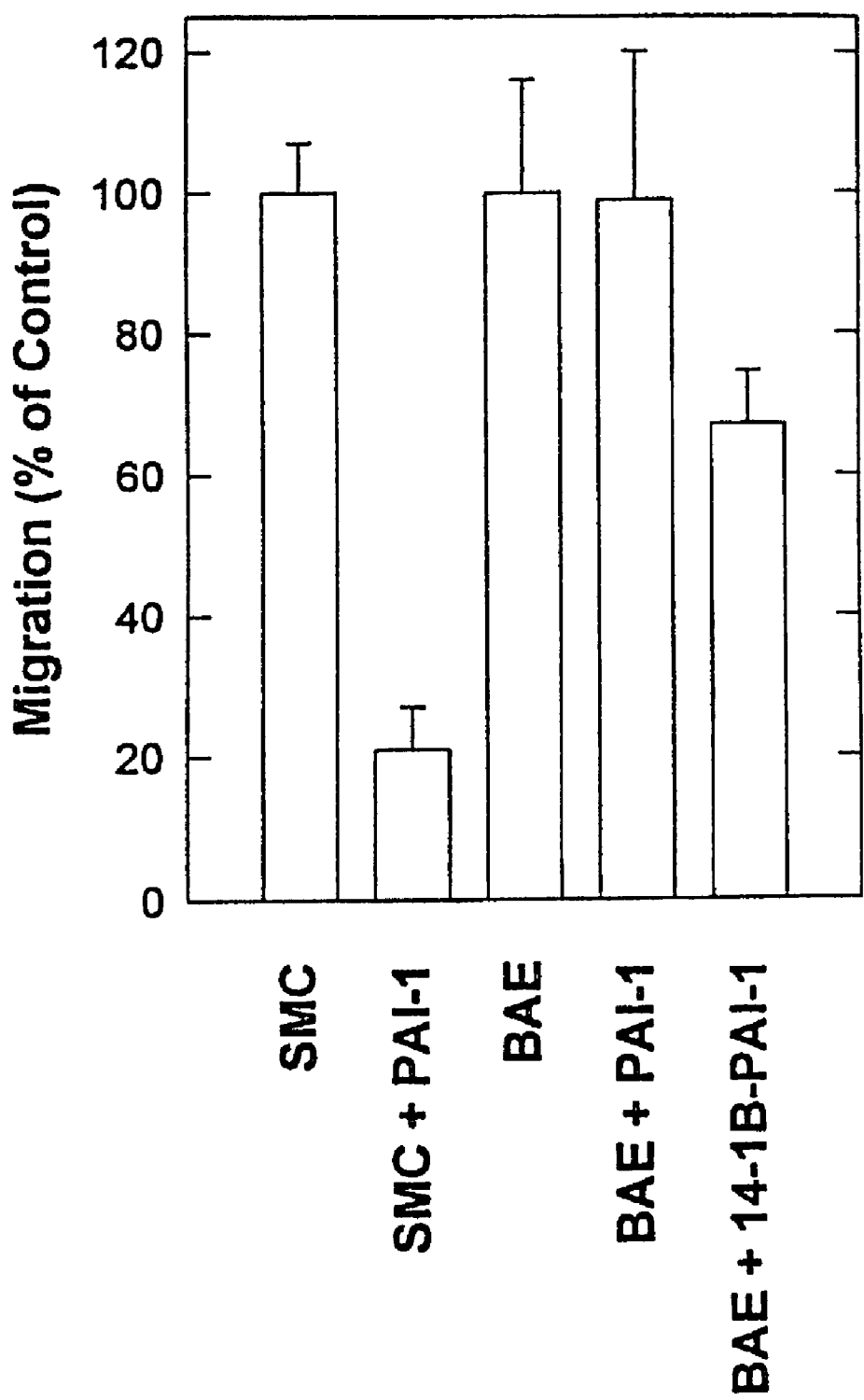
FIG. 48 shows the effect of PAI-1 and RGD peptides on attachment of SMC and bovine aortic epithelial (BAE) cells to native Vn. Native Vn was coated as above. SMC and BAE were allowed to attach to the wells in the presence of the peptide (SEQ ID NO:14) GRGDSP (100 µM in DMEM) or PAI-1 (1 µM in DMEM) for 45 min before prior to termination of the assay.

The present invetors have shown that $\alpha_v\beta_3$ is not required for muscle cell attachment to Vn but is required for cell motility (Example VI). It was also demonsrated that the $\alpha_v\beta_3$ attachment site on Vn overlaps with the bindig site for PAI-1 and that the active conformation on of PAI-1 blocks the attachment and migration of vascular SMCs on Vn. This effect is not dependent on PAI-1 ability to inhibit plasminogen activators (PAs) but does require high affinity binding to Vn. Complex formation between PAs and PAI-1 results in loss of PAI-1 affinity for Vn and restores cell attachment and migration. These data demostrate that PAI-1 can control cell-matrix interactions by regulating the accessibility of specific cell sites and suggest that the location of PA activity at sites of focal conct is not to initiate a proteolytic cascade leading to generalized marix destructon, but insead is required to expose cryptic cell attachment sites on Vn for smooth muscle cell migration FIGS. 44 and 45 show that the SMC migration is affected both by the concentration of Vn which is adsorbed to the Transwell migration chamber (FIG. 44) and that PAI-1 is a more efficient inhibitor of SMC migration at lower Vn coating concentration (FIG. 45). Since Vn in plasma is thought to bind to extravascular matrix upon injury, experiment were done to test whether Vn from serum showed simlar effects. Shown in FIG. 47 is the migration of SMC on Transwell filters coated first with Matrigel and then exposed to either purified native Vn or bovine serum. Consistent with our previous observations, SMC migrated faste on Matrigel in the presence of Vn. Serum also stimulated the migraon of SMC which were inhibited by the addition of PAM-1. This shows that serum Vn has the same ability as purified native Vn to accelerate SMC migration and that PAI-1 is able to inhibit this interaction as well.

The abiliy of PAI-1 to block the binding of cellular integrins to Vn is probably due to the fact that PAI-1 has a greater affinity for Vn than do integrins. Shown in FIG. 47 is a comparison of the ability of PAI-1 to inhibit SMC attachment compared to a peptide containing the RGD sequence to mAb to $\alpha_v\beta_3$ (LM609) The RGD-containing peptide but not a corresponding RGE-containing peptide inhibited all SMC attachment to Vn. Antibody LM609 did not inhibit SMC attachment, consistent with the fact that these cells have other Vn secific integrins. PAI-1, like the RGD containing peptide, could inhibit all SMC attachment to Vn. However it had similar efficacy at approximately a 100 fold lower concentration.

Figure 49B:
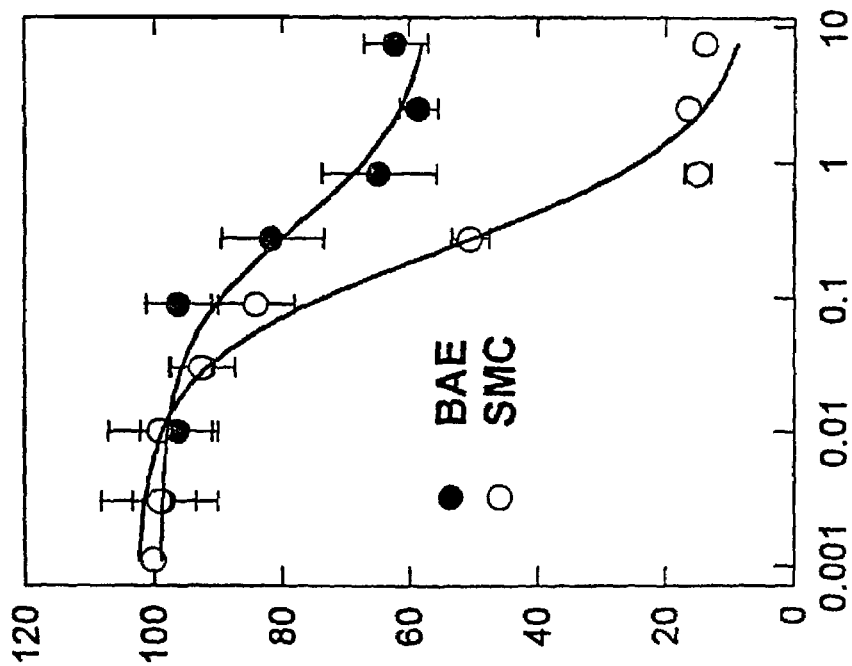
FIGS. 49A and 49B shoWs the effect of RGD peptides (FIG. 49A) and PAI-1 (FIG. 49B) on attachment of SMC and BAE to native Vn. Native Vn was coated as above at 1 µg/ml. SMC and BAE were allowed to attach to the wells in the presence of increasing concentrations of (SEQ ID NO:14) GRGDSP or PAI-1 for 45 min before the assay was terminated.
Figure 49A:
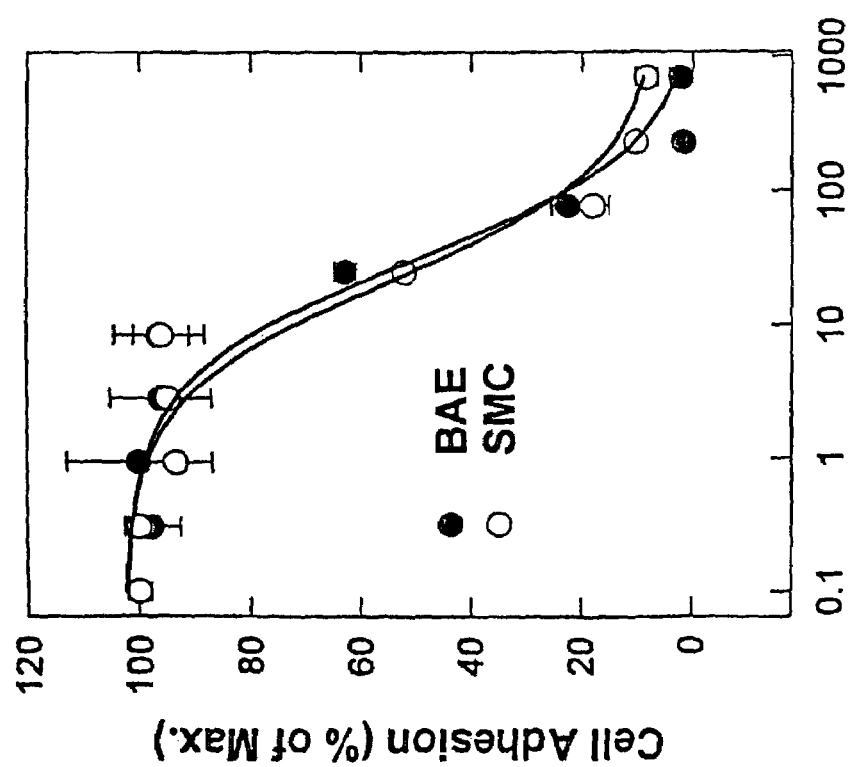
Figure 50A:
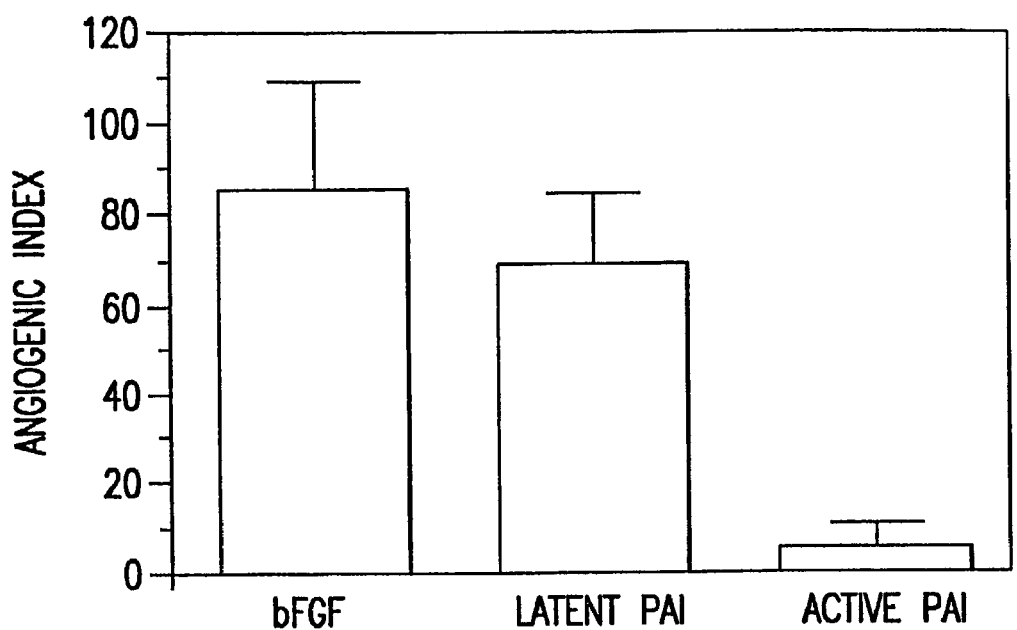
FIGS. 50A-50C show the effect of PAI-1 its mutants on cytokine-induced angiogenesis. Angiogenesis in the chicken chorioallantoic membrane (CAM) was stimulated using basic fibroblast growth factor (Brooks, P. C. et al., 1994, *Science*, 264:569-571).
Figure 50B:
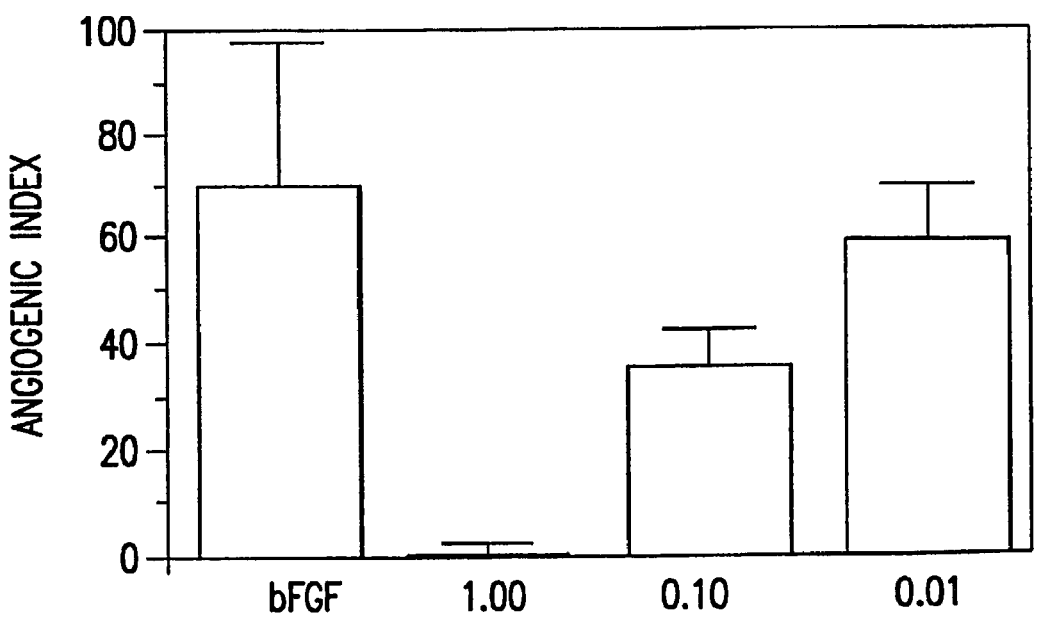
Figure 50C:
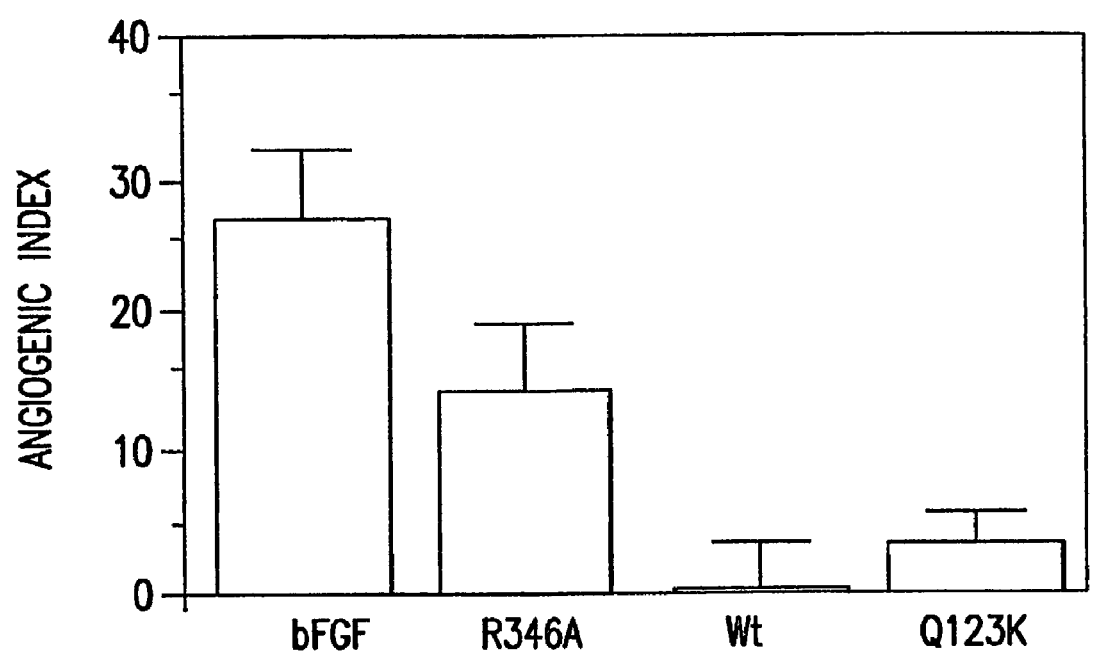

In procses such as wound healing angiogenesis, SMC act in concert with endotelial cells to seal a wound and to produce a funtioning capillary vessel. To evaluate the use of PAI-1 in these processes, studies were done examining the effect of PAI-1 on endothelial cell attachment to Vn using bovine aortic endothelial cells (BAE). FIGS. 43 and 49A-49B show that PAI-1 was unable to inhibit the attachment of BAE to Vn to the same extent as the RGD-containing peptide. A possible explanation is that endothelial cells having other RGD binding integrins that are able to recognize other sites on Vn, distal to the from normal cell attachment site and the PAI-1 binding site. In addition to blocking SMC migration in vitro, PAI-1 also blocked cytokine-induced angiogenisis in vivo (FIG. 50A-50C). These results were obtained using the stabilized 14-1B mutant which has four amino acid substitutions compared to wild-type (N150H, K154T, Q319L, M354I). These results show that this stabilized PAI-1 and additionl PAI-1 mutants inhibit angiogenesis in the chicken chorioallantoic membrane (CAM). At least part of the inhibition is due to blocking Vn accessibility.

Apart from PAI-1-mediated inhibition of cell attachment and migration, which is dependent on high affinity binding to Vn, other uses of PAI-1 mutants exploit the high affinity that PAI-1 has for clearance receptors upon complex formation with proteinase. PAI-1 proteinase complexes show higher affinity for the clearance receptors LRP and gp330 than other serpin enzyme complexes tested. Shown in FIG.

51 is the cell mediated degradation of $^{125}$I-neutrophil elastase by either PAI-1elastase inhibitor mutant (R346A) compared to the natural proteinase inhibitor α1-proteinase inhibitor. This e;levated degradation occurs via endosomes and lysosomes since it is inhibited by chloroquine.

Figure 52:
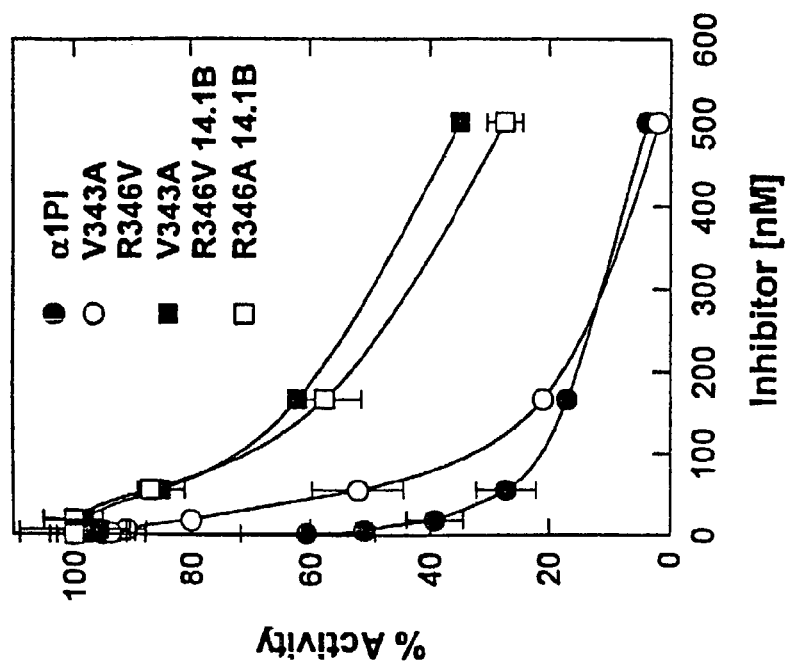
Figure 51:
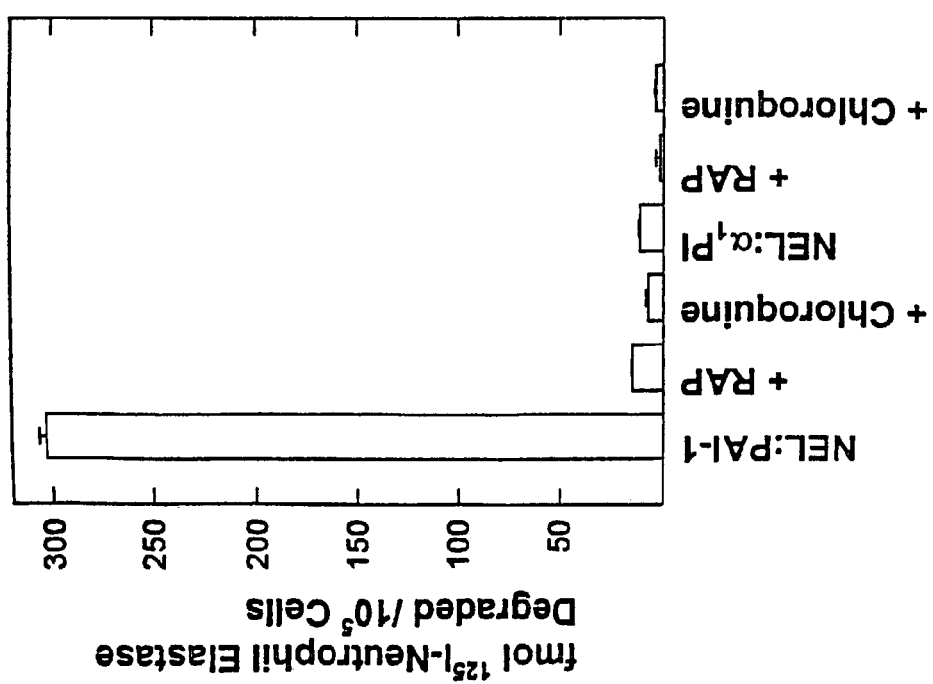
FIG. 51 shows a comparison of the cellular degradation of human neutrophil elastase (NEL) in complex with either PAI-1 or α1-proteinase inhibitor ($α_1$PI). The cellular clearance of a PAI-1 mutant able to inhibit neutrophil elastase) complexed to NEL (NEL:PAI-1) was compared to a complex of NEL with $α_1$PI (NEL-$α_1$PI). Preformed complexes of $^{125}$I-NEL (25 nM) with PAI-1 or $α_1$-PI were added to mouse embryo fibroblasts (MEF) cultures. Degradation of the complexes were assessed as described (Stefansson, S. et al., 1996, *J. Biol. Chem.* 271:8515-8220). The degradation of NEL-PAI-1 is inhibited by adding the receptor associated protein (RAP, 1 µM)), which antagonizes the binding of all ligands to the LDL-related protein (LRP). NEL degradation was also inhibited by the lysosomal degradation inhibitor, chloroquine (150 µM), FIG. 52 compares the inhibition of human NEL enzymatic activity by PAI-1 mutants and $α_1$-proteinase inhibitor. NEL (2 nM) was incubated with increasing concentrations of "$α_1$PI" (●), a PAI-1 mutant having two amino acid substitutions from the wild type –"V343A R346V" (○), the 14-1B mutant of PAI-1 additionally having two substitutions –"V343A, R346V 14.1B" (■) and the 14-1B mutant of PAI-1 additionally having one substitution –"R346A 14.1B" (□). Residual activity of the elastase was measured by monitoring hydrolysis of N-methoxysuccinyl-Ala-Ala-Pro-Val p-nitroanilide at 405 nm.

Since neutrophil elastase prefers to cleave at the C-terminal side of valine, the present inventors examined whether the efficiency of elastase inhibition by PAI-1 could be improved by introducing a valine residue in the reactive center bond. Additionally it was desired to eliminate valine at position 343, an elastase-sensitive site in wtPAI-1 that leads to inactivation of PAI-1. Shown in FIG. 52 is a comparison of the inhibition of elastase by various PAI-1 mutants and by α1-proteinase inhibitor. As can be seen in this figure the PAI-1 containing valine at 346 (R346V) and alanine at position 343 (Vn 343A) is a more efficient inhibitor of elastase than other PAI-1 mutants tested.

The references cited above are all incorporated by rference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosures as come within known or customary pratice within the art to which the invention pertains and as may be applied to the essential features hereinbefore set forth as follows in scope of the appended claims.

What is claimed is:

1. A plasminogen activator inhibitor-1 (PAI-1) mutant protein (a) that comprises an amino acid substitution at position 335 and at least one amino acid substitution at position 333 or 331 of the wild-type PAI-1 protein comprising the amino acid SEQ ID NO: 3 or that comprises an amino acid substitution at position 358 and at least one amino acid substitution at position 356 or 354 of the wild-type PAI-1 protein comprising the amino acid sequence of SEQ ID NO: 2, and (b) that has a higher affinity for binding to vitronectin, relative to the wild-type PAI-1 protein.

2. The PAI-1 mutant protein of claim 1, comprising amino acid substitutions at positions 333 and 331 of the amino acid sequence of SEQ ID NO: 3, or substitutions at positions 356 and 354 of the amino acid sequence of SEQ ID NO: 2.

3. The PAI-1 mutant protein of claim 1, further comprising one or more amino acid substitutions at one or more positions selected from the group consisting of positions: 91, 150, 154, 319, 354 and 372 of the amino acid sequence of SEQ ID NO: 3, or one or more amino acid substitutions at one or more positions selected from the group consisting of positions: 114, 173, 177, 342, 377 and 395 of the amino acid sequence of SEQ ID NO:2.

4. The PAI-1 mutant protein of claim 1, which further comprises one or more additional substitutions selected from the group consisting of:

(a) His at position 150;
(b) Thr at position 154;
(c) Leu at position 319;
(d) Ile at position 354;
(e) Ile at position 372; and
(f) Leu at position 91 of the amino acid sequence of SEQ ID NO: 3.

5. A PAI-1 mutant protein of claim 1, further comprising at least one amino acid substitution at position 343 or 346 of the amino acid sequence of SEQ ID NO: 3, or at least one amino acid substitution at position 366 or 369 of the amino acid sequence of SEQ ID NO: 2.

6. A plasminogen activator inhibitor-1 (PAI-1) mutant protein (a) that comprises an amino acid substitution at position 335 of the wild-type PAI-1 protein comprising the amino acid sequence of SEQ ID NO: 3, (b) that has a higher affinity for binding to vitronectin, relative to the wild-type PAI-1 protein, and (c) that comprises at least one amino acid substitution at positions 343 or 346 of SEQ ID NO: 3.

7. A pharmaceutical composition useful for inhibiting vitronectin-dependent cell attachment, migration and/or migration-induced cell proliferation in a subject, comprising (a) the PAI-1 mutant protein of claim 1; and
(b) a pharmaceutically acceptable carrier or excipient.

8. A plasminogen activator inhibitor-1 (PAI-1) mutant protein (a) that comprises an amino acid substitution at position 335 of the wild-type PAI-1protein comprising the amino acid sequence of SEQ ID NO: 3, (b) that has a higher affinity for binding to vitronectin, relative to the wild-type PAI-1 protein, and (c) that comprises at least one amino acid substitution at one or more positions selected from the group consisting of positions 91, 150, 154, 319, 354, and 372 SEQ ID NO: 3.

9. A plasminogen activator inhibitor-1 (PAI-1) mutant protein (a) that comprises an amino acid substitution at position 335 of the wild-type PAI-1 protein comprising the amino acid sequence of SEQ ID NO: 3, (b) that has a higher affinity for binding to vitronectin, relative to the wild-type PAI-1 protein, and (c) that comprises at least one additional amino acid substitution selected from the group consisting of: (i) His at position 150; (ii) Thr at position 154; (iii) Leu at position 319; (iv) Ile at position 354; (v) Ile at position 372; and (vi) Leu at position 91.

10. The PAI-1 mutant protein of claim 5 or 6, wherein when said amino acid substitution is at position 343, then said amino acid substitution at position 343 comprises Ala, Asp, Gly, Leu or Ile and wherein when said amino acid substitution is at position 346, then said amino acid substitution at position 346 comprises Ala, Val, Asp, Phe or Gly.

11. A plasminogen activator inhibitor-1 (PAI-1) mutant protein (a) that comprises an amino acid substitution at position 358 of the wild-type PAI-1 protein comprising the amino acid sequence of SEQ ID NO: 2, (b) that has a higher affinity for binding to vitronectin, relative to the wild-type PAI-1 protein, and (c) that comprises at least one amino acid substitution at one or more positions selected from the group consisting of positions 114, 173, 177, 342, 377 and 395 of SEQ ID NO: 2.

12. A plasminogen activator inhibitor-1 (PAI-1) mutant protein (a) that comprises an amino acid substitution at position 358 of the wild-type PAI-1 protein comprising the amino acid sequence of SEQ ID NO: 2, (b) that has a higher affinity for binding to vitronectin, relative to the wild-type PAI-1 protein, and (c) that comprises at least one additional amino acid substitution selected from the group consisting of: (i) His at position 173; (ii) Thr at position 177; (iii) Leu at position 342; (iv) Ile at position 377; (v) Ile at position 395; and (vi) Leu at position 114.

13. A plasminogen activator inhibitor-1 (PAI-1) mutant protein (a) that comprises an amino acid substitution at position 358 of the wild-type PAI-1 protein comprising the amino acid sequence of SEQ ID NO: 2, (b) that has a higher affinity for binding to vitronectin, relative to the wild-type PAI-1 protein, and (c) that comprises at least one amino acid substitution at positions 366 or 369 of SEQ ID NO: 2.

* * * * *

UNITED STATES PATENT AND TRADEMARK OFFICE
CERTIFICATE OF CORRECTION

PATENT NO. : 7,388,074 B2  Page 1 of 1
APPLICATION NO. : 10/259609
DATED : June 17, 2008
INVENTOR(S) : Daniel A. Lawrence et al.

It is certified that error appears in the above-identified patent and that said Letters Patent is hereby corrected as shown below:

In the Claims:

At Column 77, line 45, "acid SEQ" should be -- acid of SEQ --.

Signed and Sealed this

Tenth Day of February, 2009

JOHN DOLL
*Acting Director of the United States Patent and Trademark Office*

UNITED STATES PATENT AND TRADEMARK OFFICE
CERTIFICATE OF CORRECTION

| | |
|---|---|
| PATENT NO. | : 7,388,074 B2 |
| APPLICATION NO. | : 10/259609 |
| DATED | : June 17, 2008 |
| INVENTOR(S) | : Daniel A. Lawrence et al. |

It is certified that error appears in the above-identified patent and that said Letters Patent is hereby corrected as shown below:

In the Specification:

At column 1, line number 21, please delete

"STATEMENT AS TO THE RIGHTS TO INVENTIONS MADE UNDER FEDERALLY SPONSORED RESEARCH AND DEVELOPMENT

The present invention was made with U.S Government support under Grant No. HL 55374, awarded by the National Institutes of Health. The government has certain rights in this invention."

and insert

--STATEMENT OF GOVERNMENT SUPPORT

This invention was made with government support under HL055374 awarded by the National Institutes of Health. The Government has certain rights in the invention.--

Signed and Sealed this
Eighth Day of October, 2013

Teresa Stanek Rea
*Deputy Director of the United States Patent and Trademark Office*

SEQUENCE LISTING

<160> NUMBER OF SEQ ID NOS: 29

<210> SEQ ID NO 1
<211> LENGTH: 2876
<212> TYPE: DNA
<213> ORGANISM: Homo sapiens
<220> FEATURE:
<221> NAME/KEY: CDS
<222> LOCATION: (76)..(1281)
<223> OTHER INFORMATION:

<400> SEQUENCE: 1

```
gaattcctgc agctcagcag ccgccgccag agcaggacga accgccaatc gcaaggcacc        60
tctgagaact tcagg atg cag atg tct cca gcc ctc acc tgc cta gtc ctg       111
              Met Gln Met Ser Pro Ala Leu Thr Cys Leu Val Leu
                1               5                  10 ggc ctg gcc ctt gtc ttt ggt gaa ggg tct gct gtg cac cat ccc cca        159
Gly Leu Ala Leu Val Phe Gly Glu Gly Ser Ala Val His His Pro Pro
         15                  20                  25 tcc tac gtg gcc cac ctg gcc tca gac ttc ggg gtg agg gtg ttt cag        207
Ser Tyr Val Ala His Leu Ala Ser Asp Phe Gly Val Arg Val Phe Gln
     30                  35                  40 cag gtg gcg cag gcc tcc aag gac cgc aac gtg gtt ttc tca ccc tat        255
Gln Val Ala Gln Ala Ser Lys Asp Arg Asn Val Val Phe Ser Pro Tyr
45                  50                  55                  60 ggg gtg gcc tcg gtg ttg gcc atg ctc cag ctg aca aca gga gga gaa        303
Gly Val Ala Ser Val Leu Ala Met Leu Gln Leu Thr Thr Gly Gly Glu
                 65                  70                  75 acc cag cag cag att caa gca gct atg gga ttc aag att gat gac aag        351
Thr Gln Gln Gln Ile Gln Ala Ala Met Gly Phe Lys Ile Asp Asp Lys
             80                  85                  90 ggc atg gcc ccc gcc ctc cgg cat ctg tac aag gag ctc atg ggg cca        399
Gly Met Ala Pro Ala Leu Arg His Leu Tyr Lys Glu Leu Met Gly Pro
         95                 100                 105 tgg aac aag gat gag atc agc acc aca gac gcg atc ttc gtc cag cgg        447
Trp Asn Lys Asp Glu Ile Ser Thr Thr Asp Ala Ile Phe Val Gln Arg
    110                 115                 120 gat ctg aag ctg gtc cag ggc ttc atg ccc cac ttc ttc agg ctg ttc        495
Asp Leu Lys Leu Val Gln Gly Phe Met Pro His Phe Phe Arg Leu Phe
125                 130                 135                 140
```

-continued

| | | |
|---|---|---|
| cgg agc acg gtc aag caa gtg gac ttt tca gag gtg gag aga gcc aga<br>Arg Ser Thr Val Lys Gln Val Asp Phe Ser Glu Val Glu Arg Ala Arg<br>         145                 150                 155 | 543 |
| ttc atc atc aat gac tgg gtg aag aca cac aca aaa ggt atg atc agc<br>Phe Ile Ile Asn Asp Trp Val Lys Thr His Thr Lys Gly Met Ile Ser<br>    160                 165                 170 | 591 |
| aac ttg ctt ggg aaa gga gcc gtg gac cag ctg aca cgg ctg gtg ctg<br>Asn Leu Leu Gly Lys Gly Ala Val Asp Gln Leu Thr Arg Leu Val Leu<br>         175                 180                 185 | 639 |
| gtg aat gcc ctc tac ttc aac ggc cag tgg aag act ccc ttc ccc gac<br>Val Asn Ala Leu Tyr Phe Asn Gly Gln Trp Lys Thr Pro Phe Pro Asp<br>     190                 195                 200 | 687 |
| tcc agc acc cac cgc cgc ctc ttc cac aaa tca gac ggc agc act gtc<br>Ser Ser Thr His Arg Arg Leu Phe His Lys Ser Asp Gly Ser Thr Val<br>205                 210                 215                 220 | 735 |
| tct gtg ccc atg atg gct cag acc aac aag ttc aac tat act gag ttc<br>Ser Val Pro Met Met Ala Gln Thr Asn Lys Phe Asn Tyr Thr Glu Phe<br>                 225                 230                 235 | 783 |
| acc acg ccc gat ggc cat tac tac gac atc ctg gaa ctg ccc tac cac<br>Thr Thr Pro Asp Gly His Tyr Tyr Asp Ile Leu Glu Leu Pro Tyr His<br>         240                 245                 250 | 831 |
| ggg gac acc ctc agc atg ttc att gct gcc cct tat gaa aaa gag gtg<br>Gly Asp Thr Leu Ser Met Phe Ile Ala Ala Pro Tyr Glu Lys Glu Val<br>     255                 260                 265 | 879 |
| cct ctc tct gcc ctc acc aac att ctg agt gcc cag ctc atc agc cac<br>Pro Leu Ser Ala Leu Thr Asn Ile Leu Ser Ala Gln Leu Ile Ser His<br>270                 275                 280 | 927 |
| tgg aaa ggc aac atg acc agg ctg ccc cgc ctc ctg gtt ctg ccc aag<br>Trp Lys Gly Asn Met Thr Arg Leu Pro Arg Leu Leu Val Leu Pro Lys<br>285                 290                 295                 300 | 975 |
| ttc tcc ctg gag act gaa gtc gac ctc agg aag ccc cta gag aac ctg<br>Phe Ser Leu Glu Thr Glu Val Asp Leu Arg Lys Pro Leu Glu Asn Leu<br>                 305                 310                 315 | 1023 |
| gga atg acc gac atg ttc aga cag ttt cag gct gac ttc acg agt ctt<br>Gly Met Thr Asp Met Phe Arg Gln Phe Gln Ala Asp Phe Thr Ser Leu<br>         320                 325                 330 | 1071 |
| tca gac caa gag cct ctc cac gtc gcg cag gcg ctg cag aaa gtg aag<br>Ser Asp Gln Glu Pro Leu His Val Ala Gln Ala Leu Gln Lys Val Lys<br>     335                 340                 345 | 1119 |
| atc gag gtg aac gag agt ggc acg gtg gcc tcc tca tcc aca gct gtc<br>Ile Glu Val Asn Glu Ser Gly Thr Val Ala Ser Ser Thr Ala Val<br>350                 355                 360 | 1167 |
| ata gtc tca gcc cgc atg gcc ccc gag gag atc atc atg gac aga ccc<br>Ile Val Ser Ala Arg Met Ala Pro Glu Glu Ile Ile Met Asp Arg Pro<br>365                 370                 375                 380 | 1215 |
| ttc ctc ttt gtg gtc cgg cac aac ccc aca gga aca gtc ctt ttc atg<br>Phe Leu Phe Val Val Arg His Asn Pro Thr Gly Thr Val Leu Phe Met<br>                 385                 390                 395 | 1263 |
| ggc caa gtg atg gaa ccc tgaccctggg gaaagacgcc ttcatctggg<br>Gly Gln Val Met Glu Pro<br>         400 | 1311 |
| acaaaactgg agatgcatcg ggaaagaaga aactccgaag aaaagaattt tagtgttaat | 1371 |
| gactctttct gaaggaagag aagacatttg ccttttgtta aaagatggta aaccagatct | 1431 |
| gtctccaaga ccttggcctc tccttggagg acctttaggt caaactccct agtctccacc | 1491 |
| tgagaccctg ggagagaagt tgaagcaca actcccttaa ggtctccaaa ccagacggtg | 1551 |
| acgcctgcgg gaccatctgg ggcacctgct tccacccgtc tctctgccca ctcgggtctg | 1611 |
| cagacctggt tcccactgag gcccttttgca ggatggaact acggggctta caggagcttt | 1671 |

-continued

```
tgtgtgcctg gtagaaacta tttctgttcc agtcacattg ccatcactct tgtactgcct    1731
gccaccgcgg aggaggctgg tgacaggcca aaggccagtg aagaaaacac cctttcatct    1791
cagagtccac tgtggcactg ccaccccctc cccagtacag gggtgctgca ggtggcagag    1851
tgaatgtccc ccatcatgtg gcccaactct cctggcctgg ccatctccct ccccagaaac    1911
agtgtgcatg ggttattttg gagtgtaggt gacttgttta ctcattgaag cagatttctg    1971
cttccttttt a ttttatagg aatagaggaa gaaatgtcag atgcgtgccc agctcttcac    2031
cccccaatct cttggtgggg aggggtgtac ctaaatattt atcatatcct tgcccttgag    2091
tgcttgttag agagaaagag aactactaag gaaaataata ttatttaaac tcgctcctag    2151
tgtttctttg tggtctgtgt caccgtatct caggaagtcc agccacttga ctggcacaca    2211
cccctccgga catccagcgt gacggagccc acactgccac cttgtggccg cctgagaccc    2271
tcgcgccccc cgcgcccccc gcgcccctct ttttcccctt gatggaaatt gaccatacaa    2331
tttcatcctc cttcagggga tcaaaaggac ggagtggggg gacagagact cagatgagga    2391
cagagtggtt tccaatgtgt tcaatagatt taggagcaga aatgcaaggg gctgcatgac    2451
ctaccaggac agaactttcc ccaattacag ggtgactcac agccgcattg gtgactcact    2511
tcaatgtgtc atttccggct gctgtgtgtg agcagtggac acgtgagggg ggggtgggtg    2571
agagagacag gcagctcgga ttcaactacc ttagataata tttctgaaaa cctaccagcc    2631
agagggtagg gcacaaagat ggatgtaatg cactttggga ggccaaggcg ggaggattgc    2691
ttgagcccag gagttcaaga ccagcctggg caacatacca agaccccgt ctctttaaaa    2751 atatatatat tttaaatata cttaaatata tatttctaat atctttaaat atatatatat    2811
attttaaaga ccaatttatg ggagaattgc acacagatgt gaaatgaatg taatctaata    2871
gaagc                                                                  2876
```

<210> SEQ ID NO 2
<211> LENGTH: 402
<212> TYPE: PRT
<213> ORGANISM: Homo sapiens

<400> SEQUENCE: 2

```
Met Gln Met Ser Pro Ala Leu Thr Cys Leu Val Leu Gly Leu Ala Leu
1               5                   10                  15

Val Phe Gly Glu Gly Ser Ala Val His His Pro Pro Ser Tyr Val Ala
                20                  25                  30

His Leu Ala Ser Asp Phe Gly Val Arg Val Phe Gln Gln Val Ala Gln
            35                  40                  45

Ala Ser Lys Asp Arg Asn Val Val Phe Ser Pro Tyr Gly Val Ala Ser
        50                  55                  60

Val Leu Ala Met Leu Gln Leu Thr Thr Gly Gly Glu Thr Gln Gln Gln
65                  70                  75                  80

Ile Gln Ala Ala Met Gly Phe Lys Ile Asp Asp Lys Gly Met Ala Pro
                85                  90                  95

Ala Leu Arg His Leu Tyr Lys Glu Leu Met Gly Pro Trp Asn Lys Asp
                100                 105                 110

Glu Ile Ser Thr Thr Asp Ala Ile Phe Val Gln Arg Asp Leu Lys Leu
            115                 120                 125

Val Gln Gly Phe Met Pro His Phe Phe Arg Leu Phe Arg Ser Thr Val
        130                 135                 140

Lys Gln Val Asp Phe Ser Glu Val Glu Arg Ala Arg Phe Ile Ile Asn
```

-continued

```
                145                 150                 155                 160
Asp Trp Val Lys Thr His Thr Lys Gly Met Ile Ser Asn Leu Leu Gly
            165                 170                 175

Lys Gly Ala Val Asp Gln Leu Thr Arg Leu Val Leu Val Asn Ala Leu
        180                 185                 190

Tyr Phe Asn Gly Gln Trp Lys Thr Pro Phe Pro Asp Ser Ser Thr His
    195                 200                 205

Arg Arg Leu Phe His Lys Ser Asp Gly Ser Thr Val Ser Val Pro Met
210                 215                 220

Met Ala Gln Thr Asn Lys Phe Asn Tyr Thr Glu Phe Thr Thr Pro Asp
225                 230                 235                 240

Gly His Tyr Tyr Asp Ile Leu Glu Leu Pro Tyr His Gly Asp Thr Leu
                245                 250                 255

Ser Met Phe Ile Ala Ala Pro Tyr Glu Lys Glu Val Pro Leu Ser Ala
            260                 265                 270

Leu Thr Asn Ile Leu Ser Ala Gln Leu Ile Ser His Trp Lys Gly Asn
        275                 280                 285

Met Thr Arg Leu Pro Arg Leu Leu Val Leu Pro Lys Phe Ser Leu Glu
    290                 295                 300

Thr Glu Val Asp Leu Arg Lys Pro Leu Glu Asn Leu Gly Met Thr Asp
305                 310                 315                 320

Met Phe Arg Gln Phe Gln Ala Asp Phe Thr Ser Leu Ser Asp Gln Glu
                325                 330                 335

Pro Leu His Val Ala Gln Ala Leu Gln Lys Val Lys Ile Glu Val Asn
            340                 345                 350

Glu Ser Gly Thr Val Ala Ser Ser Thr Ala Val Ile Val Ser Ala
        355                 360                 365

Arg Met Ala Pro Glu Glu Ile Ile Met Asp Arg Pro Phe Leu Phe Val
    370                 375                 380

Val Arg His Asn Pro Thr Gly Thr Val Leu Phe Met Gly Gln Val Met
385                 390                 395                 400

Glu Pro

<210> SEQ ID NO 3
<211> LENGTH: 379
<212> TYPE: PRT
<213> ORGANISM: Homo sapiens

<400> SEQUENCE: 3

Val His His Pro Pro Ser Tyr Val Ala His Leu Ala Ser Asp Phe Gly
1               5                   10                  15

Val Arg Val Phe Gln Gln Val Ala Gln Ala Ser Lys Asp Arg Asn Val
            20                  25                  30

Val Phe Ser Pro Tyr Gly Val Ala Ser Val Leu Ala Met Leu Gln Leu
        35                  40                  45

Thr Thr Gly Gly Glu Thr Gln Gln Gln Ile Gln Ala Ala Met Gly Phe
    50                  55                  60

Lys Ile Asp Asp Lys Gly Met Ala Pro Ala Leu Arg His Leu Tyr Lys
65                  70                  75                  80

Glu Leu Met Gly Pro Trp Asn Lys Asp Glu Ile Ser Thr Thr Asp Ala
                85                  90                  95

Ile Phe Val Gln Arg Asp Leu Lys Leu Val Gln Gly Phe Met Pro His
            100                 105                 110

Phe Phe Arg Leu Phe Arg Ser Thr Val Lys Gln Val Asp Phe Ser Glu
```

```
                    115                 120                 125
Val Glu Arg Ala Arg Phe Ile Ile Asn Asp Trp Val Lys Thr His Thr
130                 135                 140

Lys Gly Met Ile Ser Asn Leu Leu Gly Lys Gly Ala Val Asp Gln Leu
145                 150                 155                 160

Thr Arg Leu Val Leu Val Asn Ala Leu Tyr Phe Asn Gly Gln Trp Lys
                165                 170                 175

Thr Pro Phe Pro Asp Ser Ser Thr His Arg Arg Leu Phe His Lys Ser
            180                 185                 190

Asp Gly Ser Thr Val Ser Val Pro Met Met Ala Gln Thr Asn Lys Phe
        195                 200                 205

Asn Tyr Thr Glu Phe Thr Thr Pro Asp Gly His Tyr Tyr Asp Ile Leu
    210                 215                 220

Glu Leu Pro Tyr His Gly Asp Thr Leu Ser Met Phe Ile Ala Ala Pro
225                 230                 235                 240

Tyr Glu Lys Glu Val Pro Leu Ser Ala Leu Thr Asn Ile Leu Ser Ala
                245                 250                 255

Gln Leu Ile Ser His Trp Lys Gly Asn Met Thr Arg Leu Pro Arg Leu
            260                 265                 270

Leu Val Leu Pro Lys Phe Ser Leu Glu Thr Glu Val Asp Leu Arg Lys
        275                 280                 285

Pro Leu Glu Asn Leu Gly Met Thr Asp Met Phe Arg Gln Phe Gln Ala
    290                 295                 300

Asp Phe Thr Ser Leu Ser Asp Gln Glu Pro Leu His Val Ala Gln Ala
305                 310                 315                 320

Leu Gln Lys Val Lys Ile Glu Val Asn Glu Ser Gly Thr Val Ala Ser
                325                 330                 335

Ser Ser Thr Ala Val Ile Val Ser Ala Arg Met Ala Pro Glu Glu Ile
            340                 345                 350

Ile Met Asp Arg Pro Phe Leu Phe Val Val Arg His Asn Pro Thr Gly
        355                 360                 365

Thr Val Leu Phe Met Gly Gln Val Met Glu Pro
    370                 375

<210> SEQ ID NO 4
<211> LENGTH: 7
<212> TYPE: PRT
<213> ORGANISM: Homo sapiens

<400> SEQUENCE: 4

Met Thr Met Ile Thr Asn Ser
1               5

<210> SEQ ID NO 5
<211> LENGTH: 21
<212> TYPE: DNA
<213> ORGANISM: Unknown
<220> FEATURE:
<223> OTHER INFORMATION: Primer

<400> SEQUENCE: 5
gtctcagccg ccatggcccc c                                              21

<210> SEQ ID NO 6
<211> LENGTH: 21
<212> TYPE: DNA
<213> ORGANISM: Unknown
<220> FEATURE:
```

```
<223> OTHER INFORMATION: Primer

<400> SEQUENCE: 6
gtctcagccg tcatggcccc c                                        21

<210> SEQ ID NO 7
<211> LENGTH: 21
<212> TYPE: DNA
<213> ORGANISM: Unknown
<220> FEATURE:
<223> OTHER INFORMATION: Primer

<400> SEQUENCE: 7
gctgtcatag cctcagcccg c                                        21

<210> SEQ ID NO 8
<211> LENGTH: 30
<212> TYPE: DNA
<213> ORGANISM: Unknown
<220> FEATURE:
<223> OTHER INFORMATION: Primer

<400> SEQUENCE: 8
gctgtcatag cctcagccgt catggccccc                                30

<210> SEQ ID NO 9
<211> LENGTH: 30
<212> TYPE: DNA
<213> ORGANISM: Unknown
<220> FEATURE:
<223> OTHER INFORMATION: Primer

<400> SEQUENCE: 9
gctgtcatag cctcagccgc catggccccc                                30

<210> SEQ ID NO 10
<211> LENGTH: 2876
<212> TYPE: DNA
<213> ORGANISM: Homo sapiens

<400> SEQUENCE: 10
gcttctatta gattacattc atttcacatc tgtgtgcaat tctcccataa attggtcttt      60
aaaatatata tatatattta agatattag aaatatatat ttaagtatat ttaaaatata     120 tatatttta aagagacggg ggtcttggta tgttgcccag gctggtcttg aactcctggg     180
ctcaagcaat cctcccgcct tggcctccca aagtgcatta catccatctt tgtgccctac     240
cctctggctg gtaggttttc agaaatatta tctaaggtag ttgaatccga gctgcctgtc     300
tctctcaccc accccccct cacgtgtcca ctgctcacac acagcagccg gaaatgacac     360
attgaagtga gtcaccaatg cggctgtgag tcaccctgta attggggaaa gttctgtcct     420
ggtaggtcat gcagcccctt gcatttctgc tcctaaatct attgaacaca ttggaaacca     480
ctctgtcctc atctgagtct ctgtcccccc actccgtcct tttgatcccc tgaaggagga     540
tgaaattgta tggtcaattt ccatcaaggg gaaaagagg ggcgcggggg gcgcgggggg     600
cgcgagggtc tcaggcggcc acaaggtggc agtgtgggct ccgtcacgct ggatgtccgg     660
aggggtgtgt gccagtcaag tggctggact tcctgagata cggtgacaca gaccacaaag     720
aaacactagg agcgagttta aataatatta ttttccttag tagttctctt tctctctaac     780
aagcactcaa gggcaaggat atgataaata tttaggtaca cccctcccca ccaagagatt     840 gggggggtgaa gagctgggca cgcatctgac atttcttcct ctattcctat aaaaataaaa     900
```

```
ggaagcagaa atctgcttca atgagtaaac aagtcaccta cactccaaaa taacccatgc    960
acactgtttc tggggaggga gatggccagg ccaggagagt tgggccacat gatgggggac   1020
attcactctg ccacctgcag caccectgta ctggggaggg gtggccagtg ccacagtgga   1080
ctctgagatg aaagggtgtt tcttccactg gcctttggcc tgtcaccagc ctcctccgcg   1140
gtggcaggca gtacaagagt gatggcaatg tgactgaaac agaaatagtt ctaccaggc    1200
acacaaaagc tcctgtaagc cccgtagttc catcctgcaa agggcctcag tgggaaccag   1260
gtctgcagac ccgagtgggc agagagacgg gtggaagcag gtgccccaga tggtcccgca   1320
ggcgtcaccg tctggtttgg agaccttaag ggagttgtgc ttcaaacttc tctcccaggg   1380
tctcaggtgg agactaggga gtttgaccta aaggtcctcc aaggagaggc caaggtcttg   1440
gagacagatc tggtttacca tcttttaaca aaaggcaaat gtcttctctt ccttcagaaa   1500
gagtcattaa cactaaaatt cttttcttcg gagtttcttc tttcccgatg catctccagt   1560
tttgtcccag atgaaggcgt ctttccccag ggtcagggtt ccatcacttg gcccatgaaa   1620
aggactgttc ctgtggggtt gtgccggacc acaaagagga agggtctgtc catgatgatc   1680
tcctcggggg ccatgcgggc tgagactatg acagctgtgg atgaggaggc caccgtgcca   1740
ctctcgttca cctcgatctt cactttctgc agcgcctgcg cgacgtggag aggctcttgg   1800
tctgaaagac tcgtgaagtc agcctgaaac tgtctgaaca tgtcggtcat tcccaggttc   1860
tctaggggct tcctgaggtc gacttcagtc tccagggaga acttgggcag aaccaggagg   1920
cggggcagcc tggtcatgtt gcctttccag tggctgatga gctgggcact cagaatgttg   1980
gtgagggcag agagaggcac ctcttttca taaggggcag caatgaacat gctgagggtg    2040
tccccgtggt agggcagttc caggatgtcg tagtaatggc catcgggcgt ggtgaactca   2100
gtatagttga acttgttggt ctgagccatc atgggcacag agacagtgct gccgtctgat   2160
ttgtggaaga ggcggcggtg ggtgctggag tcggggaagg gagtcttcca ctggccgttg   2220
aagtagaggg cattcaccag caccagccgt gtcagctggt ccacggctcc tttcccaagc   2280
aagttgctga tcatacctt tgtgtgtgtc ttcacccagt cattgatgat gaatctggct    2340
ctctccacct ctgaaaagtc cacttgcttg accgtgctcc ggaacagcct gaagaagtgg   2400
ggcatgaagc cctggaccag cttcagatcc cgctggacga agatcgcgtc tgtggtgctg   2460
atctcatcct tgttccatgg ccccatgagc tccttgtaca gatgccggag ggcgggggcc   2520
atgcccttgt catcaatctt gaatcccata gctgcttgaa tctgctgctg ggtttctcct   2580
cctgttgtca gctggagcat ggccaacacc gaggccaccc cataggtgtga aaaccacg    2640
ttgcggtcct tggaggcctg cgccacctgc tgaaacaccc tcaccccgaa gtctgaggcc   2700
aggtgggcca cgtaggatgg gggatggtgc acagcagacc cttcaccaaa gacaagggcc   2760
aggcccagga ctaggcaggt gagggctgga gacatctgca tcctgaagtt ctcagaggtg   2820
ccttgcgatt ggcggttcgt cctgctctgg cggcggctgc tgagctgcag gaattc       2876
```

<210> SEQ ID NO 11
<211> LENGTH: 20
<212> TYPE: PRT
<213> ORGANISM: Homo sapiens

<400> SEQUENCE: 11

Gly Thr Val Ala Ser Ser Ser Thr Ala Val Ile Val Ser Ala Arg Met
1               5                   10                  15

Ala Pro Glu Glu

```
<210> SEQ ID NO 12
<211> LENGTH: 5
<212> TYPE: PRT
<213> ORGANISM: Homo sapiens

<400> SEQUENCE: 12

Ser Ala Val His His
1               5

<210> SEQ ID NO 13
<211> LENGTH: 5
<212> TYPE: PRT
<213> ORGANISM: Homo sapiens

<400> SEQUENCE: 13

Val His His Pro Pro
1               5

<210> SEQ ID NO 14
<211> LENGTH: 6
<212> TYPE: PRT
<213> ORGANISM: Homo sapiens

<400> SEQUENCE: 14

Gly Arg Gly Asp Ser Pro
1               5

<210> SEQ ID NO 15
<211> LENGTH: 6
<212> TYPE: PRT
<213> ORGANISM: Homo sapiens

<400> SEQUENCE: 15

Gly Arg Gly Glu Ser Pro
1               5

<210> SEQ ID NO 16
<211> LENGTH: 8
<212> TYPE: PRT
<213> ORGANISM: Homo sapiens

<400> SEQUENCE: 16

Val Ser Ala Arg Met Ala Pro Glu
1               5

<210> SEQ ID NO 17
<211> LENGTH: 8
<212> TYPE: PRT
<213> ORGANISM: Homo sapiens

<400> SEQUENCE: 17

Val Ser Ala Ala Met Ala Pro Glu
1               5

<210> SEQ ID NO 18
<211> LENGTH: 8
<212> TYPE: PRT
<213> ORGANISM: Homo sapiens

<400> SEQUENCE: 18

Val Ser Ala Val Met Ala Pro Glu
1               5
```

```
<210> SEQ ID NO 19
<211> LENGTH: 8
<212> TYPE: PRT
<213> ORGANISM: Homo sapiens

<400> SEQUENCE: 19

Val Ser Ala Gly Met Ala Pro Glu
1               5

<210> SEQ ID NO 20
<211> LENGTH: 8
<212> TYPE: PRT
<213> ORGANISM: Homo sapiens

<400> SEQUENCE: 20

Val Ser Ala Asp Met Ala Pro Glu
1               5

<210> SEQ ID NO 21
<211> LENGTH: 8
<212> TYPE: PRT
<213> ORGANISM: Homo sapiens

<400> SEQUENCE: 21

Ala Ser Ala Arg Met Ala Pro Glu
1               5

<210> SEQ ID NO 22
<211> LENGTH: 8
<212> TYPE: PRT
<213> ORGANISM: Homo sapiens

<400> SEQUENCE: 22

Asp Ser Ala Arg Met Ala Pro Glu
1               5

<210> SEQ ID NO 23
<211> LENGTH: 8
<212> TYPE: PRT
<213> ORGANISM: Homo sapiens

<400> SEQUENCE: 23

Gly Ser Ala Arg Met Ala Pro Glu
1               5

<210> SEQ ID NO 24
<211> LENGTH: 8
<212> TYPE: PRT
<213> ORGANISM: Homo sapiens

<400> SEQUENCE: 24

Leu Ser Ala Arg Met Ala Pro Glu
1               5

<210> SEQ ID NO 25
<211> LENGTH: 8
<212> TYPE: PRT
<213> ORGANISM: Homo sapiens

<400> SEQUENCE: 25

Ile Ser Ala Arg Met Ala Pro Glu
1               5

<210> SEQ ID NO 26
```

```
<211> LENGTH: 8
<212> TYPE: PRT
<213> ORGANISM: Homo sapiens

<400> SEQUENCE: 26

Ala Ser Ala Val Met Ala Pro Glu
1               5

<210> SEQ ID NO 27
<211> LENGTH: 8
<212> TYPE: PRT
<213> ORGANISM: Homo sapiens

<400> SEQUENCE: 27

Ala Ser Ala Ala Met Ala Pro Glu
1               5

<210> SEQ ID NO 28
<211> LENGTH: 8
<212> TYPE: PRT
<213> ORGANISM: Homo sapiens

<400> SEQUENCE: 28

Ala Ser Ala Asp Met Ala Pro Glu
1               5

<210> SEQ ID NO 29
<211> LENGTH: 4
<212> TYPE: PRT
<213> ORGANISM: Artificial Sequence
<220> FEATURE:
<223> OTHER INFORMATION: Synthetic sequence

<400> SEQUENCE: 29

Ala Ala Pro Val
1
```